(12) United States Patent
Toan et al.

(10) Patent No.: US 7,087,753 B2
(45) Date of Patent: Aug. 8, 2006

(54) NAPHTHYLTRIAZINES AS STABILIZERS FOR ORGANIC MATERIAL

(75) Inventors: Vien Van Toan, Rheinfelden (CH);
Georges Metzger, Moernach (FR);
Thomas Schäfer, Basel (CH);
Stéphane Biry, Village-Neuf (FR);
Christophe Bulliard, Basel (CH);
Dieter Reinehr, Kandern (DE); Peter Michaelis, Geispitzen (FR)

(73) Assignee: Ciba Specialty Chemicals Corp., Tarrytown, NY (US)

( * ) Notice: Subject to any disclaimer, the term of this patent is extended or adjusted under 35 U.S.C. 154(b) by 0 days.

(21) Appl. No.: 11/098,640

(22) Filed: Apr. 4, 2005

(65) Prior Publication Data

US 2005/0169859 A1    Aug. 4, 2005

Related U.S. Application Data

(63) Continuation of application No. 10/492,721, filed as application No. PCT/EP02/11347 on Oct. 10, 2002, now abandoned.

(30) Foreign Application Priority Data

Oct. 18, 2001 (CH) ................................ 1919/01

(51) Int. Cl.
*C07D 251/24* (2006.01)
*A61K 7/42* (2006.01)
*G03C 1/005* (2006.01)

(52) U.S. Cl. .................. 544/211; 544/213; 544/217; 524/100; 252/380

(58) Field of Classification Search .............. 544/211, 544/213, 217; 524/100; 252/380
See application file for complete search history.

(56) References Cited

U.S. PATENT DOCUMENTS

| | | | | |
|---|---|---|---|---|
| 1,551,095 A | | 8/1925 | Fritzsche et al. ........... 260/248 |
| 3,118,887 A | * | 1/1964 | Hardy et al. ................ 544/216 |
| 3,242,175 A | | 3/1966 | Duennenberger et al. ... 260/248 |
| 3,244,708 A | | 4/1966 | Duennenberger et al. ... 260/248 |
| 3,478,024 A | * | 11/1969 | Altermatt .................... 544/216 |

FOREIGN PATENT DOCUMENTS

GB          1321561        6/1973

| | | | |
|---|---|---|---|
| WO | | 00/14076 | 3/2000 |
| WO | | WO-00/29392 | * 5/2000 |

* cited by examiner

Primary Examiner—Venkataraman Balasubramanian
(74) Attorney, Agent, or Firm—Tyler A. Stevenson

(57) ABSTRACT

Novel compounds of formula I are described

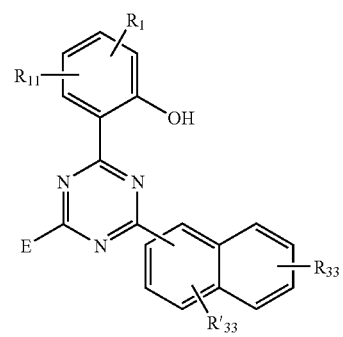

(I)

wherein
E corresponds to the formula

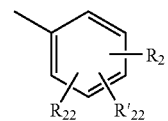

or to the formula

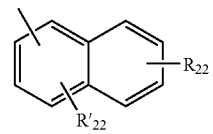

and the radicals $R_1$, $R_2$, $R_{11}$, $R_{22}$, $R'_{22}$, $R'_{33}$ and $R'_{33}$ are as defined in claim 1. Compounds of formula I are suitable for stabilizing organic material, especially plastics materials, surface-coatings, cosmetic preparations, sun protection agents or photographic material, against damage by light, oxygen and/or heat.

13 Claims, No Drawings

NAPHTHYLTRIAZINES AS STABILIZERS FOR ORGANIC MATERIAL

This is a continuation of application Ser. No. 10/492,721, filed Oct. 6, 2004, abandoned, which is a 371 of international application No. PCT/EP02/11347, filed Oct. 10, 2002, the disclosures of which are hereby incorporated by reference.

The invention relates to novel compounds of the 2-hydroxyphenyl-1,3,5-triazine type that comprise one or two α- or β-bonded naphthyl groups, to the use of those compounds for stabilizing organic material, especially in plastics materials, surface-coatings, cosmetic preparations, sun protection agents or photographic material, against damage by light, oxygen and/or heat, and to correspondingly stabilised organic material.

If it is desired to increase the light stability of an organic material, especially a coating, a light stabiliser is usually added. A class of light stabilisers that is very often employed comprises the UV absorbers, which protect the material by absorbing harmful radiation by way of chromophores. An important group of UV absorbers is formed by the 2-hydroxyphenyl-1,3,5-triazines (U.S. Pat. No. 3,118,887, U.S. Pat. No. 3,242,175, U.S. Pat. No. 3,244,708, GB-A-1 321 561).

Reactions of cyanuric chloride with naphthyl compounds are described in U.S. Pat. No. 1,551,095, U.S. Pat. No. 3,478,024 and U.S. Pat. No. 3,118,887. A specific compound of the 2-hydroxyphenyl-4,6-bis(α-naphthyl)-1,3,5-triazine type is recommended as an additive to photographic material in GB-A-1 321 561.

Specific compounds of the 2-hydroxyphenyl-4-naphthyl-1,3,5-triazine class have now been found that surprisingly exhibit especially good stabiliser properties.

The invention therefore relates to a compound of formula I

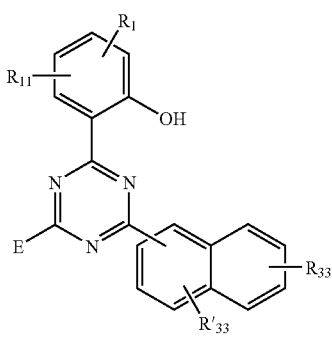

(I)

wherein

E corresponds to the formula

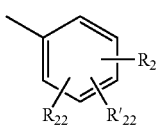

or to the formula

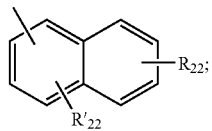

$R_1$ is hydrogen or $OR_3$;

$R_2$ is H, $C_1$–$C_{18}$alkyl; $C_2$–$C_6$alkenyl; phenyl; phenyl substituted by $C_1$–$C_8$alkyl or by $C_1$–$C_8$alkoxy; $C_7$–$C_{11}$phenylalkyl; $C_5$–$C_{12}$cycloalkyl; $COOR_4$; CN; $NH_2$, $NHR_7$, —$N(R_7)(R_8)$, NH—CO—$R_5$; halogen; $C_1$–$C_{18}$haloalkyl; —S—$R_3$ or —O—$R_3$;

$R_3$ is H, $C_1$–$C_{18}$alkyl; $C_5$–$C_{12}$cycloalkyl; $C_3$–$C_{18}$alkenyl; phenyl; $C_1$–$C_{18}$alkyl that is substituted by phenyl, vinylphenyl, OH, $C_1$–$C_{18}$alkoxy, $C_5$–$C_{12}$cycloalkoxy, $C_3$–$C_{18}$alkenyloxy, halogen, —COOH, —$COOR_4$, —O—CO—$R_5$, —O—CO—O—$R_6$, —CO—$NH_2$, —CO—$NHR_7$, —CO—$N(R_7)(R_8)$, CN, $NH_2$, $NHR_7$, —$N(R_7)(R_8)$, —NH—CO—$R_5$, phenoxy, $C_1$–$C_{18}$alkyl-substituted phenoxy, phenyl-$C_1$–$C_4$-alkoxy, $C_6$–$C_{15}$bicycloalkoxy, $C_6$–$C_{15}$bicycloalkyl-alkoxy, $C_6$–$C_{15}$bicycloalkenyl-alkoxy and/or by $C_6$–$C_{15}$tricycloalkoxy; $C_5$–$C_{12}$cycloalkyl that is substituted by OH, $C_1$–$C_4$alkyl, $C_2$–$C_6$alkenyl or by —O—CO—$R_5$; —CO—$R_9$ or —$SO_2$—$R_{10}$; or $R_3$ is $C_3$–$C_{50}$alkyl that is interrupted by one or more oxygen atoms and/or is substituted by OH, phenoxy or by $C_7$–$C_{18}$alkylphenoxy; or $R_3$ has one of the definitions —A; —$CH_2$—CH(XA)—$CH_2$—O—$R_{12}$; —$CR_{13}R'_{13}$—$(CH_2)_m$—X—A;

—$CH_2$—CH(OA)—$R_{14}$; —$CH_2$—CH(OH)—$CH_2$—XA;

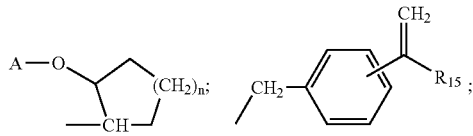

—$CR_{15}R'_{15}$—C(=$CH_2$)—$R''_{15}$; —$CR_{13}R'_{13}$—$(CH_2)_m$—CO—X—A;

—$CR_{13}R'_{13}$—$(CH_2)_m$—CO—O—$CR_{15}R'_{15}$—C(=$CH_2$)—$R''_{15}$ or —CO—O—$CR_{15}R'_{15}$—C(=$CH_2$)—$R''_{15}$, wherein A is —CO—$CR_{16}$=CH—$R_{17}$;

$R_4$ is $C_1$–$C_{18}$alkyl; $C_3$–$C_{18}$alkenyl; phenyl; $C_7$–$C_{11}$phenylalkyl; $C_5$–$C_{12}$cycloalkyl; or $C_3$–$C_{50}$alkyl that is interrupted by one or more of —O—, —NH—, —$NR_7$— and —S— and may be substituted by OH, phenoxy or by $C_7$–$C_{18}$alkylphenoxy; or is $C_2$–$C_{12}$hydroxyalkyl;

$R_5$ is H; $C_1$–$C_{18}$alkyl; $C_1$–$C_{18}$alkyl substituted by COOH or by $COOR_4$; $C_2$–$C_{18}$alkenyl; $C_2$–$C_{18}$-alkenyl substituted by COOH or by $COOR_4$; $C_5$–$C_{12}$cycloalkyl; phenyl; $C_7$–$C_{11}$phenylalkyl; $C_6$–$C_{15}$bicycloalkyl; $C_6$–$C_{15}$bicycloalkenyl; or $C_6$–$C_{15}$tricycloalkyl;

$R_6$ is H; $C_1$–$C_{18}$alkyl; $C_3$–$C_{18}$alkenyl; phenyl; $C_7$–$C_{11}$phenylalkyl; or $C_5$–$C_{12}$cycloalkyl;

$R_7$ and $R_8$, independently of each other, are $C_1$–$C_{12}$alkyl; $C_3$–$C_{12}$alkoxyalkyl; $C_4$–$C_{16}$dialkylaminoalkyl; or $C_5$–$C_{12}$cycloalkyl; or together form $C_3$–$C_9$-alkylene, -oxaalkylene or -azaalkylene;

$R_9$ is $C_1$–$C_{18}$alkyl; $C_2$–$C_{18}$alkenyl; phenyl; $C_5$–$C_{12}$cycloalkyl; $C_7$–$C_{11}$phenylalkyl; $C_6$–$C_{15}$-bicycloalkyl, $C_6$–$C_{15}$bicycloalkyl-alkyl, $C_6$–$C_{15}$bicycloalkenyl, or $C_6$–$C_{15}$tricycloalkyl;

R$_{10}$ is C$_1$–C$_{12}$alkyl; phenyl; naphthyl or C$_7$–C$_{14}$alkylphenyl; the radicals R$_{11}$, R$_{22}$ and R$_{33}$, independently of one another, are H; C$_1$–C$_{18}$alkyl; C$_3$–C$_6$alkenyl; C$_5$–C$_{12}$cycloalkyl; phenyl; naphthyl; biphenylyl; C$_7$–C$_{11}$phenylalkyl; C$_7$–C$_{14}$alkylphenyl; halogen; C$_1$–C$_{18}$haloalkyl; or C$_1$–C$_{18}$alkoxy;

R$_{12}$ is C$_1$–C$_{18}$alkyl; C$_3$–C$_{18}$alkenyl; phenyl; phenyl substituted by from one to three of the radicals C$_1$–C$_8$alkyl, C$_1$–C$_8$alkoxy, C$_3$–C$_8$alkenyloxy, halogen and trifluoromethyl; C$_7$–C$_{11}$phenylalkyl; C$_5$–C$_{12}$cycloalkyl; C$_6$–C$_{15}$tricycloalkyl; C$_6$–C$_{15}$bicycloalkyl; C$_6$–C$_{15}$bicycloalkyl-alkyl; C$_6$–C$_{15}$bicycloalkenyl-alkyl; —CO—R$_5$; or C$_3$–C$_{50}$alkyl that is interrupted by one or more of —O—, —NH—, —NR$_7$— and —S— and may be substituted by OH, phenoxy or by C$_7$–C$_{18}$alkylphenoxy;

R$_{13}$ and R'$_{13}$, independently of each other, are H; C$_1$–C$_{18}$alkyl; or phenyl;

R$_{14}$ is C$_1$–C$_{18}$alkyl; C$_3$–C$_{12}$alkoxyalkyl; phenyl; or phenyl-C$_1$–C$_4$alkyl;

R$_{15}$, R'$_{15}$ and R''$_{15}$, independently of one another, are H or CH$_3$;

R$_{16}$ is H; —CH$_2$—COO—R$_4$; C$_1$–C$_4$alkyl; or CN;

R$_{17}$ is H; —COOR$_4$; C$_1$–C$_{17}$alkyl; or phenyl;

R'$_{22}$ and R'$_{33}$, independently of each other, have one of the definitions of R$_{11}$ or OR$_3$; or are NH$_2$, NHR$_7$, NH—CO—R$_5$; —S—R$_3$ or —N(R$_7$)(R$_8$);

X is —NH—; —NR$_7$—; —O—; —NH—(CH$_2$)$_p$—NH—; or —O—(CH$_2$)$_q$—NH—; and the indices are as follows:

m is the number 0–19;
n is the number 1–8;
p is the number 0–4; and
q is the number 2–4.

Within the scope of the definitions given, the radicals R$_2$ to R$_{10}$, R$_{12}$ to R$_{14}$, R$_{16}$ and R$_{17}$ as alkyl are branched or unbranched alkyl, such as e.g. methyl, ethyl, propyl, isopropyl, n-butyl, sec-butyl, isobutyl, tert-butyl, 2-ethylbutyl, n-pentyl, isopentyl, 1-methylpentyl, 1,3-dimethylbutyl, n-hexyl, 1-methylhexyl, n-heptyl, isoheptyl, 1,1,3,3-tetramethylbutyl, 1-methylheptyl, 3-methylheptyl, n-octyl, 2-ethylhexyl, 1,1,3-trimethylhexyl, 1,1,3,3-tetramethylpentyl, nonyl, decyl, undecyl, 1-methylundecyl, dodecyl, 1,1,3,3,5,5-hexamethylhexyl, tridecyl, tetradecyl, pentadecyl, hexadecyl, heptadecyl, octadecyl.

The radicals R$_2$ to R$_9$, R$_{12}$ as C$_5$–C$_{12}$cycloalkyl include cyclopentyl, cyclohexyl, cycloheptyl, cyclooctyl, cyclononyl, cyclodecyl, cycloundecyl and cyclodocecyl. Cyclopentyl, cyclohexyl, cyclooctyl and cyclododecyl are preferred.

R$_2$ to R$_6$, R$_9$, R$_{11}$ and R$_{12}$ as alkenyl include, within the scope of the definitions given, inter alia allyl, isopropenyl, 2-butenyl, 3-butenyl, isobutenyl, n-penta-2,4-dienyl, 3-methyl-but-2-enyl, n-oct-2-enyl, n-dodec-2-enyl, isododecenyl, n-dodec-2-enyl and n-octadec-4-enyl.

Substituted alkyl, cycloalkyl or phenyl radicals may be mono- or poly-substituted and may carry substituents at the binding carbon atom (in the α-position) or at other carbon atoms; if a substituent is bonded by a hetero atom (such as e.g. alkoxy), it is preferably not in the α-position and the substituted alkyl radical comprises 2, especially 3, or more carbon atoms. A plurality of substituents is preferably bonded to different carbon atoms.

Alkyl interrupted by —O—, —NH—, —NR$_7$— and/or by —S— may be interrupted by one or more of the mentioned groups, in each case normally one group being inserted into a bond and hetero-hetero bonds, such as, for example, O—O, S—S, NH—NH etc. not occurring; if the interrupted alkyl is, in addition, substituted, the substituents are not normally in the α-position with respect to the hetero atom. If a plurality of interrupting groups of the type —O—, —NH—, —NR$_7$— and —S— occurs in a radical, those groups are usually identical.

Aryl is generally an aromatic hydrocarbon radical, for example phenyl, biphenylyl or naphthyl, with phenyl and biphenylyl being preferred. Aralkyl generally denotes alkyl substituted by aryl, especially by phenyl; C$_7$–C$_{20}$aralkyl therefore includes, for example, benzyl, α-methylbenzyl, phenylethyl, phenylpropyl, phenylbutyl, phenylpentyl and phenylhexyl; C$_7$–C$_{11}$phenylalkyl preferably comprises benzyl, α-methylbenzyl and α,α-dimethylbenzyl.

Alkylphenyl and alkylphenoxy are alkyl-substituted phenyl and phenoxy, respectively.

A halogen substituent is —F, —Cl, —Br or —I; —F or —Cl, and especially —Cl, is preferred. Haloalkyl is especially chloroalkyl or trifluoromethyl; trifluoromethyl is of particular importance industrially.

C$_1$–C$_{20}$Alkylene is e.g. methylene, ethylene, propylene, butylene, pentylene, hexylene, etc. The alkyl chain may also be branched in that case, such as e.g. in isopropylene.

C$_4$–C$_{12}$Cycloalkenyl is e.g. 2-cyclobuten-1-yl, 2-cyclopenten-1-yl, 2,4-cyclopentadien-1-yl, 2-cyclohexen-1-yl, 2-cyclohepten-1-yl or 2-cycloocten-1-yl.

C$_6$–C$_{15}$Bicycloalkyl is e.g. bornyl, norbornyl, 2.2.2-bicyclooctyl. Bornyl and norbornyl, and especially bornyl and norborn-2-yl, are preferred.

C$_6$–C$_{15}$Bicycloalkoxy is, for example, bornyloxy or norborn-2-yl-oxy.

C$_6$–C$_{15}$Bicycloalkyl-alkyl or -alkoxy is alkyl or alkoxy substituted by bicycloalkyl, the total number of carbon atoms being 6–15; examples are norbornane-2-methyl and norbornane-2-methoxy.

C$_6$–C$_{15}$Bicycloalkenyl is e.g. norbornenyl, norbornadienyl. Norbornenyl, and especially norborn-5-enyl, is preferred.

C$_6$–C$_{15}$Bicycloalkenyl-alkoxy is alkoxy substituted by bicycloalkenyl, the total number of carbon atoms being 6–15; an example is norborn-5-enyl-2-methoxy.

C$_6$–C$_{15}$Tricycloalkyl is e.g. 1-adamantyl, 2-adamantyl; 1-adamantyl is preferred.

C$_6$–C$_{15}$Tricycloalkoxy is e.g. adamantyloxy.

C$_3$–C$_{12}$Heteroaryl is preferably pyridinyl, pyrimidinyl, triazinyl, pyrrolyl, furanyl, thiophenyl or quinolinyl.

Preference is given to those compounds of formula I wherein the naphthyl unit or the naphthyl units are bonded in the α-position in accordance with the formula

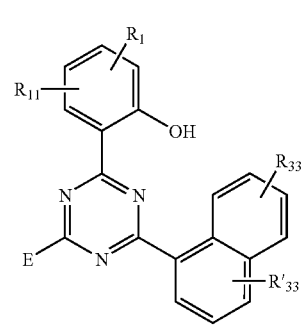

(Ia)

wherein

E corresponds to the formula

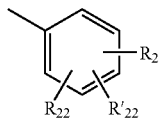

or to the formula

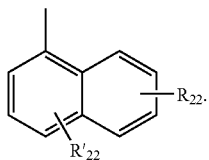

Of particular interest industrially are compounds of formula I wherein the naphthyl unit or the naphthyl units are bonded in the β-position in accordance with the formula

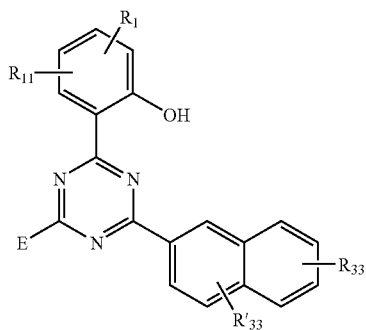

(Ib)

wherein

E corresponds to the formula

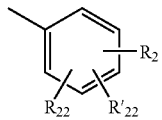

or to the formula

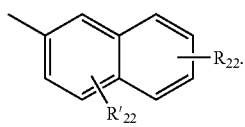

Typical compounds of formula I include those wherein $R_1$ is hydrogen or $OR_3$;

$R_2$ is H, $C_1$–$C_{18}$alkyl; $C_2$–$C_6$alkenyl; phenyl; phenyl substituted by $C_1$–$C_8$alkyl or by $C_1$–$C_8$alkoxy; NH—CO—$R_5$; halogen; $C_1$–$C_{18}$haloalkyl; or $C_1$–$C_{18}$alkoxy;

$R_3$ is H, $C_1$–$C_{18}$alkyl; $C_5$–$C_{12}$cycloalkyl; $C_3$–$C_{18}$alkenyl; phenyl; $C_1$–$C_{18}$alkyl that is substituted by phenyl, vinylphenyl, OH, $C_1$–$C_{18}$alkoxy, $C_5$–$C_{12}$cycloalkoxy, $C_3$–$C_{18}$alkenyloxy, halogen, —COOH, —COO$R_4$, —O—CO—$R_5$, —O—CO—O—$R_6$, —CO—$NH_2$, —CO—$NHR_7$, —CO—$N(R_7)(R_8)$, CN, $NH_2$, $NHR_7$, —$N(R_7)(R_8)$, —NH—CO—$R_5$, phenoxy, $C_1$–$C_{18}$alkyl-substituted phenoxy and/or by phenyl-$C_1$–$C_4$alkoxy; $C_5$–$C_{12}$cycloalkyl that is substituted by OH, $C_1$–$C_4$alkyl, $C_2$–$C_6$alkenyl or by —O—CO—$R_5$; or $R_3$ is —$SO_2$—$R_{10}$; or $R_3$ is $C_3$–$C_{50}$alkyl that is interrupted by one or more oxygen atoms and/or is substituted by OH, phenoxy or by $C_7$–$C_{18}$alkylphenoxy; or $R_3$ has one of the definitions —CO—CH=$CH_2$ and —CO—C($CH_3$)=$CH_2$;

$R_4$ is $C_1$–$C_{18}$alkyl; $C_3$–$C_{18}$alkenyl; phenyl; $C_7$–$C_{11}$phenylalkyl; $C_5$–$C_{12}$cycloalkyl; or $C_3$–$C_{50}$alkyl that is interrupted by one or more of —O—, —NH—, —$NR_7$— and —S— and may be substituted by OH, phenoxy or by $C_7$–$C_{18}$alkylphenoxy; or is $C_2$–$C_{12}$hydroxyalkyl;

$R_5$ is H; $C_1$–$C_{18}$alkyl; $C_2$–$C_{18}$alkenyl; $C_5$–$C_{12}$cycloalkyl; phenyl; or $C_7$–$C_{11}$phenylalkyl;

$R_6$ is H; $C_1$–$C_{18}$alkyl; $C_3$–$C_{18}$alkenyl; phenyl; $C_7$–$C_{11}$phenylalkyl; or $C_5$–$C_{12}$cycloalkyl;

$R_7$ and $R_8$, independently of each other, are $C_1$–$C_{12}$alkyl; $C_3$–$C_{12}$alkoxyalkyl; $C_4$–$C_{16}$dialkylaminoalkyl; or cyclohexyl; or together form $C_3$–$C_9$-alkylene or -oxaalkylene;

$R_{10}$ is $C_1$–$C_{12}$alkyl; phenyl; naphthyl or $C_7$–$C_{14}$alkylphenyl; the radicals $R_{11}$, $R_{22}$ and $R_{33}$, independently of one another, are H, $C_7$–$C_{11}$phenylalkyl or $C_1$–$C_8$alkyl; and $R'_{22}$ and $R'_{33}$, independently of each other, are H; $C_1$–$C_8$alkyl; $C_3$–$C_6$alkenyl; $C_7$–$C_{11}$phenylalkyl; $C_5$–$C_{12}$cycloalkyl; phenyl; naphthyl; biphenylyl; $C_7$–$C_{11}$phenylalkyl; $C_7$–$C_{14}$alkylphenyl; $NHR_7$; —$N(R_7)(R_8)$; $C_1$–$C_{18}$haloalkyl; or halogen; or have one of the definitions of $OR_3$.

Preferred among the latter are compounds of formulae IIa and IIb

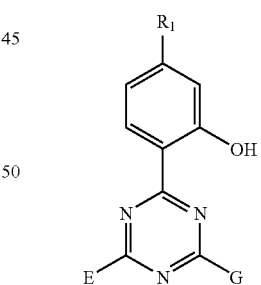

(IIa)

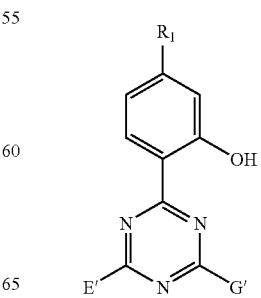

(IIb)

wherein
E corresponds to the formula

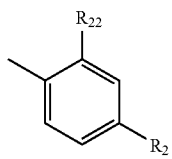

or G;
E' corresponds to the formula

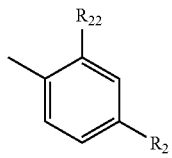

or G';
G corresponds to the formula

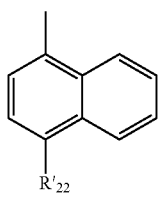

and G' corresponds to the formula

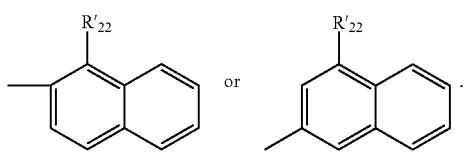

Especially preferred are compounds of formula I wherein
$R_1$ is hydrogen or $OR_3$;
$R_2$ is H, $C_1$–$C_8$alkyl; phenyl; phenyl substituted by methyl or by methoxy; NH—CO—$R_5$; trifluoromethyl; or $C_1$–$C_{18}$alkoxy;
$R_3$ is H, $C_1$–$C_{18}$alkyl; cyclohexyl; $C_3$–$C_{18}$alkenyl; $C_1$–$C_{18}$alkyl that is substituted by phenyl, OH, $C_1$–$C_{18}$alkoxy, cyclohexyloxy, halogen, —COOH, —COOR$_4$, —O—CO—$R_5$, —CO—NHR$_7$, —CO—N(R$_7$)(R$_8$), CN, NHR$_7$, —N(R$_7$)(R$_8$), —NH—CO—$R_5$ and/or by phenyl-$C_1$–$C_4$alkoxy; or cyclohexyl that is substituted by OH, $C_1$–$C_4$alkyl, $C_2$–$C_6$alkenyl or by —O—CO—$R_5$;
$R_4$ is $C_1$–$C_{18}$alkyl; $C_7$–$C_{11}$phenylalkyl; $C_5$–$C_{12}$cycloalkyl; or $C_2$–$C_{12}$hydroxyalkyl;
$R_5$ is H; $C_1$–$C_{18}$alkyl; $C_2$–$C_8$alkenyl; cyclohexyl; phenyl; or $C_7$–$C_{11}$phenylalkyl;
$R_7$ and $R_8$, independently of each other, are $C_3$–$C_{12}$alkyl or cyclohexyl; or together form $C_3$–$C_9$oxaalkylene; the radicals $R_{11}$, $R_{22}$ and $R_{33}$, independently of one another, are H, $C_7$–$C_{11}$phenylalkyl or $C_1$–$C_8$alkyl; and $R'_{22}$ and $R'_{33}$, independently of each other, are H; $C_1$–$C_8$alkyl; $C_3$–$C_6$alkenyl; $C_7$–$C_{11}$phenylalkyl; $C_5$–$C_{12}$cycloalkyl; trifluoromethyl; phenyl; naphthyl; biphenylyl; $C_7$–$C_{11}$phenylalkyl; $C_7$–$C_{14}$alkylphenyl; or NHR$_7$ or —N(R$_7$)(R$_8$); or have one of the definitions of $OR_3$.

Of particular significance are compounds of formulae IIa and IIb wherein
E in formula IIa corresponds to one of the formulae

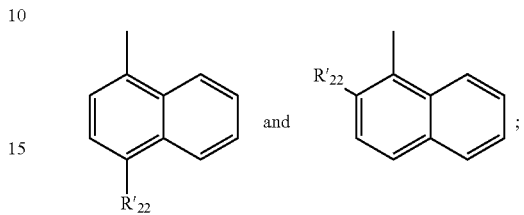

E in formula IIb corresponds to the formula

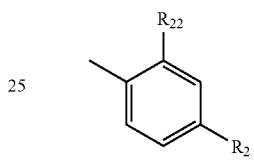

or G';
G corresponds to the formula

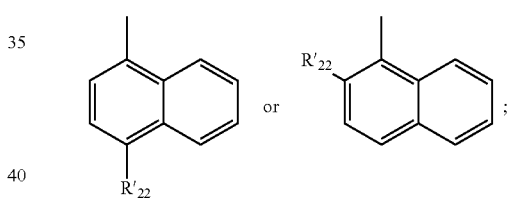

and G' corresponds to the formula

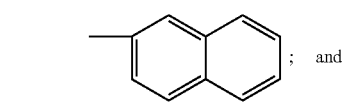

$R_1$ is hydrogen or $OR_3$;
$R_2$ is H, $C_1$–$C_8$alkyl; methoxy or phenyl;
$R_3$ is H, $C_1$–$C_{18}$alkyl; $C_1$–$C_{12}$alkyl that is substituted by OH, $C_1$–$C_{18}$alkoxy, COOR$_4$ or by —O—CO—$R_5$;
$R_4$ is $C_1$–$C_{18}$alkyl;
$R_5$ is H; $C_1$–$C_{18}$alkyl; or $C_7$–$C_{11}$phenylalkyl; and
$R_{22}$ is H or methyl; and
$R'_{22}$ is H or $C_1$–$C_4$alkyl or has one of the definitions of $OR_3$.

The compounds of formula I can be prepared by Friedel-Crafts addition of halotriazines to corresponding aromatic compounds and phenols analogously to one of the methods specified in EP-A-434 608 or in one of the publications mentioned at the beginning or analogously to one of the methods specified in the publication by H. Brunetti and C. E. Lüthi, Helv. Chim. Acta 55, 1566 (1972); see also U.S.

Pat. Nos. 5,726,310, 6,057,444, 6,225,468, and EP-A-941 989, WO 00/29392. That procedure can be followed by a further reaction according to known methods to form compounds of formula I wherein $R_7$ is not hydrogen; such reactions and processes are described, for example, in EP-A-434 608, page 15, line 11, to page 17, line 1. That route is especially suitable for the preparation of compounds according to the invention of formula I wherein the naphthyl group is bonded in the α-position (1-naphthyl).

To prepare the compounds of formula 1, advantageously one equivalent of cyanuric chloride is used as starting material and is reacted with approximately one equivalent each of naphthalene or a suitable naphthalene compound, a further aromatic compound and a phenol, such as, for example, resorcinol. Suitable aromatic starting materials must have at least one C—H bond on the aromatic compound; at least one of the phenols used must contain an ortho-position unsubstituted in that manner. The further aromatic compound may be identical to the naphthalene compound or the phenol, or may be benzene or a substituted benzene, such as, for example, toluene, xylene, mesitylene, tert-butylbenzene, biphenyl or methoxybenzene. The naphthalene compound is preferably naphthalene, or alkyl- or alkoxy-naphthalene, especially α- or β-naphthol, α- or β-methylnaphthalene, α- or β-methoxynaphthalene. The phenol is preferably phenol, resorcinol, or resorcinol substituted by alkyl or by phenylalkyl, especially resorcinol.

The reaction is carried out in a manner known per se by reacting the starting materials with the cyanuric halide in an inert solvent in the presence of anhydrous $AlC_{13}$. Aluminium trichloride can be used in excess and/or in admixture with HCl, for example conc. aqu. hydrochloric acid. Advantageously, the naphthyl compound is reacted first and the phenol compound is added last.

The reaction product of cyanuric halide and naphthyl compound can be further reacted directly or can also be isolated in known manner. A number of such intermediates are novel; the invention therefore relates also to the compounds 2,4-bis(4-methyl-1-naphthyl)-6-chloro-1,3,5-triazine;
2,4-bis(4-methoxy-1-naphthyl)-6-chloro-1,3,5-triazine;
2-(4-methoxy-1-naphthyl)-4-(4-hydroxy-1-naphthyl)-6-chloro-1,3,5-triazine;
2,4-bis(2-hydroxy-1-naphthyl)-6-chloro-1,3,5-triazine;
2,4-bis(2-methoxy-1-naphthyl)-6-chloro-1,3,5-triazine;
2-(2-methoxy-1-naphthyl)-4-(2-hydroxy-1-naphthyl)-6-chloro-1,3,5-triazine;
2,4-dichloro-6-(2-methoxy-1-naphthyl)-1,3,5-triazine.

Suitable solvents are, for example, hydrocarbons, chlorinated hydrocarbons, hydrocarbons containing SO or $SO_2$ groups, or nitrated aromatic hydrocarbons; high-boiling hydrocarbons, such as ligroin, petroleum ether, toluene or xylene, or sulfolane are preferred.

The temperature is generally not critical; the temperatures used are usually from −20° C. to the boiling point of the solvent, for example from 0° C. to 100° C.

Alternatively, the α- or β-naphthyltriazines according to the invention can also be prepared by means of Grignard processes analogously to known compounds, see U.S. Pat. No. 5,438,138 and publications mentioned therein.

The compounds according to the invention can furthermore be obtained analogously to processes described in U.S. Pat. No. 5,545,863, U.S. Pat. No. 5,478,935, U.S. Pat. No. 6,020,490, WO 96/28431, or by ring-closing reactions analogously to H. Brunetti and C. E. Lüthi, Helv. Chim. Acta 55, 1566 (1972). For example, compounds according to the invention of formula I can be obtained analogously to WO 96/28431 by replacing one or also both of the biphenyl starting compounds described in WO 96/28431 on pages 9–13 by a corresponding naphthyl compound in each case.

Free phenolic hydroxyl groups of the reaction product in the p-position with respect to the triazine ring can be further modified in known manner, for example etherified. Working-up can be carried out by customary methods, e.g. by extraction and separation steps, filtration and drying; if necessary, further purification steps can be performed, e.g. recrystallisation.

The products from the above-described reactions can be further modified within the scope of the definitions given for formula I according to known methods.

The reactions can be carried out with the exclusion of oxygen, for example by flushing with an inert gas, such as argon; oxygen is not troublesome in every case, however, and therefore the reaction can also be carried without the mentioned measure. When the reaction is complete, working-up can be carried out according to customary methods.

The compounds according to the invention are especially suitable for stabilizing organic materials against damage by light, oxygen or heat. The compounds according to the invention are most especially suitable as light stabilisers (UV absorbers).

The materials to be stabilised may be e.g. oils, fats, waxes, surface-coatings, cosmetics, photographic materials, textiles and their dyestuffs, or biocides. A particularly interesting application is in polymeric materials of the kind present in plastics materials, rubbers, coating materials, photographic material or adhesives. When used in cosmetic preparations, the skin or hair to which the preparation is applied is especially also protected against damage by light.

Examples of organic materials that can be stabilised in that manner are as follows:

1. Polymers of monoolefins and diolefins, for example polypropylene, polyisobutylene, polybut-1-ene, poly-4-methylpent-1-ene, polyvinylcyclohexane, polyisoprene or polybutadiene, as well as polymers of cycloolefins, for instance of cyclopentene or norbornene, polyethylene (which optionally can be crosslinked), for example high density polyethylene (HDPE), high density and high molecular weight polyethylene (HDPE-HMW), high density and ultrahigh molecular weight polyethylene (HDPE-UHMW), medium density polyethylene (MDPE), low density polyethylene (LDPE), linear low density polyethylene (LLDPE), (VLDPE) and (ULDPE).

Polyolefins, i.e. the polymers of monoolefins exemplified in the preceding paragraph, preferably polyethylene and polypropylene, can be prepared by different, and especially by the following, methods:

a) radical polymerisation (normally under high pressure and at elevated temperature).

b) catalytic polymerisation using a catalyst that normally contains one or more than one metal of groups IVb, Vb, VIb or VIII of the Periodic Table. These metals usually have one or more than one ligand, typically oxides, halides, alcoholates, esters, ethers, amines, alkyls, alkenyls and/or aryls that may be either π- or σ-coordinated. These metal complexes may be in the free form or fixed on substrates, typically on activated magnesium chloride, titanium(III) chloride, alumina or silicon oxide. These catalysts may be soluble or insoluble in the polymerisation medium. The catalysts can be used by themselves in the polymerisation or further activators may be used, typically metal alkyls, metal hydrides, metal alkyl halides, metal alkyl oxides or metal alkyloxanes, said metals being elements of groups Ia, Ia and/or IIIa of the Periodic Table. The activators may be modified conveniently with further ester, ether, amine or silyl ether groups. These catalyst systems are usually termed Phillips, Standard Oil Indiana, Ziegler (-Natta), TNZ (DuPont), metallocene or single site catalysts (SSC).

2. Mixtures of the polymers mentioned under 1), for example mixtures of polypropylene with polyisobutylene, polypropylene with polyethylene (for example PP/HDPE, PP/LDPE) and mixtures of different types of polyethylene (for example LDPE/HDPE).

3. Copolymers of monoolefins and diolefins with each other or with other vinyl monomers, for example ethylene/propylene copolymers, linear low density polyethylene (LLDPE) and mixtures thereof with low density polyethylene (LDPE), propylene/but-1-ene copolymers, propylene/isobutylene copolymers, ethylene/but-1-ene copolymers, ethylene/hexene copolymers, ethylene/methylpentene copolymers, ethylene/heptene copolymers, ethylene/octene copolymers, ethylene/vinylcyclohexane copolymers, ethylene/cycloolefin copolymers (e.g. ethylene/norbornene like COC), ethylene/1-olefins copolymers, where the 1-olefin is generated in-situ; propylene/butadiene copolymers, isobutylenelisoprene copolymers, ethylene/vinylcyclohexene copolymers, ethylene/alkyl acrylate copolymers, ethylene/alkyl methacrylate copolymers, ethylene/vinyl acetate copolymers or ethylene/acrylic acid copolymers and their salts (ionomers) as well as terpolymers of ethylene with propylene and a diene such as hexadiene, dicyclopentadiene or ethylidene-norbornene; and mixtures of such copolymers with one another and with polymers mentioned in 1) above, for example polypropylene/ethylene-propylene copolymers, LDPE/ethylene-vinyl acetate copolymers (EVA), LDPE/ethyleneacrylic acid copolymers (EAA), LLDPE/EVA, LLDPE/EAA and alternating or random polyalkylene/carbon monoxide copolymers and mixtures thereof with other polymers, for example polyamides.

4. Hydrocarbon resins (for example $C_5$–$C_9$) including hydrogenated modifications thereof (e.g. tackifiers) and mixtures of polyalkylenes and starch.

Homopolymers and copolymers from 1.)–4.) may have any stereostructure including syndiotactic, isotactic, hemi-isotactic or atactic; where atactic polymers are preferred. Stereoblock polymers are also included.

5. Polystyrene, poly(p-methylstyrene), poly(α-methylstyrene).

6. Aromatic homopolymers and copolymers derived from vinyl aromatic monomers including styrene, α-methylstyrene, all isomers of vinyl toluene, especially p-vinyltoluene, all isomers of ethyl styrene, propyl styrene, vinyl biphenyl, vinyl naphthalene, and vinyl anthracene, and mixtures thereof. Homopolymers and copolymers may have any stereostructure including syndiotactic, isotactic, hemi-isotactic or atactic; where atactic polymers are preferred. Stereoblock polymers are also included.

6a. Copolymers including aforementioned vinyl aromatic monomers and comonomers selected from ethylene, propylene, dienes, nitriles, acids, maleic anhydrides, maleimides, vinyl acetate and vinyl chloride or acrylic derivatives and mixtures thereof, for example styrene/butadiene, styrene/acrylonitrile, styrene/ethylene (interpolymers), styrene/alkyl methacrylate, styrene/butadiene/alkyl acrylate, styrene/butadiene/alkyl methacrylate, styrene/maleic anhydride, styrene/acrylonitrile/methyl acrylate; mixtures of high impact strength of styrene copolymers and another polymer, for example a polyacrylate, a diene polymer or an ethylene/propylene/diene terpolymer; and block copolymers of styrene such as styrene/butadiene/styrene, styrenelisoprene/styrene, styrene/ethylene/butylene/styrene or styrene/ethylene/propylene/styrene.

6b. Hydrogenated aromatic polymers derived from hydrogenation of polymers mentioned under 6.), especially including polycyclohexylethylene (PCHE) prepared by hydrogenating atactic polystyrene, often referred to as polyvinylcyclohexane (PVCH).

6c. Hydrogenated aromatic polymers derived from hydrogenation of polymers mentioned under 6a.).

Homopolymers and copolymers may have any stereostructure including syndiotactic, isotactic, hemi-isotactic or atactic; where atactic polymers are preferred. Stereoblock polymers are also included.

7. Graft copolymers of vinyl aromatic monomers such as styrene or α-methylstyrene, for example styrene on polybutadiene, styrene on polybutadiene-styrene or polybutadiene-acrylonitrile copolymers; styrene and acrylonitrile (or methacrylonitrile) on polybutadiene; styrene, acrylonitrile and methyl methacrylate on polybutadiene; styrene and maleic anhydride on polybutadiene; styrene, acrylonitrile and maleic anhydride or maleimide on polybutadiene; styrene and maleimide on polybutadiene; styrene and alkyl acrylates or methacrylates on polybutadiene; styrene and acrylonitrile on ethylene/propylene/diene terpolymers; styrene and acrylonitrile on polyalkyl acrylates or polyalkyl methacrylates, styrene and acrylonitrile on acrylate/butadiene copolymers, as well as mixtures thereof with the copolymers listed under 6), for example the copolymer mixtures known as ABS, MBS, ASA or AES polymers.

8. Halogen-containing polymers such as polychloroprene, chlorinated rubbers, chlorinated and brominated copolymer of isobutylene-isoprene (halobutyl rubber), chlorinated or sulfochlorinated polyethylene, copolymers of ethylene and chlorinated ethylene, epichlorohydrin homo- and copolymers, especially polymers of halogen-containing vinyl compounds, for example polyvinyl chloride, polyvinylidene chloride, polyvinyl fluoride, polyvinylidene fluoride, as well as copolymers thereof such as vinyl chloride/vinylidene chloride, vinyl chloride/vinyl acetate or vinylidene chloride/vinyl acetate copolymers.

9. Polymers derived from α,β-unsaturated acids and derivatives thereof such as polyacrylates and polymethacrylates; polymethyl methacrylates, polyacrylamides and polyacrylonitriles, impact-modified with butyl acrylate.

10. Copolymers of the monomers mentioned under 9) with each other or with other unsaturated monomers, for example acrylonitrile/ butadiene copolymers, acrylonitrile/alkyl acrylate copolymers, acrylonitrile/alkoxyalkyl acrylate or acrylonitrile/vinyl halide copolymers or acrylonitrile/alkyl methacrylate/butadiene terpolymers.

11. Polymers derived from unsaturated alcohols and amines or the acyl derivatives or acetals thereof, for example polyvinyl alcohol, polyvinyl acetate, polyvinyl stearate, polyvinyl benzoate, polyvinyl maleate, polyvinyl butyral, polyallyl phthalate or polyallyl melamine; as well as their copolymers with olefins mentioned in 1) above.

12. Homopolymers and copolymers of cyclic ethers such as polyalkylene glycols, polyethylene oxide, polypropylene oxide or copolymers thereof with bisglycidyl ethers.

13. Polyacetals such as polyoxymethylene and those polyoxymethylenes which contain ethylene oxide as a comonomer; polyacetals modified with thermoplastic polyurethanes, acrylates or MBS.

14. Polyphenylene oxides and sulfides, and mixtures of polyphenylene oxides with styrene polymers or polyamides.

15. Polyurethanes derived from hydroxyl-terminated polyethers, polyesters or polybutadienes on the one hand and aliphatic or aromatic polyisocyanates on the other, as well as precursors thereof.

16. Polyamides and copolyamides derived from diamines and dicarboxylic acids and/or from aminocarboxylic acids or the corresponding lactams, for example polyamide 4, polyamide 6, polyamide 6/6, 6/10, 6/9, 6/12, 4/6, 12/12, polyamide 11, polyamide 12, aromatic polyamides starting from m-xylene diamine and adipic acid; polyamides prepared from hexamethylenediamine and isophthalic or/and terephthalic acid and with or without an elastomer as modifier, for example poly-2,4,4-trimethylhexamethylene terephthalamide or poly-m-phenylene isophthalamide; and also block copolymers of the aforementioned polyamides with polyolefins, olefin copolymers, ionomers or chemically bonded or grafted elastomers; or with polyethers, e.g. with polyethylene glycol, polypropylene glycol or polytetramethylene glycol; as well as polyamides or copolyamides modified with EPDM or ABS; and polyamides condensed during processing (RIM polyamide systems).

17. Polyureas, polyimides, polyamide-imides, polyetherimids, polyesterimids, polyhydantoins and polybenzimidazoles.

18. Polyesters derived from dicarboxylic acids and diols and/or from hydroxycarboxylic acids or the corresponding lactones, for example polyethylene terephthalate, polybutylene terephthalate, poly-1,4-dimethylolcyclohexane terephthalate, polyalkylene naphthalate (PAN) and polyhydroxybenzoates, as well as block copolyether esters derived from hydroxyl-terminated polyethers; and also polyesters modified with polycarbonates or MBS.

19. Polycarbonates and polyester carbonates.

20. Polyketones.

21. Polysulfones, polyether sulfones and polyether ketones.

22. Crosslinked polymers derived from aldehydes on the one hand and phenols, ureas and melamines on the other hand, such as phenol/formaldehyde resins, urea/formaldehyde resins and melamine/formaldehyde resins.

23. Drying and non-drying alkyd resins.

24. Unsaturated polyester resins derived from copolyesters of saturated and unsaturated dicarboxylic acids with polyhydric alcohols and vinyl compounds as crosslinking agents, and also halogen-containing modifications thereof of low flammability.

25. Crosslinkable acrylic resins derived from substituted acrylates, for example epoxy acrylates, urethane acrylates or polyester acrylates.

26. Alkyd resins, polyester resins and acrylate resins crosslinked with melamine resins, urea resins, isocyanates, isocyanurates, polyisocyanates or epoxy resins.

27. Crosslinked epoxy resins derived from aliphatic, cycloaliphatic, heterocyclic or aromatic glycidyl compounds, e.g. products of diglycidyl ethers of bisphenol A and bisphenol F, which are crosslinked with customary hardeners such as anhydrides or amines, with or without accelerators.

28. Natural polymers such as cellulose, rubber, gelatin and chemically modified homologous derivatives thereof, for example cellulose acetates, cellulose propionates and cellulose butyrates, or the cellulose ethers such as methyl cellulose; as well as rosins and their derivatives.

29. Blends of the aforementioned polymers (polyblends), for example PP/EPDM, Polyamide/EPDM or ABS, PVC/EVA, PVC/ABS, PVC/MBS, PC/ABS, PBTP/ABS, PC/ASA, PC/PBT, PVC/CPE, PVC/acrylates, POM/thermoplastic PUR, PC/thermoplastic PUR, POM/acrylate, POM/MBS, PPO/HIPS, PPO/PA 6.6 and copolymers, PA/HDPE, PA/PP, PA/PPO, PBT/PC/ABS or PBT/PET/PC.

The invention further relates therefore to a composition comprising A) an organic material that is sensitive to oxidative, thermal or/and actinic degradation/formation and B) as stabiliser at least one compound of formula 1, and to the use of compounds of formula I for stabilizing organic material against oxidative, thermal or actinic degradation/formation.

The invention also includes a method of stabilizing organic material against thermal, oxidative or/and actinic degradation/formation, which comprises applying or adding at least one compound of formula I to that material.

The amount of the stabiliser to be used depends upon the organic material to be stabilised and upon the intended use of the stabilised material. In general, the composition according to the invention comprises from 0.01 to 15, especially from 0.05 to 10, and more especially from 0.1 to 5, parts by weight of stabiliser (component B) per 100 parts by weight of component A. The stabiliser (component B) may be a single compound of formula I or also a mixture.

In addition to the compounds of formula 1, the compositions according to the invention may comprise as additional component (C) one or more conventional additives, such as, for example, antioxidants, further light stabilisers, metal deactivators, phosphites or phosphonites. Examples of these are as follows:

1. Antioxidants 1.1. Alkylated monophenols, for example 2,6-di-tert-butyl-4-methylphenol, 2-tert-butyl-4,6-dimethylphenol, 2,6-di-tert-butyl-4-ethylphenol, 2,6-di-tert-butyl-4-n-butylphenol, 2,6-di-tert-butyl-4-isobutylphenol, 2,6-dicyclopentyl-4-methylphenol, 2-($\alpha$-methylcyclohexyl)-4,6-dimethylphenol, 2,6-dioctadecyl-4-methylphenol, 2,4,6-tricyclohexylphenol, 2,6-di-tert-butyl-4-methoxymethylphenol, nonylphenols which are linear or branched in the side chains, for example 2,6-di-nonyl-4-methylphenol, 2,4-dimethyl-6-(1'-methylundec-1'-yl)phenol, 2,4-dimethyl-6-(1'-methylheptadec-1'-yl)phenol, 2,4-dimethyl-6-(1'-methyltridec-1'-yl)phenol and mixtures thereof.

1.2. Alkylthiomethylphenols, for example 2,4-dioctylthiomethyl-6-tert-butylphenol, 2,4-dioctylthiomethyl-6-methylphenol, 2,4-dioctylthiomethyl-6-ethylphenol, 2,6-di-dodecylthiomethyl-4-nonylphenol.

1.3. Hydroquinones and alkylated hydroquinones, for example 2,6-di-tert-butyl-4-methoxyphenol, 2,5-di-tert-butylhydroquinone, 2,5-di-tert-amylhydroquinone, 2,6-diphenyl-4-octadecyloxyphenol, 2,6-di-tert-butylhydroquinone, 2,5-di-tert-butyl-4-hydroxyanisole, 3,5-di-tert-butyl-4-hydroxyanisole, 3,5-di-tert-butyl-4-hydroxyphenyl stearate, bis(3,5-di-tert-butyl-4-hydroxyphenyl) adipate.

1.4. Toconherols, for example $\alpha$-tocopherol, $\beta$-tocopherol, $\gamma$-tocopherol, $\delta$-tocopherol and mixtures thereof (vitamin E).

1.5. Hydroxvlated thiodiphenyl ethers, for example 2,2'-thiobis(6-tert-butyl-4-methylphenol), 2,2'-thiobis(4-octylphenol), 4,4'-thiobis(6-tert-butyl-3-methylphenol), 4,4'-thiobis(6-tert-butyl-2-methylphenol), 4,4'-thiobis(3,6-di-sec-amylphenol), 4,4'-bis(2,6-dimethyl-4-hydroxyphenyl)-disulfide.

1.6. Alkylidenebisphenols, for example 2,2'-methylenebis(6-tert-butyl-4-methylphenol), 2,2'-methylenebis(6-tert-butyl-4-ethylphenol), 2,2'-methylenebis[4-methyl-6-($\alpha$-methylcyclohexyl)-phenol], 2,2'-methylenebis(4-methyl-6-cyclohexylphenol), 2,2'-methylenebis(6-nonyl-4- methylphenol), 2,2'-methylenebis(4,6-di-tert-butylphenol), 2,2'-ethylidenebis(4,6-di-tert-butylphenol), 2,2'-ethylidenebis(6-tert-butyl-4-isobutylphenol), 2,2'-methylenebis[6-(α-methylbenzyl)-4-nonylphenol], 2,2'-methylenebis[6-(α,α-dimethylbenzyl)-4-nonylphenol], 4,4'-methylenebis(2,6-di-tert-butylphenol), 4,4'-methylenebis(6-tert-butyl-2-methylphenol), 1,1-bis(5-tertbutyl-4-hydroxy-2-methylphenyl)butane, 2,6-bis(3-tert-butyl-5-methyl-2-hydroxybenzyl)-4-methylphenol, 1,1,3-tris(5-tert-butyl-4-hydroxy-2-methylphenyl)butane, 1,1-bis(5-tert-butyl-4-hydroxy-2-methylphenyl)-3-n-dodecylmercaptobutane, ethylene glycol bis[3,3-bis(3'-tertbutyl-4'-hydroxyphenyl) butyrate], bis(3-tert-butyl-4-hydroxy-5-methyl-phenyl)dicyclopentadiene, bis[2-(3'-tert-butyl-2'-hydroxy-5'-methylbenzyl)-6-tert-butyl-4-methylphenyl]terephthalate, 1,1-bis-(3,5-dimethyl-2-hydroxyphenyl)butane, 2,2-bis(3,5-di-tert-butyl-4-hydroxyphenyl)propane, 2,2-bis-(5-tert-butyl-4-hydroxy2-methylphenyl)-4-n-dodecylmercaptobutane, 1,1,5,5-tetra(5-tert-butyl-4-hydroxy-2-methylphenyl)pentane.

1.7. O—, N— and S-benzyl compounds, for example 3,5,3',5'-tetra-tert-butyl-4,4'-dihydroxydlbenzyl ether, octadecyl-4-hydroxy-3,5-dimethylbenzylmercaptoacetate, tridecyl-4-hydroxy-3,5-di-tert-butylbenzylmercaptoacetate, tris(3,5-di-tert-butyl-4-hydroxybenzyl)amine, bis(4-tert-butyl-3-hydroxy-2,6-dimethylbenzyl)dithioterephthalate, bis(3,5-di-tert-butyl-4-hydroxybenzyl)sulfide, isooctyl-3,5-di-tert-butyl-4-hydroxybenzylmercaptoacetate.

1.8. Hydroxybenzylated malonates, for example dioctadecyl-2,2-bis(3,5-di-tert-butyl-2-hydroxybenzyl)malonate, di-octadecyl-2-(3-tert-butyl-4-hydroxy-5-methylbenzyl)malonate, didodecylmercaptoethyl-2,2-bis(3,5-di-tert-butyl-4-hydroxybenzyl)malonate, bis[4-(1,1,3,3-tetramethylbutyl) phenyl]-2,2-bis(3,5-di-tert-butyl-4-hydroxybenzyl) malonate.

1.9. Aromatic hydroxybenzyl compounds, for example 1,3,5-tris(3,5-di-tert-butyl-4-hydroxybenzyl)-2,4,6-trimethylbenzene, 1,4-bis(3,5-di-tert-butyl-4-hydroxybenzyl)-2,3,5,6-tetramethylbenzene, 2,4,6-tris(3,5-di-tert-butyl-4-hydroxybenzyl)phenol.

1.10. Triazine compounds, for example 2,4-bis(octylmercapto)-6-(3,5-di-tert-butyl-4-hydroxyanilino)-1,3,5-triazine, 2-octylmercapto-4,6-bis(3,5-di-tert-butyl-4-hydroxyanilino)-1,3,5-triazine, 2-octylmercapto-4,6-bis(3,5-di-tert-butyl-4-hydroxyphenoxy)-1,3,5-triazine, 2,4,6-tris(3,5-di-tert-butyl-4-hydroxyphenoxy)-1,2,3-triazine, 1,3,5-tris(3,5-di-tert-butyl-4-hydroxybenzyl)isocyanurate, 1,3,5-tris(4-tert-butyl-3-hydroxy-2,6-dimethylbenzyl)isocyanurate, 2,4,6-tris-(3,5-di-tert-butyl-4-hydroxyphenylethyl)-1,3,5-triazine, 1,3,5-tris(3,5-di-tert-butyl-4-hydroxyphenylpropionyl)-hexahydro-1,3,5-triazine, 1,3,5-tris(3,5-dicyclohexyl-4-hydroxybenzyl)isocyanurate.

1.11. Benzylohosphonates, for example dimethyl-2,5-di-tert-butyl-4-hydroxybenzylphosphonate, diethyl-3,5-di-tert-butyl-4-hydroxybenzylphosphonate, dioctadecyl3,5-di-tert-butyl-4-hydroxybenzylphosphonate, dioctadecyl-5-tert-butyl-4-hydroxy-3-methylbenzylphosphonate, the calcium salt of the monoethyl ester of 3,5-di-tert-butyl-4-hydroxybenzylphosphonic acid.

1.12. Acylaminophenols, for example 4-hydroxylauranilide, 4-hydroxystearanilide, octyl N-(3,5-di-tert-butyl-4-hydroxyphenyl)carbamate.

1.13. Esters of β-(3,5-di-tert-butyl-4-hydroxnohenyl)progionic acid with mono- or polyhydric alcohols, e.g. with methanol, ethanol, n-octanol, i-octanol, octadecanol, 1,6-hexanediol, 1,9-nonanediol, ethylene glycol, 1,2-propanediol, neopentyl glycol, thiodiethylene glycol, diethylene glycol, triethylene glycol, pentaerythritol, tris(hydroxyethyl)isocyanurate, N,N'-bis(hydroxyethyl) oxamide, 3-thiaundecanol, 3-thiapentadecanol, trimethylhexanediol, trimethylolpropane, 4-hydroxymethyl-1-phospha-2,6,7-trioxabicyclo[2.2.2]octane.

1.14. Esters of β-(5-tert-butyl-4-hydroxy-3-methylphenyl)propionic acid with mono- or polyhydric alcohols, e.g. with methanol, ethanol, n-octanol, i-octanol, octadecanol, 1,6-hexanediol, 1,9-nonanediol, ethylene glycol, 1,2-propanediol, neopentyl glycol, thiodiethylene glycol, diethylene glycol, triethylene glycol, pentaerythritol, tris(hydroxyethyl)isocyanurate, N,N'-bis(hydroxyethyl)oxamide, 3-thiaundecanol, 3-thiapentadecanol, trimethylhexanediol, trimethylolpropane, 4-hydroxymethyl-1-phospha-2,6,7-trioxabicyclo[2.2.2]octane; 3,9-bis[2-{3-(3-tert-butyl-4-hydroxy-5-methylphenyl)propionyloxy}-1,1-dimethylethyl]-2,4,8,10-tetraoxaspiro[5.5]-unde 1.15. Esters of β-(3.5-dicyclohexyl-4-hydroxyphenyl) propionic acid with mono- or polyhydric alcohols, e.g. with methanol, ethanol, octanol, octadecanol, 1,6-hexanediol, 1,9-nonanediol, ethylene glycol, 1,2-propanediol, neopentyl glycol, thiodiethylene glycol, diethylene glycol, triethylene glycol, pentaerythritol, tris(hydroxyethyl)isocyanurate, N,N'-bis(hydroxyethyl)oxamide, 3-thiaundecanol, 3-thiapentadecanol, trimethylhexanediol, trimethylolpropane, 4-hydroxymethyl-1-phospha-2,6,7-trioxabicyclo[2.2.2]octane.

1.16. Esters of 3.5-di-tert-butyl-4-hydroxyphenyl acetic acid with mono- or polyhydric alcohols, e.g. with methanol, ethanol, octanol, octadecanol, 1,6-hexanediol, 1,9-nonanediol, ethylene glycol, 1,2-propanediol, neopentyl glycol, thiodiethylene glycol, diethylene glycol, triethylene glycol, pentaerythritol, tris(hydroxyethyl)isocyanurate, N,N'-bis(hydroxyethyl)oxamide, 3-thiaundecanol, 3-thiapentadecanol, trimethylhexanediol, trimethylolpropane, 4-hydroxymethyl-1-phospha-2,6,7-trioxabicyclo[2.2.2]octane.

1.17. Amides of β-(3,5-di-tert-butyl-4-hydroxyphenyl) propionic acid e.g. N,N'-bis(3,5-di-tert-butyl-4-hydroxyphenylpropionyl)hexamethylenediamide, N,N'-bis(3,5-di-tert-butyl-4-hydroxyphenylpropionyl)trimethylenediamide, N,N'-bis(3,5-di-tert-butyl-4-hydroxyphenylpropionyl)hydrazide, N,N'-bis[2-(3-[3,5-di-tert-butyl-4-hydroxyphenyl]propionyloxy)ethyl]oxamide (Naugard®XL-1, supplied by Uniroyal).

1.18. Ascorbic acid (vitamin C)

1.19. Aminic antioxidants, for example N,N'-di-isopropyl-p-phenylenediamine, N,N'-di-sec-butyl-p-phenylenediamine, N,N'-bis(1,4-dimethylpentyl)-p-phenylenediamine, N,N'-bis(1-ethyl-3-methylpentyl)-p-phenylenediamine, N,N'-bis(1-methylheptyl)-p-phenylenediamine, N,N'-dicyclohexyl-p-phenylenediamine, N,N'-diphenyl-p-phenylenediamine, N,N'-bis(2-naphthyl)-p-phenylenediamine, N-isopropyl—N'-phenyl-p-phenylenediamine, N-(1,3-dimethylbutyl)-N'-phenyl-p-phenylenediamine, N-(1-methylheptyl)-N'-phenyl-p-phenylenediamine, N-cyclohexyl-N'-phenyl-p-phenylenediamine, 4-(p-toluenesulfamoyl)diphenylamine, N,N'-dimethyl-N,N'-di-sec-butyl-p-phenylenediamine, diphenylamine, N-allyidiphenylamine, 4-isopropoxy-diphenylamine, N-phenyl-1-naphthylamine, N-(4-tert-octylphenyl)-1-naphthylamine, N-phenyl-2-naphthylamine, octylated diphenylamine, for example p,p'-di-tert-octyldiphenylamine, 4-n-butylaminophenol, 4-butyrylaminophenol, 4-nonanoylaminophenol, 4-dodecanoylaminophenol, 4-octadecanoylaminophenol, bis(4-methoxyphenyl)amine, 2,6-di-tert-butyl-4-dimethylaminomethylphenol, 2,4'-diaminodiphenylmethane, 4,4'-diaminodiphenylmethane, N,N,N',N'-tetramethyl-4,4'-diaminodiphenylmethane, 1,2-bis[(2-methylphenyl)amino]ethane, 1,2-bis(phenylamino)propane, (o-tolyl)biguanide, bis[4-(1',3'-dimethylbutyl)phenyl]amine, tert-octylated N-phenyl-1-naphthylamine, a mixture of mono- and dialkylated tert-butyl/tert-octyldiphenylamines, a mixture of mono- and dialkylated nonyldiphenylamines, a mixture of mono- and dialkylated dodecyldiphenylamines, a mixture of mono- and dialkylated isopropyl/isohexyldiphenylamines, a mixture of mono- and dialkylated tert-butyldiphenylamines, 2,3-dihydro-3,3-dimethyl-4H-1,4-benzothiazine, phenothiazine, a mixture of mono- and dialkylated tert-butyl/tert-octylphenothiazines, a mixture of mono- and dialkylated tert-octyl-phenothiazines, N-allylphenothiazine, N,N,N',N'-tetraphenyl-1,4-diaminobut-2-ene, N,N-bis-(2,2,6,6-tetramethyl-piperid-4-yl-hexamethylenediamine, bis(2,2,6,6-tetramethylpiperid-4-yl)-sebacate, 2,2,6,6-tetramethylpiperidin-4-one, 2,2,6,6-tetramethylpiperidin-4-ol.

2. UV absorbers and light stabilisers 2.1.2-(2'-Hydroxyhenyl)benzotriazoles, for example 2-(2'-hydroxy-5'-methylphenyl)benzotriazole, 2-(3',5'-di-tert-butyl-2'-hydroxyphenyl)benzotriazole, 2-(5'-tert-butyl-2'-hydroxyphenyl)benzotriazole, 2-(2'-hydroxy-5'-(1,1,3,3-tetramethylbutyl)phenyl)benzotriazole, 2-(3',5'-di-tert-butyl-2'-hydroxyphenyl)-5-chlorobenzotriazole, 2-(3'-tert-butyl-2'-hydroxy-5'-methylphenyl)-5-chlorobenzotriazole, 2-(3'-sec-butyl-5'-tert-butyl-2'-hydroxyphenyl)benzotriazole, 2-(2'-hydroxy-4'-octyloxyphenyl)benzotriazole, 2-(3',5'-di-tert-amyl-2'-hydroxyphenyl)benzotriazole, 2-(3',5'-bis(α,α-dimethylbenzyl)-2'-hydroxyphenyl)benzotriazole, ²-(3'-tert-butyl-2'-hydroxy-5'-(2-octyloxycarbonylethyl)phenyl)-5-chlorobenzotriazole, 2-(3'-tert-butyl-5'-[2-(2-ethylhexyloxy)carbonylethyl]-2'-hydroxyphenyl)-5-chlorobenzotriazole, 2-(3'-tert-butyl-2'-hydroxy-5'-(2-methoxycarbonylethyl)phenyl)-5-chlorobenzotriazole, 2-(3'-tert-butyl-2'-hydroxy-5'-(2-methoxycarbonylethyl)phenyl)benzotriazole, 2-(3'-tert-butyl-2'-hydroxy-5'-(2-octyloxycarbonylethyl)phenyl)benzotriazole, 2-(3'-tert-butyl-5'-[2-(2-ethylhexyloxy)carbonylethyl]-2'-hydroxyphenyl)benzotriazole, 2-(3'-dodecyl-2'-hydroxy-5'-methylphenyl)benzotriazole, 2-(3'-tert-butyl-2'-hydroxy-5'-(2-isooctyloxycarbonylethyl)phenylbenzotriazole, 2,2'-methylenebis[4-(1,1,3,3-tetramethylbutyl)-6-benzotriazole-2-ylphenol]; the transesterification product of 2-[3'-tert-butyl-5'-(2-methoxycarbonylethyl)-2'-hydroxyphenyl]-2H-benzotriazole with polyethylene glycol 300; [R—CH$_2$CH$_2$—COO—CH$_2$CH$_2$—]$_2$, where R=3'-tert-butyl-4'-hydroxy-5'-2H-benzotriazol-2-ylphenyl, 2-[2'-hydroxy-3'-(α,α-dimethylbenzyl)-5'-(1,1,3,3-tetramethylbutyl)phenyl]-benzotriazole; 2-[2'-hydroxy-3'-(1,1,3,3-tetramethylbutyl)-5'-(α,α-dimethylbenzyl)phenyl]benzotriazole.

2.2.2-Hydroxybenzophenones, for example the 4-hydroxy, 4-methoxy, 4-octyloxy, 4-decyloxy, 4-dodecyloxy, 4-benzyloxy, 4,2',4'-trihydroxy and 2'-hydroxy-4,4'-dimethoxy derivatives.

2.3. Esters of substituted and unsubstituted benzoic acids, for example 4-tert-butylphenyl salicylate, phenyl salicylate, octylphenyl salicylate, dibenzoyl resorcinol, bis(4-tert-butylbenzoyl)resorcinol, benzoyl resorcinol, 2,4-di-tert-butylphenyl 3,5-di-tert-butyl-4-hydroxybenzoate, hexadecyl 3,5-di-tert-butyl-4-hydroxybenzoate, octadecyl 3,5-di-tert-butyl-4-hydroxybenzoate, 2-methyl-4,6-di-tert-butylphenyl 3,5-di-tert-butyl-4-hydroxybenzoate.

2.4. Acrylates, for example ethyl α-cyano-β,β-diphenylacrylate, isooctyl α-cyano-β,β-diphenylacrylate, methyl α-carbomethoxycinnamate, methyl α-cyano-β-methyl-p-methoxycinnamate, butyl α-cyano-β-methyl-p-methoxycinnamate, methyl α-carbomethoxy-p-methoxycinnamate and N-(β-carbomethoxy-β-cyanovinyl)-2-methylindoline.

2.5. Nickel compounds, for example nickel complexes of 2,2'-thiobis[4-(1,1,3,3-tetramethylbutyl)phenol], such as the 1:1 or 1:2 complex, with or without additional ligands such as n-butylamine, triethanolamine or N-cyclohexyldiethanolamine, nickel dibutyldithiocarbamate, nickel salts of the monoalkyl esters, e.g. the methyl or ethyl ester, of 4-hydroxy-3,5-di-tert-butylbenzylphosphonic acid, nickel complexes of ketoximes, e.g. of 2-hydroxy-4-methylphenylundecylketoxime, nickel complexes of 1-phenyl-4-lauroyl-5-hydroxypyrazole, with or without additional ligands.

2.6. Sterically hindered amines, for example bis(2,2,6,6-tetramethyl-4-piperidyl)sebacate, bis(2,2,6,6-tetramethyl-4-piperidyl)succinate, bis(1,2,2,6,6-pentamethyl-4-piperidyl)sebacate, bis(1-octyloxy-2,2,6,6-tetramethyl-4-piperidyl)sebacate, bis(1,2,2,6,6-pentamethyl-4-piperidyl) n-butyl-3,5-di-tert-butyl-4-hydroxybenzylmalonate, the condensate of 1-(2-hydroxyethyl)-2,2,6,6-tetramethyl-4-hydroxypiperidine and succinic acid, linear or cyclic condensates of N,N'-bis(2,2,6,6-tetramethyl-4-piperidyl)hexamethylenediamine and 4-tert-octylamino-2,6-dichloro-1,3,5-triazine, tris(2,2,6,6-tetramethyl-4-piperidyl)nitrilotriacetate, tetrakis(2,2,6,6-tetramethyl-4-piperidyl)-1,2,3,4-butanetetracarboxylate, 1,1'-(1,2-ethanediyl)-bis(3,3,5,5-tetramethylpiperazinone), 4-benzoyl-2,2,6,6-tetramethylpiperidine, 4-stearyloxy-2,2,6,6-tetramethylpiperidine, bis(1,2,2,6,6-pentamethylpiperidyl)-2-n-butyl-2-(2-hydroxy-3,5-di-tert-butylbenzyl)malonate, 3-n-octyl-7,7,9,9-tetramethyl-1,3,8-triazaspiro[4.5]decane-2,4-dione, bis(1-octyloxy-2,2,6,6-tetramethylpiperidyl)sebacate, bis(1-octyloxy-2,2,6,6-tetramethylpiperidyl)succinate, linear or cyclic condensates of N,N'-bis(2,2,6,6-tetramethyl-4-piperidyl)hexamethylenediamine and 4-morpholino-2,6-dichloro-1,3,5-triazine, the condensate of 2-chloro-4,6-bis(4-n-butylamino-2,2,6,6-tetramethylpiperidyl)-1,3,5-triazine and 1,2-bis(3-aminopropylamino)ethane, the condensate of 2-chloro-4,6-di-(4-n-butylamino-1,2,2,6,6-pentamethylpiperidyl)-1,3,5-triazine and 1,2-bis(3-aminopropylamino)ethane, 8-acetyl-3-dodecyl-7,7,9,9-tetramethyl-1,3,8-triazaspiro[4.5]decane-2,4-dione, 3-dodecyl-1-(2,2,6,6-tetramethyl-4-piperidyl)pyrrolidine-2,5-dione, 3-dodecyl-1-(1,2,2,6,6-pentamethyl-4-piperidyl) pyrrolidine-2,5-dione, 5-(2-ethylhexanoyl)-oxymethyl-3,3,5-trimethyl-2-morpholinone, 1-(2-hydroxy-2-methylpropoxy)-4-octadecanoyloxy-2,2,6,6-tetramethylpiperidine, 1,3,5-tris(N-cyclohexyl-N-(2,2,6,6-tetramethylpiperazin-3-on-4-yl)amino)-s-triazine, 1,3,5-tris(N-cyclohexyl-N-(1,2,2,6,6-pentamethylpiperazin-3-on-4-yl)amino)-s-triazine, the reaction product of 2,4-bis[(1-cyclohexyloxy-2,2,6,6-piperidin-4-yl)butylamino]-6-chloro-s-triazine with N,N'-bis(3-aminopropyl)ethylenediamine), a mixture of 4-hexadecyloxy- and 4-stearyloxy-2,2,6,6-tetramethylpiperidine, a condensate of N,N'-bis(2,2,6,6-tetramethyl-4-piperidyl)hexamethylenediamine and 4-cyclohexylamino-2,6-dichloro-1,3,5-triazine, a condensate of 1,2-bis(3-aminopropylamino)ethane and 2,4,6-trichloro-1,3,5-triazine as well as 4-butylamino-2,2,6,6-tetramethylpiperidine (CAS Reg. No. [136504-96-6]); a condensate of 1,6-hexanediamine and 2,4,6-trichloro-1,3,5-triazine as well as N,N-dibutylamine and 4-butylamino-2,2,6,6-tetramethylpiperidine (CAS Reg. No. [192268-64-7]); N-(2,2,6,6-tetramethyl-4-piperidyl)-n-dodecylsuccinimide, N-(1,2,2,6,6-pentamethyl-4-piperidyl)-n-dodecylsuccinimide, 2-undecyl-7,7,9,9-tetramethyl-1-oxa-3,8-diaza-4-oxo-spiro[4,5]decane, a reaction product of 7,7,9,9-tetramethyl- 2-cycloundecyl-1-oxa-3,8-diaza-4-oxospiro-[4,5]decane and epichlorohydrin, 1,1-bis(1,2,2,6,6-pentamethyl-4-piperidyloxycarbonyl)-2-(4-methoxyphenyl)ethene, N,N'-bisformyl-N,N'-bis(2,2,6,6-tetramethyl-4-piperidyl)hexamethylenediamine, a diester of 4-methoxymethylenemalonic acid with 1,2,2,6,6-pentamethyl-4-hydroxypiperidine, poly[methylpropyl-3-oxy-4-(2,2,6,6-tetramethyl-4-piperidyl)]siloxane, a reaction product of maleic acid anhydride-a-olefin copolymer with 2,2,6,6-tetramethyl-4-aminopiperidine or 1,2,2,6,6-pentamethyl-4-aminopiperidine.

2.7. Oxamides, for example 4,4'-dioctyloxyoxanilide, 2,2'-diethoxyoxanilide, 2,2'-dioctyloxy-5,5'-di-tert-butoxanilide, 2,2'-didodecyloxy-5,5'-di-tert-butoxanilide, 2-ethoxy-2'-ethyloxanilide, N,N'-bis(3-dimethylaminopropyl)oxamide, 2-ethoxy-5-tert-butyl-2'-ethoxanilide and its mixture with 2-ethoxy-2'-ethyl-5,4'-di-tert-butoxanilide, mixtures of o- and p-methoxy-disubstituted oxanilides and mixtures of o- and p-ethoxy-disubstituted oxanilides.

2.8. 2-(2-Hydroxyphenyl)-1.3.5-triazines, for example 2,4,6-tris(2-hydroxy-4-octyloxyphenyl)-1,3,5-triazine, 2-(2-hydroxy-4-octyloxyphenyl)-4,6-bis(2,4-dimethylphenyl)-1,3,5-triazine, 2-(2,4-dihydroxyphenyl)-4,6-bis(2,4-dimethylphenyl)-1,3,5-triazine, 2,4-bis(2-hydroxy-4-propyloxyphenyl)-6-(2,4-dimethylphenyl)-1,3,5-triazine, 2-(2-hydroxy-4-octyloxyphenyl)-4,6-bis(4-methylphenyl)-1,3,5-triazine, 2-(2-hydroxy-4-dodecyloxyphenyl)-4,6-bis(2,4-dimethylphenyl)-1,3,5-triazine, 2-(2-hydroxy-4-tridecyloxyphenyl)-4,6-bis(2,4-dimethylphenyl)-1,3,5-triazine, 2-[2-hydroxy-4-(2-hydroxy-3-butyloxypropoxy)phenyl]-4,6-bis(2,4-dimethyl-1,3,5-triazine, 2-[2-hydroxy-4-(2-hydroxy-3-octyloxypropyloxy)phenyl]-4,6-bis(2,4-dimethyl)-1,3,5-triazine, 2-[4-(dodecyloxy/tridecyloxy-2-hydroxypropoxy)-2-hydroxyphenyl]-4,6-bis(2,4-dimethylphenyl) 1,3,5-triazine, 2-[2-hydroxy-4-(2-hydroxy-3-dodecyloxypropoxy)phenyl]-4,6-bis(2,4-dimethylphenyl)-1,3,5-triazine, 2-(2-hydroxy-4-hexyloxy)phenyl-4,6-diphenyl-1,3,5-triazine, 2-(2-hydroxy-4-methoxyphenyl)-4,6-diphenyl-1,3,5-triazine, 2,4,6-tris[2-hydroxy-4-(3-butoxy-2-hydroxypropoxy)phenyl]-1,3,5-triazine, 2-(2-hydroxyphenyl)-4-(4-methoxyphenyl)-6-phenyl-1,3,5-triazine, 2-{2-hydroxy-4-[3-(2-ethylhexyl-1-oxy)-2-hydroxypropyloxy]phenyl}-4,6-bis(2,4-dimethylphenyl)-1,3,5-triazine.

3. Metal deactivators, for example N,N'-diphenyloxamide, N-salicylal-N'-salicyloyl hydrazine, N,N'-bis(salicyloyl)hydrazine, N,N'-bis(3,5-di-tert-butyl-4-hydroxyphenylpropionyl)hydrazine, 3-salicyloylamino-1,2,4-triazole, bis(benzylidene)oxalyl dihydrazide, oxanilide, isophthaloyl dihydrazide, sebacoyl bisphenylhydrazide, N,N'-diacetyladipoyl dihydrazide, N,N'-bis(salicyloyl)oxalyl dihydrazide, N,N'-bis(salicyloyl)thiopropionyl dihydrazide.

4. Phosphites and phosphonites, for example triphenyl phosphite, diphenylalkyl phosphites, phenyldialkyl phosphites, tris(nonylphenyl) phosphite, trilauryl phosphite, trioctadecyl phosphite, distearylpentaerythritol diphosphite, tris(2,4-di-tert-butylphenyl) phosphite, diisodecyl pentaerythritol diphosphite, bis(2,4-di-tert-butylphenyl)pentaerythritol diphosphite, bis(2,4-dicumylphenyl)pentaerythritol diphosphite, bis(2,6-di-tert-butyl-4-methylphenyl)pentaerythritol diphosphite, diisodecyloxypentaerythritol diphosphite, bis(2,4-di-tert-butyl-6-methylphenyl)-pentaerythritol diphosphite, bis(2,4,6-tris(tert-butylphenyl)pentaerythritol diphosphite, tristearyl sorbitol triphosphite, tetrakis(2,4-di-tert-butylphenyl) 4,4'-biphenylene diphosphonite, 6-isooctyloxy-2,4,8,10-tetra-tert-butyl-12H-dibenz[d,g]-1,3,2-dioxaphosphocin, bis(2,4-di-tert-butyl-6-methylphenyl) methyl phosphite, bis(2,4-di-tert-butyl-6-methylphenyl) ethyl phosphite, 6-fluoro-2,4,8,10-tetra-tert-butyl-12-methyl-dibenz[d,g]-1,3,2-dioxaphosphocin, 2,2',2''-nitrilo-[triethyltris(3,3',5,5'-tetra-tert-butyl-1,1'-biphenyl-2,2'-diyl) phosphite], 2-ethylhexyl (3,3',5,5'-tetra-tert-butyl-1,1'-biphenyl-2,2'-diyl)phosphite, 5-butyl-5-ethyl-2-(2,4,6-tri-tert-butylphenoxy)-1,3,2-dioxaphosphirane.

The following phosphites are especially preferred:

Tris(2,4-di-tert-butylphenyl) phosphite (Irgafos®168, Ciba-Geigy), tris(nonylphenyl)phosphite,

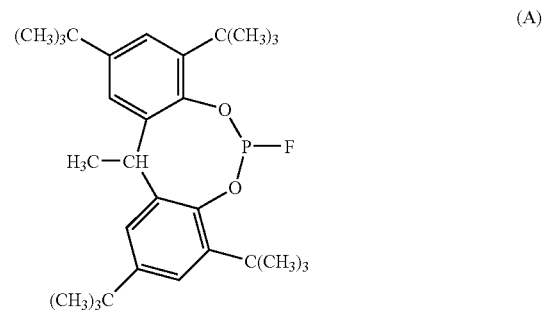

(A)

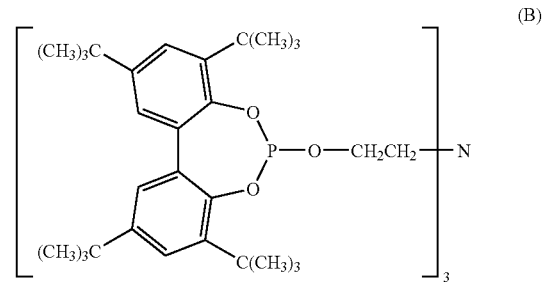

(B)

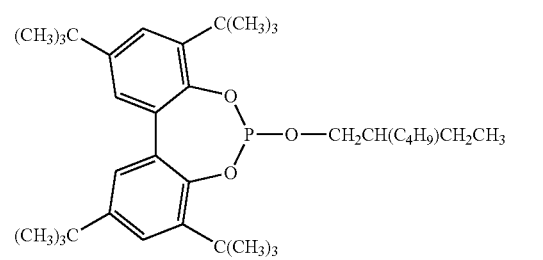

(C)

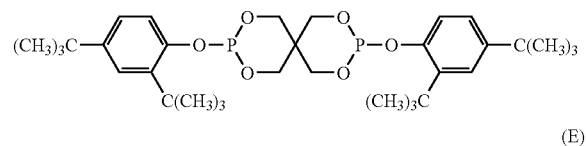

(D)

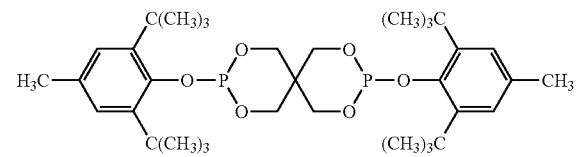

(E)

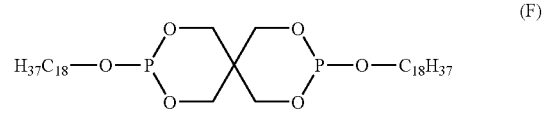

(F)

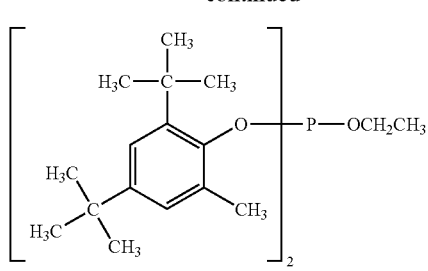

(G)

5. Hydroxylamines, for example N,N-dibenzylhydroxylamine, N,N-diethylhydroxylamine, N,N-dioctylhydroxylamine, N,N-dilaurylhydroxylamine, N,N-ditetradecylhydroxylamine, N,N-dihexadecylhydroxylamine, N,N-dioctadecylhydroxylamine, N-hexadecyl-N-octadecylhydroxylamine, N-heptadecyl-N-octadecylhydroxylamine, N,N-dialkylhydroxylamine derived from hydrogenated tallow amine.

6. Nitrones, for example N-benzyl-alpha-phenylnitrone, N-ethyl-alpha-methyinitrone, N-octylalpha-heptylnitrone, N-lauryl-alpha-undecyinitrone, N-tetradecyl-alpha-tridecylnitrone, N-hexadecyl-alpha-pentadecylnitrone, N-octadecyl-alpha-heptadecylnitrone, N-hexadecyl-alpha-heptadecylnitrone, N-ocatadecyl-alpha-pentadecylnitrone, N-heptadecyl-alpha-heptadecylnitrone, N-octadecyl-alpha-hexadecylnitrone, nitrone derived from N,N-dialkylhydroxylamine derived from hydrogenated tallow amine.

7. Thiosyneraists, for example dilauryl thiodipropionate or distearyl thiodipropionate.

8. Peroxide scavengers, for example esters of β-thiodipropionic acid, for example the lauryl, stearyl, myristyl or tridecyl esters, mercaptobenzimidazole or the zinc salt of 2-mercaptobenzimidazole, zinc dibutyidithiocarbamate, dioctadecyl disulfide, pentaerythritol tetrakis(β-dodecylmercapto)propionate.

9. Polvamide stabilisers, for example copper salts in combination with iodides and/or phosphorus compounds and salts of divalent manganese.

10. Basic co-stabilisers, for example melamine, polyvinylpyrrolidone, dicyandiamide, triallyl cyanurate, urea derivatives, hydrazine derivatives, amines, polyamides, polyurethanes, alkali metal salts and alkaline earth metal salts of higher fatty acids, for example calcium stearate, zinc stearate, magnesium behenate, magnesium stearate, sodium ricinoleate and potassium palmitate, antimony pyrocatecholate or zinc pyrocatecholate.

11. Nucleatina agents, for example inorganic substances, such as talcum, metal oxides, such as titanium dioxide or magnesium oxide, phosphates, carbonates or sulfates of, preferably, alkaline earth metals; organic compounds, such as mono- or polycarboxylic acids and the salts thereof, e.g. 4-tert-butylbenzoic acid, adipic acid, diphenylacetic acid, sodium succinate or sodium benzoate; polymeric compounds, such as ionic copolymers (ionomers). Especially preferred are 1,3:2,4-bis(3',4'-dimethylbenzylidene)sorbitol, 1,3:2,4-di(paramethyldibenzylidene)sorbitol, and 1,3:2,4-di(benzylidene)sorbitol.

12. Fillers and reinforcing agents, for example calcium carbonate, silicates, glass fibres, glass beads, asbestos, talc, kaolin, mica, barium sulfate, metal oxides and hydroxides, carbon black, graphite, wood flour and flours or fibers of other natural products, synthetic fibers.

13. Other additives, for example plasticisers, lubricants, emulsifiers, pigments, rheology additives, catalysts, flow-control agents, optical brighteners, flameproofing agents, antistatic agents and blowing agents.

14. Benzofuranones and indolinones, for example those disclosed in U.S. Pat. No. 4,325,863; U.S. Pat. No. 4,338,244; U.S. Pat. No. 5,175,312; U.S. Pat. No. 5,216,052; U.S. Pat. No. 5,252,643; DE-A-4316611; DE-A-4316622; DE-A-4316876; EP-A-0589839 or EP-A-0591102 or 3-[4-(2-acetoxyethoxy)-phenyl]-5,7-di-tert-butyl-benzofuran-2-one, 5,7-di-tert-butyl-3-[4-(2-stearoyloxyethoxy)phenyl]benzofuran-2-one, 3,3'-bis[5,7-di-tert-butyl-3-(4-[2-hydroxyethoxy]phenyl)benzofuran-2-one], 5,7-di-tert-butyl-3-(4-ethoxyphenyl)benzofuran-2-one, 3-(4-acetoxy-3,5-dimethylphenyl)-5,7-di-tert-butyl-benzofuran-2-one, 3-(3,5-dimethyl-4-pivaloyloxyphenyl)-5,7-di-tert-butylbenzofuran-2-one, 3-(3,4-dimethylphenyl)-5,7-di-tert-butyl-benzofuran-2-one, 3-(2,3-dimethylphenyl)-5,7-di-tert-butyl-benzofuran-2-one.

The nature and amount of the further stabilisers added is determined by the nature of the substrate to be stabilised and its intended use; from 0.1 to 10% by weight, for example from 0.2 to 5% by weight, based on the material to be stabilised, are often used.

Especially advantageous is the use of the compounds according to the invention in combination with sterically hindered amines, for example 2,2,6,6-tetralkylpiperidine derivatives. The invention therefore includes a synergistic stabiliser mixture comprising (a) a compound of formula I and (b) at least one sterically hindered amine, the salt thereof with any desired acid or the complex thereof with a metal, and a composition comprising A) an organic material that is sensitive to oxidative, thermal or/and actinic degradation/formation,
B) at least one compound of formula 1, and
C) a conventional additive of the sterically hindered amine type.

Preferred sterically hindered amines are, for example, those mentioned in the above list in 2.6 or hereinafter as additives to the coating compositions according to the invention.

Of particular interest is the use of compounds of formula I as stabilisers in synthetic organic polymers, and also corresponding compositions.

The organic materials to be protected are preferably natural, semi-synthetic-or synthetic organic materials. In cosmetic preparations, the compounds according to the invention can also be used as sun protection agents for human or animal skin or hair. The invention therefore relates also to a cosmetic preparation comprising a UV absorber of formula I, preferably in an amount of from 0.25 to 5% by weight, based on the total weight of the preparation, and a skin- and hair-tolerable carrier or excipient.

The stabiliser mixtures according to the invention can be used especially advantageously in compositions comprising as component A a synthetic organic polymer, especially a thermoplastic polymer, a binder for coatings, such as, for example, surface-coatings, or a photographic material. Suitable thermoplastic polymers are, for example, polyolefins, especially polyethylene (PE) and polypropylene (PP) and copolymers thereof, and polymers comprising hetero atoms in the main chain (see e.g. U.S. Pat. No. 5,288,778, columns 2 and 3).

The additives according to the invention, where applicable together with further components, can be added to the material individually or as a mixture. If desired, the individual components can be mixed with one another before being incorporated into the polymer, for example in a dry state, by compacting or as a melt.

Incorporation of the additives according to the invention and optionally further components into the polymer is carried out according to customary methods, such as, for example, dry mixing in powder form or wet mixing in the form of solutions, dispersions or suspensions, for example in inert solvents, water or oil. Incorporation of the additives according to the invention and optionally further components can be carried out, for example, before or after shaping, or by applying or adding the dissolved or dispersed additive or additive mixture to the polymer material, with or without subsequent removal of the solvent or suspension agent/dispersant. Addition directly into the processing apparatus (e.g. extruder, mixer etc.), for example from a dry mixture or powder or as a solution or dispersion, suspension or melt, is possible.

The incorporation can be carried out in principle in any heatable vessel equipped with stirring apparatus, for example in closed apparatuses, such as kneaders, mixers or stirred vessels. Incorporation is preferably carried out in an extruder or kneader. The incorporation can be carried out under an inert atmosphere or equally in the presence of oxygen.

Any conventional apparatus for melting and mixing the polymer can be used for the addition of the additive or additive mixture. Suitable apparatuses, such as, for example, those mentioned above, are known in the art.

Preferably, the additives are added during the processing step in the extruders Especially preferred processing apparatuses are single-screw extruders, twin-screw extruders running in opposite directions or in the same direction, planetary gear extruders or kneaders. Processing machines can be equipped with one or more degassing vessels to which a negative pressure can be applied.

Suitable extruders and kneaders are described, for example, in Handbuch der Kunststoffextrusion, Vol. 1 Grundlagen, editors F. Hensen, W. Knappe, H. Potente, 1989, pp. 3–7, *ISBN:* 3-446-14339-4 (Vol. 2 *Extrusionsanlagen* 1986, *ISBN* 3-446-14329-7).

The screw length may, for example, be 1–60, preferably 35–48, screw diameters. The rotation speed of the screw is preferably 10–600 revolutions per minute (rpm), especially 25–300 rpm.

The maximum throughput depends upon the screw diameter, the rotation speed and the driving force. The process according to the invention can also be operated at less than the maximum throughput by altering the mentioned parameters or by the use of metering machines.

When several components are added, these may be premixed or metered in individually.

The additives according to the invention and optionally further components can be added to the polymer material also by spraying. They are suitable for diluting other additives (for example the above-mentioned conventional additives) or melts thereof, making it possible to spray them on together with the latter. Especially advantageous is addition of the additives according to the invention by spraying during the deactivation of the polymerisation catalyst; in that case, the evolution of vapour can be utilised for deactivation. For example, addition by spraying, optionally together with other additives, can be advantageous in the case of spherically polymerised polyolefins.

The additives according to the invention and optionally further additives can be added to the polymer also in the form of concentrates (master batches) that comprise those components, for example, in a concentration of from 1 to 40%, preferably from 2 to 20%, relative to the weight of the polymer. That polymer does not necessarily have to have the same structure as the polymer to which the additives are finally added. The polymer may be used in the form of a powder, granules, solutions, suspensions or in the form of latices.

Incorporation can be carried out before or during shaping, or by applying the dissolved or dispersed compound to the polymer, where applicable with subsequent evaporation of the solvent. In the case of elastomers, these may also be stabilised in the form of latices. A further possibility of incorporating the compounds of formula I into polymers comprises adding them before, during or immediately after polymerisation of the corresponding monomers or before crosslinking. The compounds of formula I can be added as such or alternatively in encapsulated form (e.g. in waxes, oils or polymers).

The stabilised polymer compositions obtained in that manner can be converted into shaped articles, such as e.g. into fibres, films, monofilaments, tapes, non-woven fabrics, surface-coatings, panels, web panels, vessels, tubes and other profiles, by the usual methods, such as e.g. hot-pressing, spinning, extrusion, blow-moulding, rotomoulding, spraying or injection-moulding.

Use in multilayer systems is also of interest. In this case, a polymer composition according to the invention having a relatively high content of stabiliser according to the invention, for example 5–15% by weight, is applied in a thin layer (10–100 μm) to a shaped article made from a polymer containing little or no stabiliser of formula I. Application can be carried out simultaneously with the shaping of the basic body, e.g. by so-called coextrusion. Application can also be carried, out, however, to the ready-shaped basic body, e.g. by lamination with a film or by coating with a solution. The outer layer or layers of the finished article have the function of a UV filter which protects the interior of the article from UV light. The outer layer contains preferably 5–15% by weight, especially 5–10% by weight, of at least one compound of formula I. In the case of transparent filter layers, the UV absorber can also be present in a different layer or in the single polymer layer.

The materials stabilised in that manner are distinguished by high resistance-to weathering, especially by high resistance to UV light. As a result, the polymers retain their mechanical properties and also their colour and gloss for a long time even when used outside.

By using the compounds according to the invention in UV filter layers the passage of UV radiation and its associated damaging effects can be effectively prevented. It is therefore possible to produce inter alia protective containers or packaging films, for example for foodstuffs, medicaments or cosmetics.

Compounds of the present formula I can be used advantageously in plastics films, for example polyethylene films, of the kind used in agriculture especially as a covering for hothouses. A particular advantage of hothouse films or agrofilms stabilised according to the invention is that it is possible to filter out the portion of UV radiation that directly damages the crops and/or that favours the spread of a number of pathogenic microorganisms, such as fungi and viruses, and pathogenic insects, such as e.g. whitefly, aphids, thrips etc. Those pests can be significantly reduced if the admission of UV radiation to the plants is prevented or reduced. [R. Reuveni et al., Plasticulture No. 102, p. 7 (1994); Y. Antignus etal., CIPA Congress March 1997, pp.23–33]. Surprisingly, despite that UV filter action, the activity of useful insects in the hothouses (usually bumblebees or bees), which require UV radiation in a specific bandwidth, is not disturbed. At the same time, the hydroxyphenyl UV absorbers of the present invention exhibit good compatibility and persistence in the polyolefin. The present invention accordingly also contributes to the improvement of agrofilms and describes a method for suppressing microbial infestation of cultivated plants, such as, for example, tomatoes, cucumbers, gourds, melons, citrus fruit, roses, strawberries, grapes, paprika etc.

Of particular interest is the use of the stabilisers according to the invention for coatings, for example for surface-coatings.

The coating composition preferably contains 0.01–10 parts by weight, especially 0.05–10 parts by weight, more especially 0.1–5 parts by weight, of the stabiliser according to the invention (component B) per 100 parts by weight of solid binder (component A).

Multilayer systems are possible here as well, it being possible for the concentration of the stabilisers in the top layer to be higher, for example from 1 to 15 parts by weight, especially from 3 to 10 parts by weight, based on 100 parts by weight of solid binder.

The use of the compounds as stabiliser in coatings is accompanied by the additional advantage that delamination, i.e. flaking-off of the coating from the substrate, is prevented. Substrates may in this case be, for example, wood, ceramic materials, metals, plastics materials, surface-coated articles and articles primer-coated with organic materials.

The binders may in principle be any binders that are customary in the art, for example those described in Ullmann's Encyclopedia of Industrial Chemistry, 5th ed., Vol. A18, pp. 368–426, VCH, Weinheim 1991. The binder will generally be a film-forming binder, based on a thermoplastic or thermosetting resin, predominantly on a thermosetting resin. Examples thereof are alkyd, acrylic, polyester, phenolic, melamine, epoxy and polyurethane resins and mixtures thereof.

It may be a cold-curable or a hot-curable binder, and the addition of a curing catalyst may be advantageous. Suitable catalysts, which accelerate full curing of the binder, are described, for example, in Ullmann's Encyclopedia of Industrial Chemistry, Vol. A18, p. 469, VCH Verlagsgesellschaft, Weinheim 1991.

Preference is given to coating compositions in which component A is a binder consisting of a functional acrylate resin and a crosslinking agent.

Examples of coating compositions with specific binders are:

1. surface-coatings based on cold- or hot-crosslinkable alkyd, acrylate, polyester, epoxy or melamine resins or mixtures of such resins, optionally with the addition of a curing catalyst;

2. two-component polyurethane surface-coatings based on hydroxyl-group-containing acrylate, polyester or polyether resins and aliphatic or aromatic isocyanates, isocyanurates or polyisocyanates;

3. two-component polyurethane surface-coatings based on thiol-group-containing acrylate, polyester or polyether resins and aliphatic or aromatic isocyanates, isocyanurates or polyisocyanates;

4. one-component polyurethane surface-coatings based on blocked isocyanates, isocyanurates or polyisocyanates, which are de-blocked during stoving; it is also possible to add melamine resins as appropriate;

5. one-component polyurethane surface-coatings based on aliphatic or aromatic urethanes or polyurethanes and hydroxyl-group-containing acrylate, polyester or polyether resins;

6. one-component polyurethane surface-coatings based on aliphatic or aromatic urethane acrylates or polyurethane acrylates having free amine groups in the urethane structure and melamine resins or polyether resins, optionally with the addition of a curing catalyst;

7. two-component surface-coatings based on (poly)ketimines and aliphatic or aromatic isocyanates, isocyanurates or polyisocyanates;

8. two-component surface-coatings based on (poly)ketimines and an unsaturated acrylate resin or a polyacetoacetate resin or a methacrylamidoglycolate methyl ester;

9. two-component surface-coatings based on carboxy- or amino-group-containing polyacrylates and polyepoxides;

10. two-component surface-coatings based on anhydride-group-containing acrylate resins and a polyhydroxy or polyamino component;

11. two-component surface-coatings based on acrylate-containing anhydrides and polyepoxides;

12. two-component surface-coatings based on (poly)oxazolines and anhydride-group-containing acrylate resins or unsaturated acrylate resins or aliphatic or aromatic isocyanates, isocyanurates or polyisocyanates;

13. two-component surface-coatings based on unsaturated (poly)acrylates and (poly)malonates;

14. thermoplastic polyacrylate surface-coatings based on thermoplastic acrylate resins or extrinsically crosslinking acrylate resins in combination with etherified melamine resins;

15. surface-coating systems based on siloxane-modified or fluoro-modified acrylate resins;

16. surface-coating systems, especially clear surface-coatings, based on malonate-blocked isocyanates with melamine resins (e.g. hexamethoxymethylmelamine) as crosslinker (acid-catalysed);

17. UV-curable systems based on oligomeric urethane acrylates and/or acylate acrylates optionally with the addition of other oligomers or monomers;

18. dual-cure systems which are cured first thermally and then by UV or vice versa, wherein components of the surface-coating composition contain double bonds that can be caused to react by UV light and photoinitiators and/or by electron-beam curing.

They may also be coating systems based on siloxanes. Such coating systems are described, for example, in WO 98/56852, WO 98/56853, DE-A-2 914 427 and DE-A-4 338 361.

In addition to the binders and the stabiliser, the coating composition preferably comprises as further component (C) a light stabiliser of the sterically hindered amine type, the 2-(2-hydroxyphenyl)-1,3,5-triazine type and/or of the 2-hydroxyphenyl-2H-benzotriazole type, for example those mentioned in the above list in Sections 2.1, 2.6 and 2.8. Further examples of light stabilisers of the 2-(2-hydroxyphenyl)-1,3,5-triazine type which can be used advantageously are listed inter alia in the publications U.S. Pat. No. 4,619,956, EP-A-434 608, U.S. Pat. No. 5,198,498, U.S. Pat. No. 5,322,868, U.S. Pat. No. 5,369,140, U.S. Pat. No. 5,298,067, WO-94/18278, EP-A-704 437, GB-A-2 297 091, and especially WO-96/28431. Of particular interest industrially in this context is the addition of compounds of the 2-resorcinyl-4,6-diaryl-1,3,5-triazine class wherein aryl is phenyl or biphenylyl, and/or of the 2-hydroxyphenyl-2H-benzotriazole class.

For obtaining maximum light stability, the addition of sterically hindered amines, such as those mentioned in the above list in 2.6, is especially of interest. The invention therefore relates also to a coating composition that comprises, in addition to the binder A and the stabiliser B, as further component C a light stabiliser of the sterically hindered amine type.

The latter is preferably a 2,2,6,6-tetraalkylpiperidine derivative or a derivative of 3,3,5,5-tetraalkyl-morpholin-2-one that contains at least one group of the formula

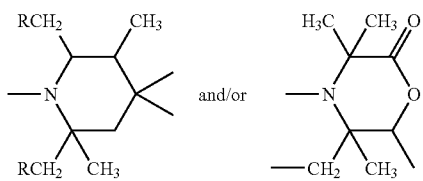

wherein R is hydrogen or methyl, especially hydrogen.

Component C is preferably used in an amount of 0.05–5 parts by weight per 100 parts by weight of the solid binder.

Examples of tetraalkylpiperidine derivatives that can be used as component C are to be found in EP-A-356 677, pp. 3–17, sections a) to f). The said sections of that EP-A are regarded as forming part of the present description. It is especially advantageous to use the following tetraalkylpiperidine derivatives:

bis(2,2,6,6-tetramethylpiperidin-4-yl)succinate,
bis(2,2,6,6-tetramethylpiperidin-4-yl)sebacate,
bis(1,2,2,6,6-pentamethylpiperidin-4-yl)sebacate,
butyl-(3,5-di-tert-butyl-4-hydroxybenzyl)-malonic acid di-(1,2,2,6,6-penta-methylpiperidin-4-yl) ester,
bis(1-octyloxy-2,2,6,6-tetramethylpiperidin-4-yl)sebacate,
tetra(2,2,6,6-tetramethylpiperidin-4-yl)-butane-1,2,3,4-tetracarboxylate,
tetra(1,2,2,6,6-pentamethylpiperidin-4-yl)-butane-1,2,3,4-tetracarboxylate,
2,2,4,4-tetramethyl-7-oxa-3,20-diaza-21-oxo-dispiro[5.1.11.2]-heneicosane,
8-acetyl-3-dodecyl-1,3,8-triaza-7,7,9,9-tetramethylspiro[4,5]-decane-2,4-dione,
1,1-bis(1,2,2,6,6-pentamethylpiperidin-4-yl-oxycarbonyl)-2-(4-methoxyphenyl)-ethene, or a compound of the formula

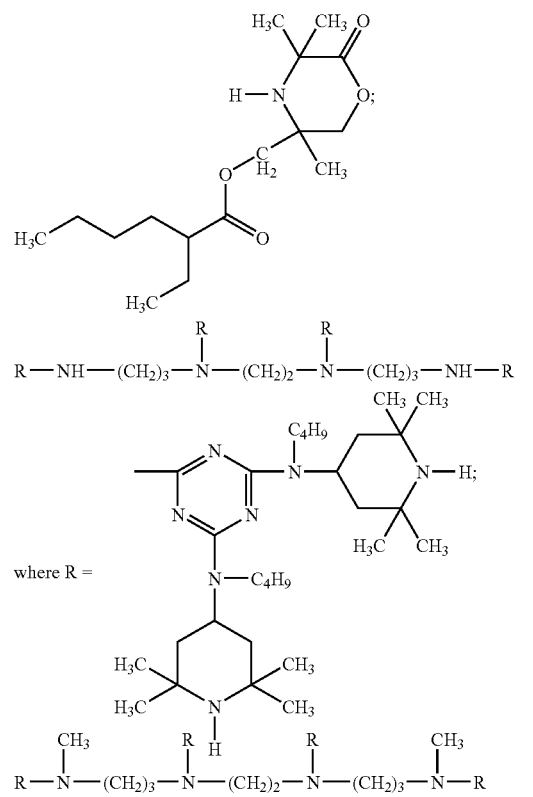

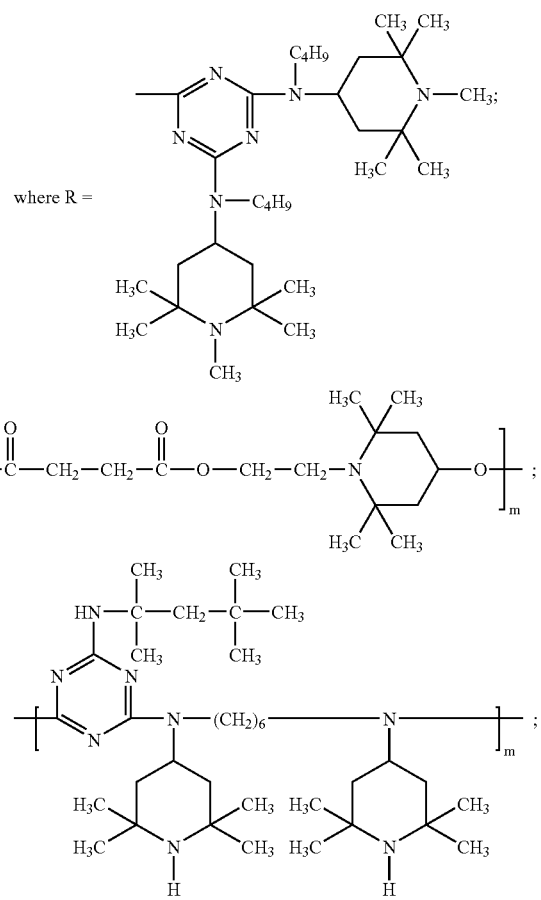

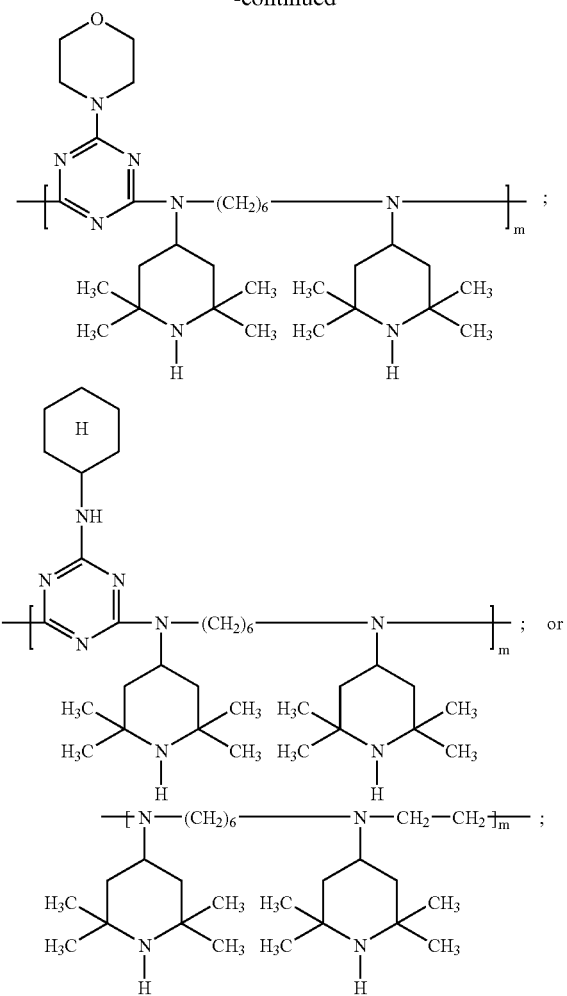

wherein m has a value of 5–50.

In addition to components A, B and optionally C, the coating composition may comprise further components, e.g. solvents, pigments, dyes, plasticisers, stabilisers, rheology additives, such as, for example, thixotropic agents, drying catalysts or/and flow improvers.

Possible components are, for example, those described in Ullmann's Encyclopedia of Industrial Chemistry, 5th ed., Vol. A18, pp. 429–471, VCH, Weinheim 1991.

Possible drying catalysts and curing catalysts are, for example, free (organic) acids or bases or also (organic) blocked acids or bases that can be activated by thermal energy or light energy, organic metal compounds, amines, amino-group-containing resins or/and phosphines. Organic metal compounds are e.g. metal carboxylates, especially those of the metals Pb, Mn, Co, Zn, Zr or Cu, or metal chelates, especially those of the metals Al, Ti, Zr or Hf, or organometal compounds, such as e.g. organotin compounds.

Examples of metal carboxylates are the stearates of Pb, Mn or Zn, the octoates of Co, Zn or Cu, the naphthenates of Mn and Co or the corresponding linoleates, resinates or tallates.

Examples of metal chelates are the aluminium, titanium, zirconium or hafnium chelates of acetyl acetone, ethylacetyl acetate, salicylaldehyde, salicylaldoxime, o-hydroxyacetophenone or ethyl-trifluoroacetyl acetate and the alkoxides of those metals.

Examples of organotin compounds are dibutyltin oxide, dibutyltin dilaurate and dibutyltin dioctoacte.

Examples of amines are especially tertiary amines, such as e.g. tributylamine, triethanolamine, N-methyidiethanolamine, N-dimethylethanolamine, N-ethylmorpholine, N-methylmorpholine and diazabicyclooctane (triethylenediamine), diazabicycloundecene, DBN (=1,5-diazabicyclo[4.3.0]non-5-ene) and the salts thereof. Further examples are quaternary ammonium salts, such as e.g. trimethylbenzylammonium chloride.

Amino-group-containing resins are simultaneously binders and curing catalysts. Examples thereof are amino-group-containing acrylate copolymers.

It is also possible to use phosphines, such as e.g. triphenylphosphine, as curing catalysts.

The coating compositions may also be radiation-curable coating compositions. In that case the binder consists substantially of monomeric or oligomeric compounds having ethylenically unsaturated bonds (prepolymers) which after application are cured by actinic radiation, i.e. converted into a crosslinked, high-molecular-weight form. If a system is UV-curing, it generally comprises a photoinitiator in addition. Corresponding systems are described in the above-mentioned publication Ullmann's Encyclopedia of Industrial Chemistry, 5th ed., Vol. A18, pages 451–453. In radiation-curable coating compositions, the stabilisers can be employed also without the addition of sterically hindered amines.

The coating compositions can be applied to any desired substrates, for example to metal, wood, plastics material or ceramic materials. They are preferably used as topcoat in the finishing of automobiles. If the topcoat consists of two layers of which the bottom layer is pigmented and the top layer is not pigmented, the coating composition can be used for the top layer or the bottom layer or for both layers, but preferably for the top layer.

The coating compositions can be applied to the substrates by the usual methods, for example by coating, spraying, pouring, dipping or electrophoresis; see also Ullmann's Encyclopedia of Industrial Chemistry, 5th ed., Vol. A18, pp. 491–500.

Depending upon the binder system, curing of the coatings can be carried out at room temperature or by heating. The coatings are preferably cured at 50–150° C., and in the case of powder coating compositions or coil-coating compositions also at higher temperatures.

The resulting coatings exhibit excellent resistance to the damaging effects of light, oxygen and heat; special mention is to be made of the good light stability and weathering resistance of the resulting coatings, for example surface-coatings.

The coating compositions may comprise an organic solvent or solvent mixture in which the binder is soluble. The coating composition may also, however, be an aqueous solution or dispersion. It may also be a mixture of an organic solvent and water. The coating composition may also be a high solids surface coating or may be solvent-free (e.g. a powder coating composition). Powder coating compositions are, for example, those described in Ullmann's Encyclopedia of Industrial Chemistry, 5th ed., A1 8, pages 438–444. The powder coating composition may also be in the form of a powder slurry, i.e. a dispersion of the powder preferably in water.

The pigments may be inorganic, organic or metallic pigments. Preferably, the coating compositions contain no pigments and are used as clear surface-coatings.

Preference is given to use of the coating composition as topcoat for applications in the automobile industry, especially as the pigmented or unpigmented top layer of the finish. Its use for underlying layers is, however, also possible.

If extremely thin UV-absorbing layers are to be produced, the compounds of formula I can also be applied to a substrate by plasma-enhanced deposition. Numerous possible methods of obtaining plasmas under vacuum conditions are described in the literature. The electrical energy can be coupled in inductively or capacitatively. Direct current or alternating current may be used, it being possible for the frequency of the alternating current to vary from a few kHz to the megahertz range. Feeding-in in the microwave range (gigahertz) is also possible.

Preferred substrates are metals, semi-conductors, glass, quartz or thermoplastic, crosslinked or structurally crosslinked plastics materials.

As a semi-conductor substrate, silicon especially is to be mentioned, which may, for example, be in the form of wafers.

As metals, especially aluminium, chromium, steel and vanadium are to be mentioned, which are used for the manufacture of high-quality mirrors, such as, for example, telescope mirrors or automobile headlamp mirrors. Aluminium is especially preferred.

As primary plasma gases it is possible to use, for example, He, argon, xenon, $N_2$, $O_2$ or air, non-reactive gases such as He, argon and xenon being preferred. When the stabilisers are vaporised, they mix with the plasma gas and are likewise ionised.

The deposition process with the stabilisers is not per se sensitive to the gas supplied and the coupling-in of the electrical energy. The crucial factor is that it is carried out at a relatively low pressure.

The pressure is preferably from $10^{-6}$ mbar to $10^{-2}$ mbar, especially from $10^{-3}$ to $10^{-4}$ mbar.

The material may, for example, be applied to a plasma electrode and vaporised directly from there. Preferably, however, the material to be vaporised will be on a separately heatable plate or in a crucible located outside the plasma discharge. The crucible or the plate may be at a positive or negative electrical potential with respect to the plasma.

Practical arrangements for producing the plasma and for the deposition are described, for example, by A. T. Bell, "Fundamentals of Plasma Chemistry" in "Technology and Application of Plasma Chemistry", published by J. R. Holahan and A. T. Bell, Wiley, New York (1974) or by H. Suhr, Plasma Chem. Plasma Process 3(1),1, (1983).

The temperature at which the stabilisers are vaporised is preferably from 20° C. to 350° C., especially from 100° C. to 250° C.

The process is especially suitable for depositing thin layers. The deposited layer preferably has a thickness of from 10 nm to 1000 nm, especially from 50 nm to 500 nm and more especially from 100 nm to 300 nm.

Also preferred is the use of the compounds according to the invention in recording materials. The latter are to be understood as being, for example, those described in Research Disclosure 1990, 31429 (pages 474–480) for photographic reproduction and other reproduction techniques. Recording materials, such as e.g. photographic material and components present therein, are described, for example, in U.S. Pat. No. 6,184,375 from column 34, line 9, to column 63, line 52, or in GB-A-2 343 007 from page 22, last paragraph, to page 106, line 35. The compounds according to the invention of formula I can be used therein analogously to the UV absorbers described in GB-A-2 343 007 from page 97, 3rd paragraph, to page 110, in place of those UV absorbers or in combination therewith, or analogously to the compounds of formula I described in U.S. Pat. No. 6,184, 375.

The compounds according to the invention can also be used advantageously as UV absorbers in protective coatings, films and foils in liquid crystal displays for protection against UV radiation and to protect polymer material and other components in the liquid crystal displays against damage by UV light. Examples of such fields of application and materials are to be found inter alia in:

JP-A-10-152568 (Jun. 9, 1998); JP-A-2000-227509 (Feb. 8, 1999); JP-A-2000-227508 (Aug. 2, 1999); JP-A-11-258425 (Nov. 30, 1998); JP-A-11-258421 (Mar. 13, 1998); JP-A-11-242119 (Nov. 30, 1998); JP-A-11-119003 (Oct. 13, 1997); JP-A-09-288213 (Apr. 19, 1996); JP-A-09-288212 (Apr. 19, 1996); JP-A-08-216316 (Feb. 14, 1995); JP-A-08-216324 (Feb. 14, 1995); and Chem. Abstr. 131:45869.

The compounds according to the invention can also be used advantageously in optical recording layers and recording media in which laser radiation, e.g. by short-wave irradiation by means of blue laser diodes (wavelength for example 405 nm), causes a change in the optical characteristics, by means of which digital information can be stored and subsequently retrieved from the storage layer or the storage medium. Examples of such fields of application and materials are to be found inter alia in JP-A-2001-277720; JP-A-2002-160452.

The following Examples illustrate the invention further. Unless specified otherwise, all data in parts or percent in the Examples, just as in the remainder of the description and in the patent claims, are by weight. In the Examples and the Table, the following abbreviations inter alia may be used:

| | |
|---|---|
| diglyme: | diethylene glycol dimethyl ether |
| DMSO | dimethyl sulfoxide |
| DMF | dimethylformamide |
| AcOEt: | ethyl acetate |
| $CHCl_3$: | chloroform |
| $CDCl_3$: | deuterochloroform |
| DSC: | Differential Scanning Calorimetry = differential thermoanalysis |
| ε: | molar extinction coefficient |
| $^1$H-NMR: | nuclear magnetic resonance of the $^1$H nuclide |
| TLC: | thin-layer chromatography (eluant usually hexane/ethyl acetate) |
| in. vac. | under reduced pressure |
| mm Hg | torr (1 torr = 133.322 Pa) |
| m.p. | melting point |
| THF | tetrahydrofuran |
| $T_g$: | glass transition temperature |
| UVA | UV-light-absorbing compound (UV absorber) |
| $\lambda_{max}$ | long-wave absorption maximum (nm) |
| ™, ® | registered trade mark. |

A: PREPARATION EXAMPLES

Example A1

Preparation of bis-α-naphthyl-(2,4-dihydroxyphenyl)-triazine

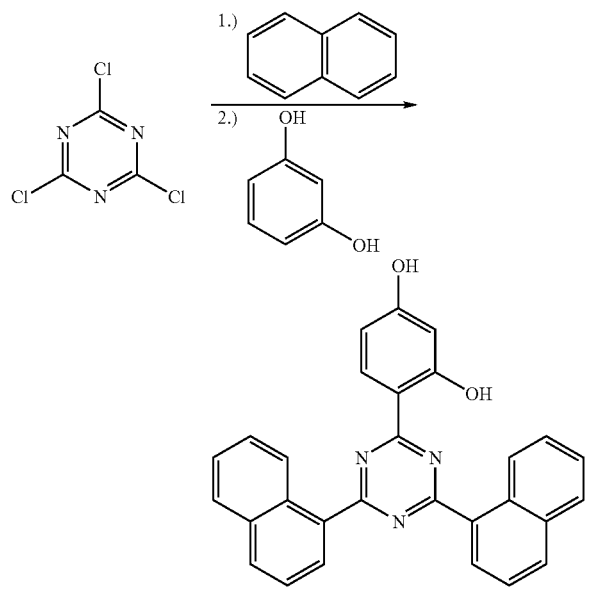

6.5 g of 36% hydrochloric acid are added dropwise at 0° C. under nitrogen to a suspension of 111 g of aluminium chloride and 50.0 g of cyanuric chloride in 100 ml of 1,2-dichlorobenzene. The reaction mixture is stirred for a further 1 h at 25° C. To that mixture there is added within 1.5 h a warmed solution of 66.0 g of naphthalene in 100 ml of 1,2-dichlorobenzene. When the addition is complete, the reaction mixture is stirred for 2 h at 25° C. 32.8 g of resorcinol are added in portions to that reaction mixture at 60° C. After 2 h, the reaction mixture is hydrolysed with ice-water and the product is filtered off. The product is purified by treatment with ethyl methyl ketone and isopropanol.

$^1$H-NMR (300 MHz, DMSO-$d_6$) δ: 13.08 (s, 1H); 10.5 (s, 1H); 9.02 (d, J=7.5 Hz, 2H); 8.57 (d, J=8.07 Hz, 1H); 8.46 (d, J=7.2 Hz, 2H); 8.34 (d, J=8.1 Hz, 2H); 8.22–8.19 (m, 2H); 7.70–7.86 (m, 6 H); 6.71 (dd, J=2.1 Hz, J=8.7 Hz, 1H); 6.53 (d, J=2.1 Hz, 1H).

Example A2

Preparation of bis-α-naphthyl-(2-hydroxy-4-n-hexyloxy-phenyl)-triazine

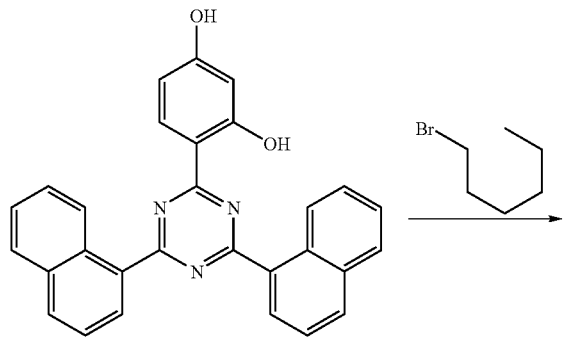

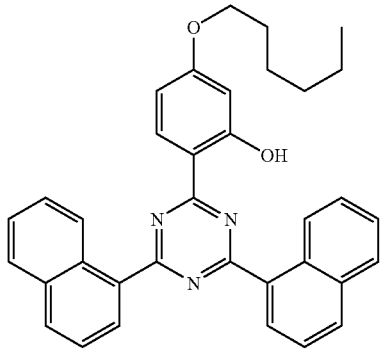

20.7 g of potassium carbonate and 18.2 g of hexyl bromide are added to a solution of 44.1 g of the product from Example 1 in 50 ml of DMF. That reaction mixture is heated at 100° C. for 2 h, then poured onto ice-water and acidified with dilute hydrochloric acid. The aqueous phase is extracted with dichloromethane. The organic phase is washed repeatedly with water and then dried with magnesium sulfate. Chromatography on silica gel yields the product.

$^1$H-NMR (300 MHz, CDCl$_3$) δ: 13.2 (s, 1H); 9.02 (s broad, 2H); 8.61 (d, J=9 Hz, 1H); 8.42 (s broad, 2H); 8.08 (d, J=9 Hz, 2H); 7.98 (d, J=9 Hz, 2H); 7.55–7.67 (m, 4H); 6.60 (dd, J=3 Hz, J=9 Hz, 1H); 6.53 (d, J=3 Hz, 1H); 4.03 (t, J=6 Hz, 2H); 1.5-1.86 (m, 2H); 1.32–1.54 (m, 6H); 0.92 (m, 3H).

Example A3

Preparation of bis-α-naphthyl-(2-hydroxy-4-(2-ethyl)hexyloxy-phenyl)-triazine

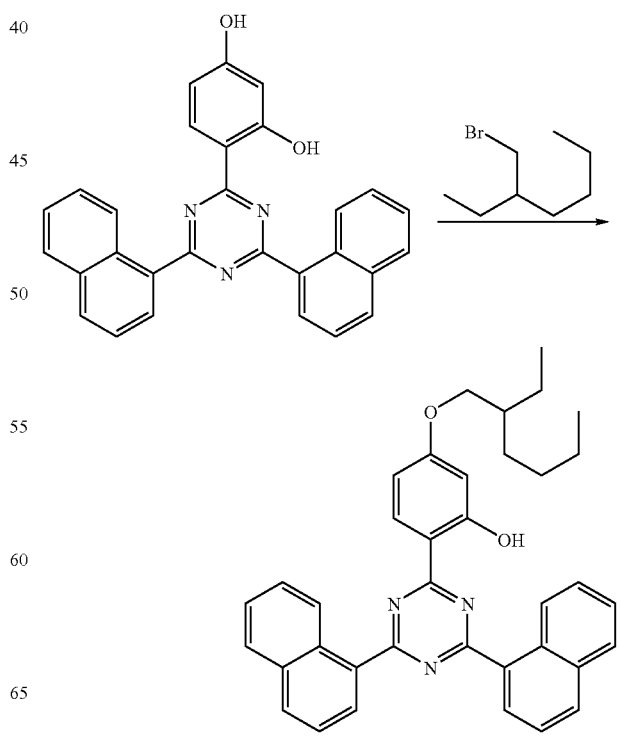

20.7 g of potassium carbonate and 21.2 g of ethylhexyl bromide are added to a solution of 44.1 g of the product from Example 1 in 50 ml of DMF. That reaction mixture is heated at 100° C. for 2 h, then poured onto ice-water and acidified with dilute hydrochloric acid. The aqueous phase is extracted with dichloromethane. The organic phase is washed repeatedly with water and then dried with magnesium sulfate. Chromatography on silica gel yields the product.

$^1$H-NMR (400 MHz, CDCl$_3$) δ: 13.2 (s, 1H); 9.27 (s broad, 2H); 8.61 (d, J=9.0 Hz, 1H); 8.35 (s broad, 2H); 8.08 (d, J=8.2 Hz, 2H) 7.97 (d, J=7.6 Hz, 2H); 7.58–7.69 (m, 6H); 6.61 (dd, J=2.3 Hz, J=9.0 Hz, 1H); 6.54 (d, J=2.3 Hz, 1H); 3.93 (d, J=5.6 Hz, 2H); 1.80–1.75 (m, 1H); 1.41–1.53 (m, 8H); 0.90–0.97 (m, 6H).

Example A4

Preparation of bis-α-(4-hydroxy-naphthyl)-(2,4-hydroxy-phenyl)-triazine

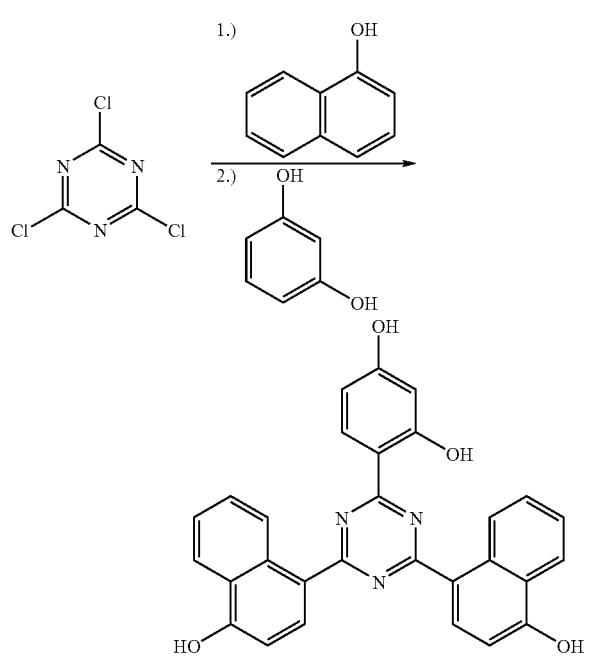

6.5 g of 36% hydrochloric acid are added dropwise at 0° C. under nitrogen to a suspension of 111 9 of aluminium chloride and 50.0 g of cyanuric chloride in 100 ml of 1,2-dichlorobenzene. The reaction mixture is then stirred for 1 h at 25° C. To that mixture there is added within 1.5 h a warmed solution of 74.2 g of α-naphthol in 200 ml of 1,2-dichlorobenzene. When the addition is complete, stirring is carried out for a further hour at 25° C. and for 1 h at 60° C. 32.8 g of resorcinol are added in portions to that reaction mixture at 60° C. After 2 h, the reaction mixture, which is then solid, is comminuted and the solid is filtered off. Dilute hydrochloric acid is added to the solid and the mixture is heated to boiling. The solid is filtered off. The product (or the hydrochloric acid addition product thereof) can be purified by treatment with ethyl methyl ketone.

Example A5

Preparation of bis-α-(4-hexyloxy-naphthyl)-(2,4-hexyloxy-phenyl)-triazine

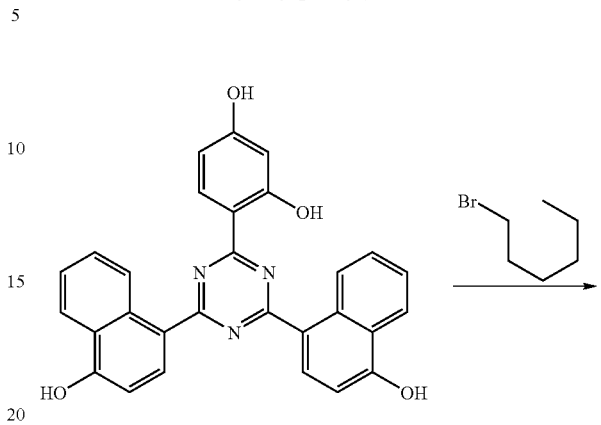

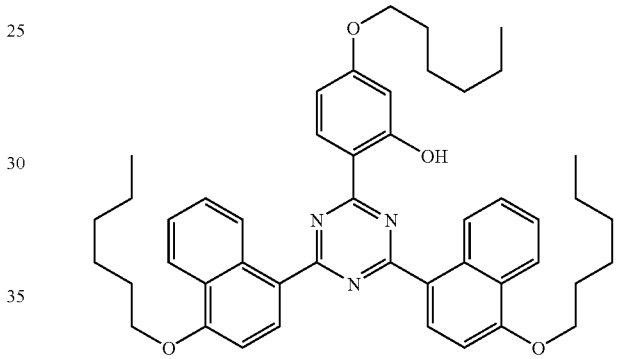

45.6 g (0.33 mol) of potassium carbonate and 27.2 g (0.165 mol) of hexyl bromide are added to a solution of 23.7 g (0.05 mol) of the product from Example 4 in 50 ml of DMF. That reaction mixture is heated at 110° C. for 2 h, then poured into ice-water and acidified with dilute hydrochloric acid. The aqueous phase is extracted with ethyl acetate. The organic phase is washed repeatedly with water and then dried with magnesium sulfate. Chromatography on silica gel yields the product:

$^1$H-NMR (300 MHz, CDCl$_3$) δ: 13.5 (s, 1H); 9.21 (s broad, 2H); 8.56 (d, J=9 Hz, 1H); 8.42 (s broad, superimposed), 8.41 (d, J=7.5 Hz, 2H); 7.63–7.50 (m, 4H); 6.88 (d, J=8.1 Hz, 2H); 6.58 (dd, J=2.4 Hz, J=9 Hz, 1H); 6.50 (d, J=2.1 Hz, 1H); 4.23 (t, 4H); 4.02 (t, 2H); 1.99–1.95 (m, 4H); 1.89–1.76 (m, 2H); 1.60–1.35 (m, 18 H); 0.96–0.92 (m, 9H).

Example A6

Preparation of bis-α-naphthyl-(2,4-dihydroxyphenyl)-triazine

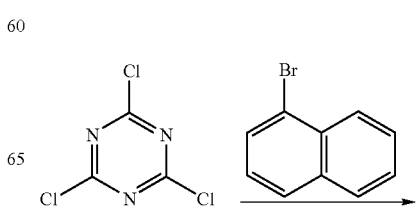

-continued

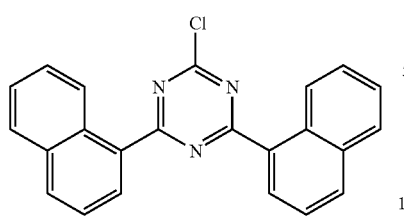

a) A solution of 50.0 g of 1-bromonaphthalene in 30 ml of tetrahydrofuran (THF) is added dropwise to a suspension of 5.59 g of magnesium in 10 ml of anhydrous THF. In the case of a delayed start to the reaction, a small quantity of iodine is added and heating is carried out until the reaction commences. When the addition is complete, 110 ml of THF are added to the reaction mixture and the resulting mixture is heated to boiling for 1 h. It is then cooled to 25° C. The resulting solution is added dropwise at 25° C. under nitrogen to a solution of 19.9 g of cyanuric chloride in 50 ml of THF, during which the temperature is maintained at from 20 to 25° C. When the addition is complete, the reaction mixture is heated at 50° C. for 16 h. It is then poured onto ice-water and acidified with hydrochloric acid. The aqueous phase is extracted with toluene and the organic phase is dried with magnesium sulfate. The solvent is removed under reduced pressure. The resulting product (41.9 g) is further reacted without further purification.

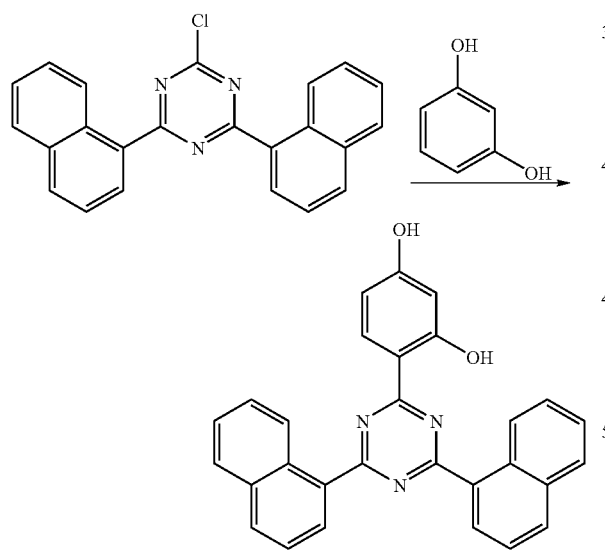

b) 16.7 g of aluminium chloride are added to a solution of 41.9 g of the above product in 100 ml of 1,2-dichlorobenzene and the reaction mixture is heated to 80° C. 13.8 g of resorcinol are added in portions to that mixture. The reaction mixture is stirred at 80° C. for a further 15 min and then heated at 130° C. for 3 h. The resulting reaction mass is poured onto ice and the resulting product is filtered off. The resulting product is dried under reduced pressure (in vac.)

Alternatively, the product is obtained analogously to Example 20 described in WO 00/29392.

Example A7

Preparation of bis-α-naphthyl-(2-hydroxy-4-[3-n-butoxy-2-hydroxy-propoxy]-phenyl)-triazine

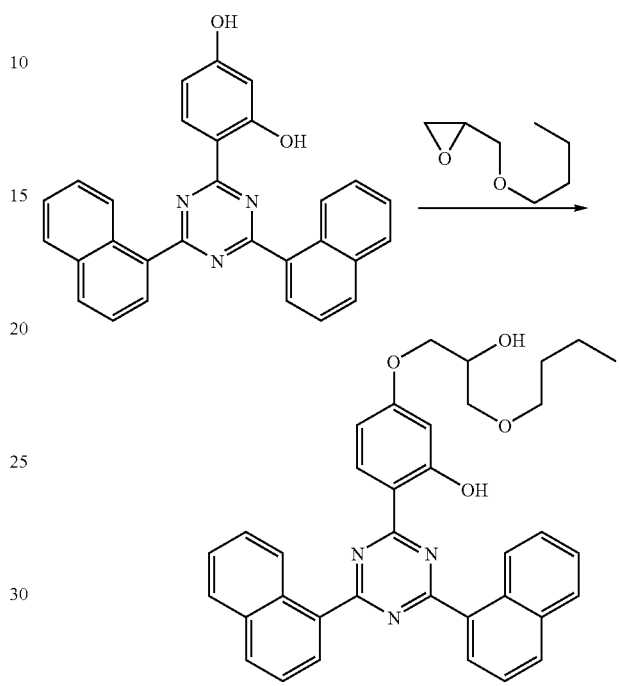

6.60 g of butyl-2,3-epoxypropyl ether and 0.78 g of ethyl-triphenyl-phosphonium bromide are added to a solution of 20.0 g of the product from Example A6 in 200 ml of xylene. That reaction mixture is heated to boiling for 18 h. 0.5 g of activated carbon is then added to the reaction mixture and the resulting mixture is stirred at 25° C. for 1 h. After filtration of the reaction mixture on Hyflo® (kieselguhr; Fluka 56678), the solvent is removed in vac. Chromatography of the residue on silica gel yields the product of melting point: 118–119° C.

Example A8

Bis-α-naphthyl-(4-[1-ethoxycarbonyl-ethoxy]-2-hydroxy-phenyl)-triazine

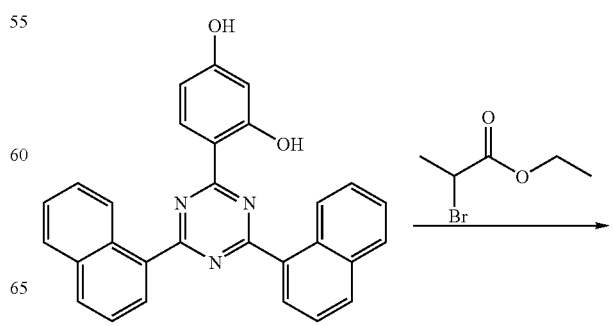

-continued

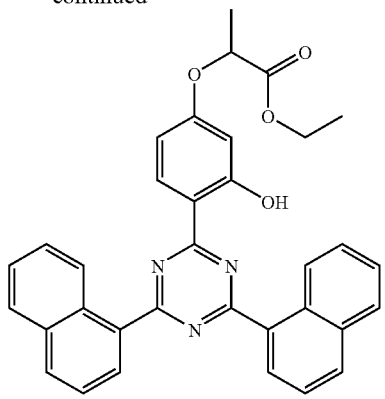

9.39 g of potassium carbonate and 9.02 g of 2-bromopropionic acid ethyl ester are added to a solution of 20.0 g of the product from Example A6 in 200 ml of DMF. The reaction mixture is heated at 125° C. for 3.5 h. The solid which precipitates is filtered off and washed with toluene. The combined organic phase is freed of solvent in vac. Chromatography of the residue on silica gel yields the product of melting point: 124–125° C.

Example A9

Preparation of bis-α-naphthyl-(4-[2-hydroxy-ethoxy]-2-hydroxy-phenyl)-triazine

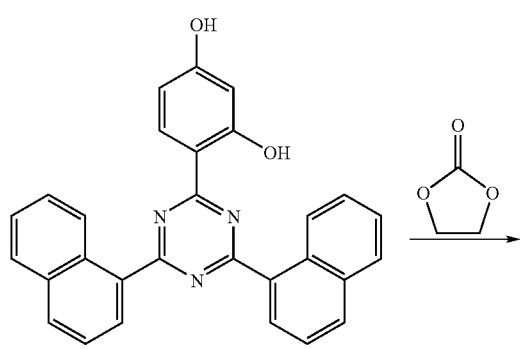

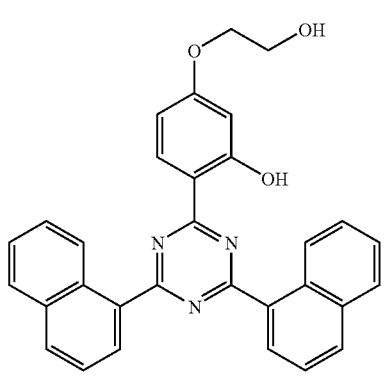

9.39 g of potassium carbonate and 4.39 g of ethylene carbonate are added to 20 g of the product from Example A6 in 200 ml of anhydrous DMF. The reaction mixture is heated at 140° C. for 18 h. The salts which precipitate are filtered off and washed with toluene. The combined organic phase is freed of solvent in vac. and used directly for the further reaction.

Example A10

Preparation of bis-α-naphthyl-(4-[2-acetoxy-ethoxy]-2-hydroxy-phenyl)-triazine

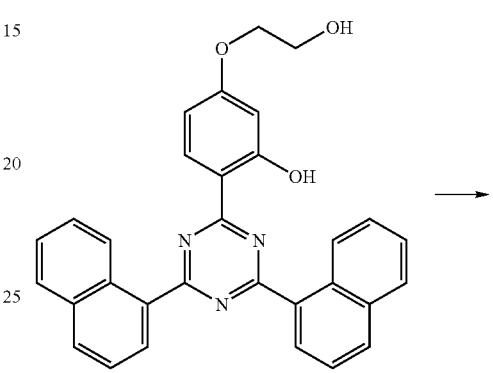

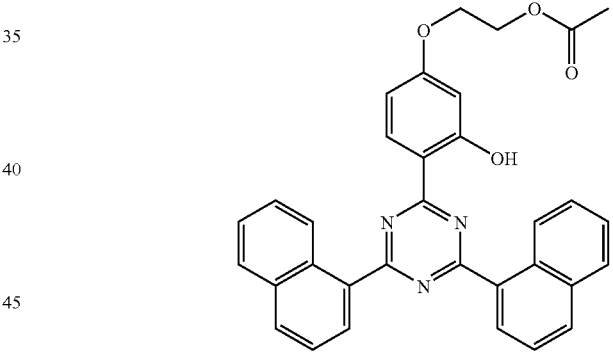

9.11 g of acetic anhydride, 18.1 g of triethylamine and 0.73 g of dimethylaminopyridine in 400 ml of anhydrous dichloromethane are added to the product from Example A9. The reaction mixture is heated to boiling. When the reaction is complete (monitoring by TLC), the solvent is removed in vac. and the residue is taken up in dichloromethane. The organic phase is washed with water and dried with magnesium sulfate. After removal of the solvent, the residue is chromatographed on silica gel, yielding the product having the following NMR data:

$^1$H-NMR (400 MHz, CDCl$_3$) δ: 13.3 (s, 1H); 9.02 (s broad, 2H); 8.63 (d, J=9.0 Hz, 1H); 8.45 (s broad, 2H); 8.08 (d, J=8.2 Hz, 2H); 7.97 (d, J=8.5 Hz, 2H); 7.56-7.67 (m, 6H); 6.64 (dd, J=2.5 Hz, J=9 Hz, 1H); 6.54 (d, J=2.5 Hz, 1H); 4.45–4.47 (m, 2H); 4.20–4.26 (m, 2H); 2.12 (s, 3H).

Example A11

Preparation of bis-α-(4-[1-ethoxycarbonyl-ethoxy]-naphthyl)-(4-[1-ethoxycarbonyl-ethoxy]-2-hydroxy-phenyl)-triazine

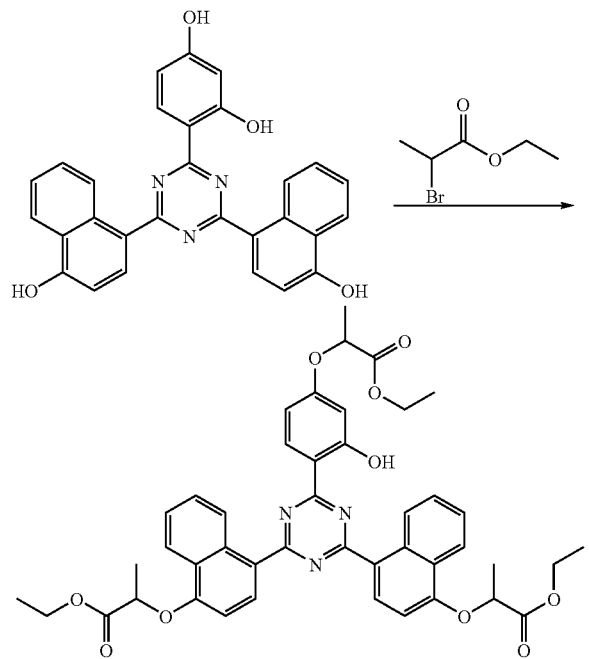

26.3 g of potassium carbonate and 25.2 g of 2-bromopropionic acid ethyl ester are added to a solution of 20.0 g of the product from Example A4 in 200 ml of DMF. That reaction mixture is heated at 125° C. for 3 h. The solid which precipitates is filtered off and washed with toluene. The combined organic phase is freed of solvent in vac. Chromatography on silica gel yields the product having the following NMR data:

¹H-NMR (300 MHz, CDCl₃) δ: 13.5 (s, 1H); 9.17 (s broad, 2H); 8.61 (d, J=9.0 Hz, 1H); 8.52 (d, J=8.2 Hz, 2H); 8.45 (s broad, superimposed), 7.69–7.57 (m, 4H); 6.84 (d, J=9.0 Hz, 2H); 6.62 (dd, J=2.4 Hz, J=8.9 Hz, 1H); 6.48 (d, J=2.4 Hz, 1H); 5.06 (q, J=6.7 Hz, 2H); 4.85 (q, J=6.6 Hz, 1H); 4.33–4.18 (m, 6H); 1.82 (d, J=6.7 Hz, 6H); 1.67 (d, J=6.8 Hz, 3H); 1.31–1.24 (m, 9H).

Example A12

Preparation of bis-α-(4-methyl-naphthyl)-(2,4-dihydroxyphenyl)-triazine

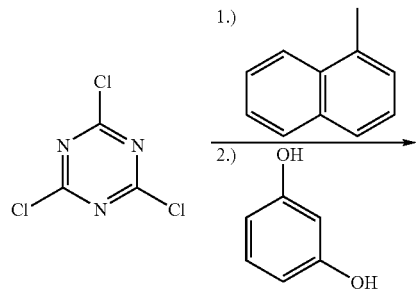

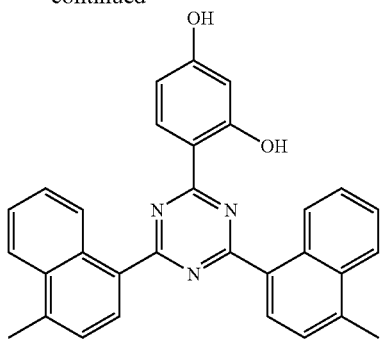

The product is prepared analogously to Example 20 described in Patent WO 00/29392 and is used for the subsequent reactions without further purification.

Example A13

Bis-α-(4-methyl-naphthyl)-(2-hydroxy-4-n-hexyloxy-phenyl)-triazine

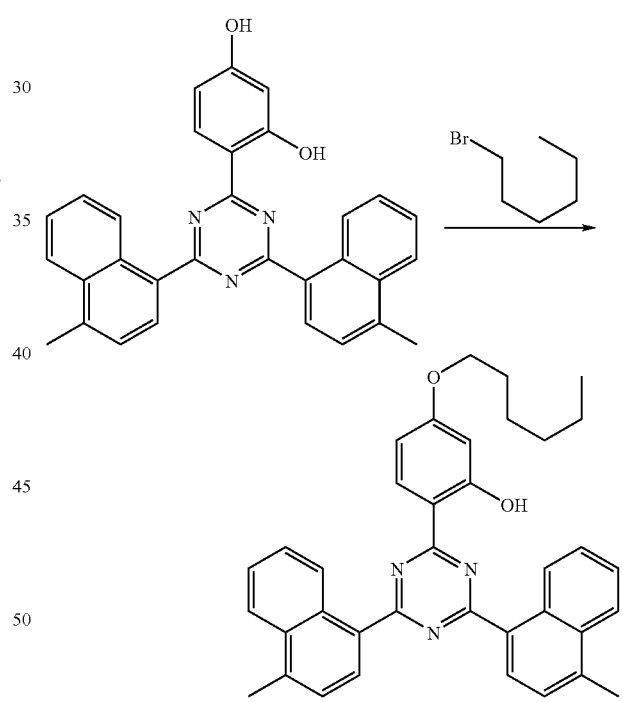

33.1 g of potassium carbonate and 29.0 g of hexyl bromide are added to a solution of 75.0 g of the product from Example A12 in 50 ml of DMF. That reaction mixture is heated at 120° C. for 3 h. The solid which precipitates is filtered off and washed with toluene. The combined organic phase is freed of solvent in vac. Chromatography on silica gel yields the title product having the following data:

¹H-NMR (300 MHz, CDCl₃) δ: 13.3 (s, 1H); 9.06 (s broad, 2H); 8.59 (d, J=9.0 Hz, 1H); 8.32 (s broad, 2H); 8.11–8.14 (m, 2H); 7.59–7.64 (m, 4H); 6.59 (dd, J=2.4 Hz, J=9.3 Hz, 1H); 6.52 (d, J=2.3 Hz, 1H); 4.03 (t, J=6.6 Hz, 2H); 2.80 (s, 6H); 1.79–1.83 (m, 2H); 1.32–1.47 (m, 2H); 1.33–1.37 (m, 4H); 0.92 (t, J=7.0 Hz, 3H).

Example A14

α-(2-Methoxy-naphthyl)-α-(2-hydroxy-naphthyl)-(2-hydroxy-4-n-hexyloxyphenyl)-triazine

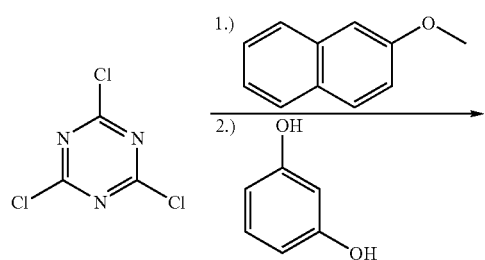

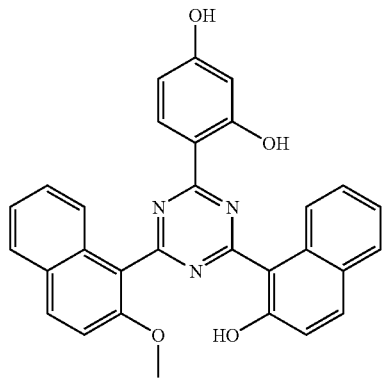

a) 9.4 g of 36% hydrochloric acid are added dropwise at 0° C. under nitrogen to a suspension of 152 g of aluminium chloride and 70.0 g of cyanuric chloride in 300 ml of 1,2-dichlorobenzene. The reaction mixture is then stirred at 25° C. for a further 1 h. To that mixture there are added within 4 h 108 g of β-methoxy-naphthalene in 150 ml of 1,2-dichlorobenzene. When the addition is complete, the reaction mixture is stirred at 25° C. for a further 3 h. 41.8 g of resorcinol are added in portions to that reaction mixture at 50° C. The reaction mixture is stirred for 1 h, the temperature being increased from 65° C. to 90° C. The solid reaction mixture is then hydrolysed with ice-water. The crude product is filtered off, dried at 110° C. in vac. and used for the further reaction without further purification.

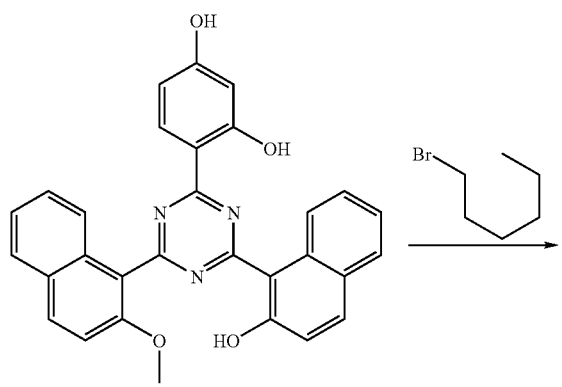

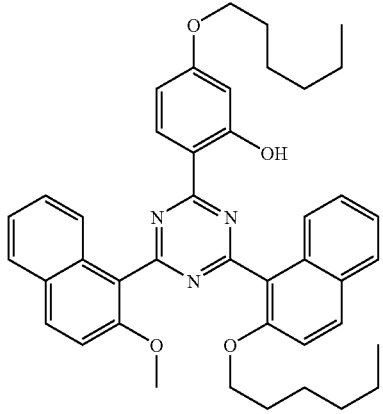

b) 41.5 g of potassium carbonate and 36.3 g of hexyl bromide are added to a mixture of 75.0 g of the crude product from step a) in 600 ml of DMF. That reaction mixture is heated at 125° C. for 3 h. The solid which precipitates is filtered off and washed with toluene. The combined organic phase is freed of solvent in vac. Chromatography on silica gel and subsequent crystallisation yield the title product having the following data:

$^1$H-NMR (300 MHz, CDCl$_3$) δ: 13.2 (s, 1H); 8.49 (d, J=8.6 Hz, 1H); 7.98–7.72 (m, 6H); 7.30–7.48 (m, 6H); 6.48–6.56 (m, 2H); 4.15 (t, J=6.6 Hz, 2H); 4.01 (t, J=6.6 Hz, 2H); 3.98 (s, 3H); 1.85–1.65 (m, 4H); 1.10–1.50 (m, 12H); 0.90–0.92 (m, 3H); 0.74–0.78 (m, 3H).

Example A15

2,4-Bis-α-(2-methoxynaphthyl)-6-(2-hydroxy-4-n-hexyloxy-phenyl)-1,3,5-triazine

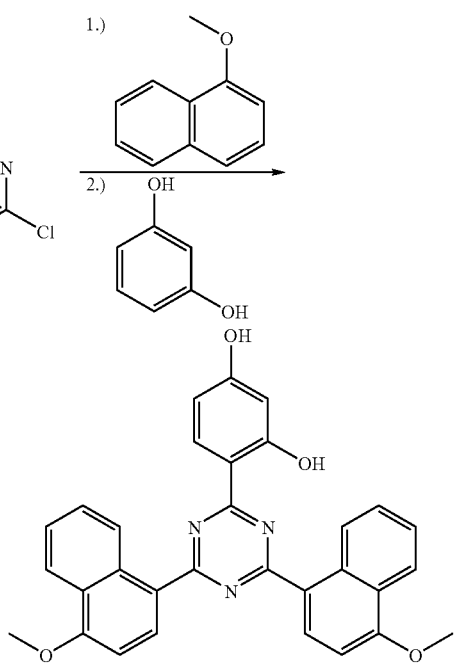

a) The product is prepared analogously to Example 18 described in patent WO 00/29392 and is used for the subsequent reactions without further purification.

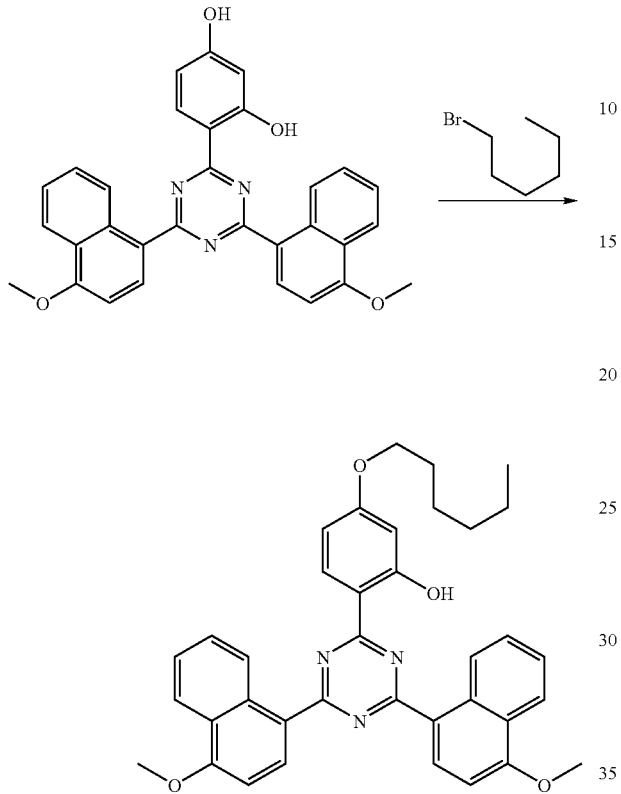

b) 41.3 g of potassium carbonate and 37.0 g of hexyl bromide are added to a mixture of 75.0 g of the above crude product in 600 ml of DMF. That reaction mixture is heated at 125° C. for 3 h. The solid which precipitates is filtered off and washed with toluene. The combined organic phase is freed of solvent in vac. Chromatography on silica gel and subsequent HPLC chromatography yield the title product having the following data:

$^1$H-NMR (400 MHz, CDCl$_3$) δ: 13.5 (s, 1H); 9.22 (s, broad, 2H); 8.61 (d, J=9.1 Hz, 1H); 8.45 (s, broad, 2H); 8.42 (d, J=9.2 Hz, 2H); 7.55–7.67 (m, 4H); 7.00 (d, J=8.3 Hz, 2H); 6.61 (dd, J=2.4 Hz, J=8.9 Hz, 1H); 6.54 (d, J=2.4 Hz, 1H); 4.12 (s, 6 H); 4.03 (t, J=6.6 Hz, 2H); 1.77–1.84 (m, 2H); 1.35–1.55 (m, 6H); 0.90–0.94 (m, 3H).

Example A16

Preparation of bis-chloro-α-naphthyl-triazine

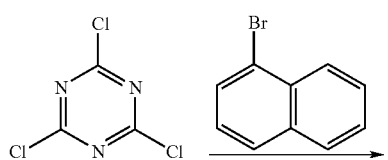

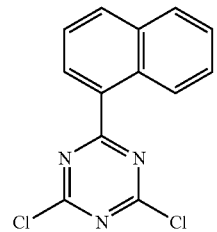

A solution of 228 g of 1-bromonapthalene in 250 ml of THF is added dropwise to a suspension of 28.0 g of magnesium in 100 ml of anhydrous THF in such a manner that the reaction temperature remains at from 50 to 65° C. In the case of a delayed start to the reaction, a small quantity of iodine is added and heating is carried out until the reaction commences. When the addition is complete, the reaction mixture is heated to boiling for 15 min. It is then cooled to 25° C.

The resulting solution is added dropwise at 25° C. under nitrogen to a solution of 193.6 g of cyanuric chloride in 500 ml of THF. During that procedure, the reaction temperature is maintained at from 20 to 25° C. When the addition is complete, the reaction mixture is stirred at 25° C. for a further 2 h and is then poured into ice-water and acidified with hydrochloric acid. The product is filtered off and washed with water. Crystallisation from toluene yields the title product of melting point: 165–170° C.

Example A17

Preparation of bis-(2,4-dihydroxyphenyl)-α-naphthyl-triazine

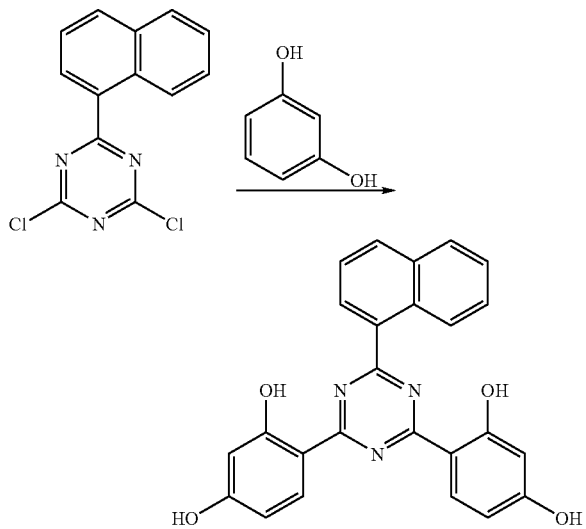

56.3 g of aluminium chloride and 120 ml of a petroleum fraction of boiling range 110–160° C. are added to 50.0 g of the product from Example A16. 150 ml of sulfolane are added to that mixture, the reaction mixture warming to 45° C.

To that mixture there is added dropwise at 40° C. a solution of 49.8 g of resorcinol in 60 ml of sulfolane. After 1 h, the reaction mixture is heated at 80° C. for 5 h and then 850 ml of methanol and 300 ml of water are added thereto. The product is filtered off, 880 ml of 36% hydrochloric acid are added thereto and the mixture is heated to boiling for 1 h. After cooling to 25° C., the product is filtered off again and washed with water. Drying in vac. yields the desired product having a melting point above 280° C.

$^1$H-NMR (300 MHz, CDCl$_3$) δ: 13.0 (s,2H); 10.5 (s,2H), 8.67–8.63 (m, 1H), 8.31 (d, J=8.9 Hz, 2H), 8.24–8.07 (m, 3H), 7.75–7.60 (m, 3H), 6.52 (dd, J=2.3 Hz, J=8.9 Hz, 2H), 6.36 (d, J=2.3 Hz, 2H).

Example A18

α-Naphthyl-bis-(2-hydroxy-4-[3-n-butoxy-2-hydroxy-propoxy]-phenyl)-triazine

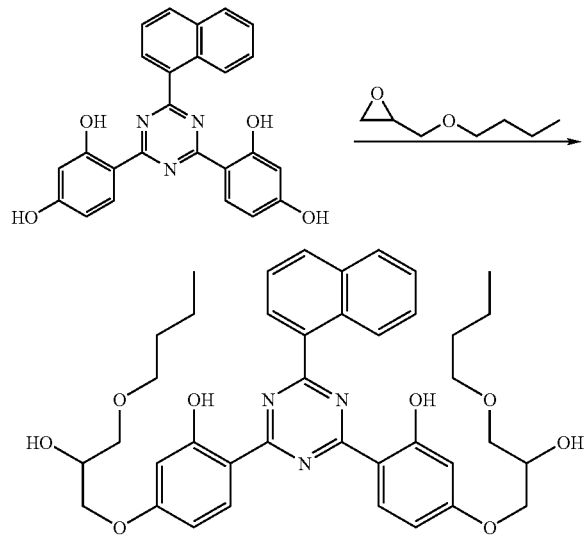

11.1 ml of butyl-2,3-epoxypropyl ether and 1.3 g of ethyl-triphenyl-phosphonium bromide are added to 15.0 g of the product from Example A17 in 70 ml of mesitylene. That reaction mixture is heated at 150° C. for 18 h. 0.5 g of activated carbon is then added and the mixture is stirred at 25° C. for 1 h. After filtration on Hyflo® (kieselguhr; Fluka 56678), the solvent is removed in vac. Chromatography on silica gel yields the title product.

| elemental analysis: | | | | | |
|---|---|---|---|---|---|
| calculated: | % C | 68.50 | found: | % C | 68.22 |
| | % H | 6.63 | | % H | 6.63 |
| | % N | 6.15 | | % N | 6.05 |

Example A19

Preparation of bis-chloro-α-(4-methoxyl-naphthyl)-triazine

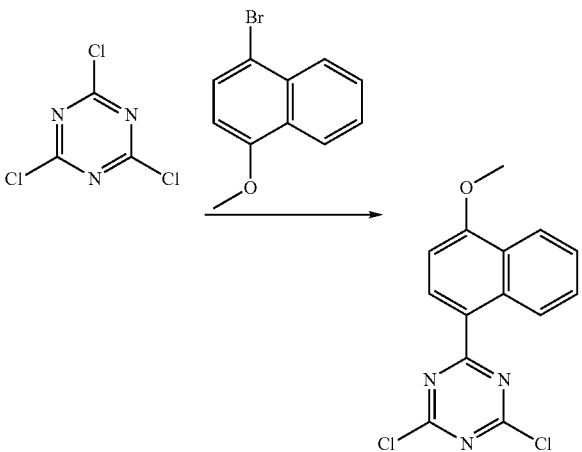

A solution of 299 g of 1-bromo-4-methoxy-naphthalene in 190 ml of tetrahydrofuran (THF) is added dropwise to a suspension of 33.7 g of magnesium in 126 ml of anhydrous THF in such a manner that the reaction temperature remains at from 60 to 65° C. In the case of a delayed start to the reaction, a small quantity of iodine is added and heating is carried out until the reaction commences. When the addition is complete, the reaction mixture is heated to boiling for a further 1 h. It is then cooled to 25° C. The resulting solution is added dropwise at 25° C. under nitrogen to a solution of 221 g of cyanuric chloride in 630 ml of THF. During that procedure, the reaction temperature is maintained at from 20 to 25° C. When the addition is complete, the reaction mixture is stirred at 25° C. for a further 18 h. The reaction mixture is then poured into ice-water and acidified with hydrochloric acid. The product is filtered off, washed with water and recrystallised from toluene; melting point: 142–145° C.

Example A20

Preparation of bis(2,4-dihydroxyphenyl)-α-(4-methoxyl-naphthyl)-triazine

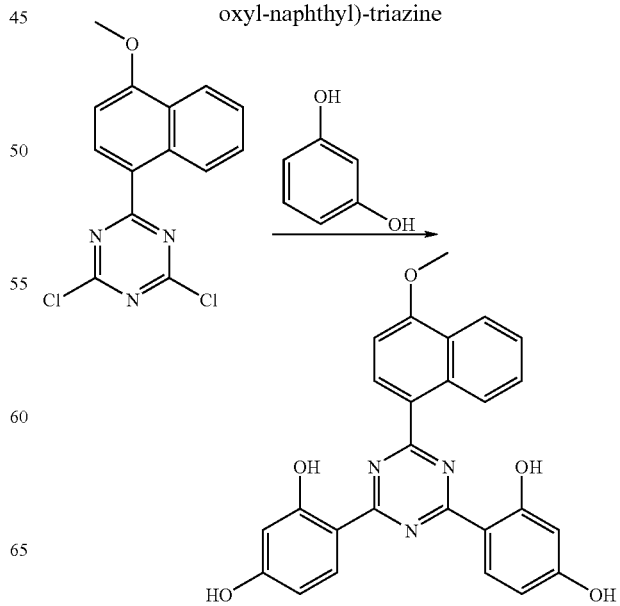

241 g of aluminium chloride and 450 ml of a petroleum fraction of boiling range 110–140° C. are added to 213 g of the product from Example A19. 635 ml of sulfolane are added to that mixture, the reaction mixture warming to 60° C.

To that mixture there is added dropwise at 45° C. a solution of 216 g of resorcinol in 270 ml of sulfolane; the reaction mixture is then heated at 85° C. for 5 h and then poured into a mixture of 3000 ml of methanol and 3500 ml of ice-water. The product is filtered off and washed with water. Drying in vac. yields the title product of melting point 310–316° C.

Example A21

α-(4-Methoxy-naphthyl)-bis(2-hydroxy-4-[3-n-butoxy-2-hydroxy-propoxy]-phenyl)-triazine

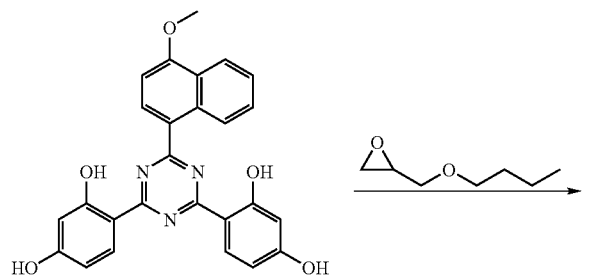

12.6 g of butyl-2,3-epoxypropyl ether and 1.6 g of ethyl-triphenyl-phosphonium bromide are added to 20.0 g of the product from Example A20 in 90 ml of mesitylene. That reaction mixture is heated at 150° C. for 20 h. 0.5 g of activated carbon is then added and the mixture is stirred at 25° C. for 1 h. After filtration on Hyflo® (kieselguhr; Fluka 56678), the solvent is removed in vac. Chromatography on silica gel yields the title product.

| elemental analysis: | | | | | |
|---|---|---|---|---|---|
| calculated: | % C | 67.30 | found: | % C | 66.85 |
| | % H | 6.64 | | % H | 6.50 |
| | % N | 8.89 | | % N | 5.87 |

Example A22

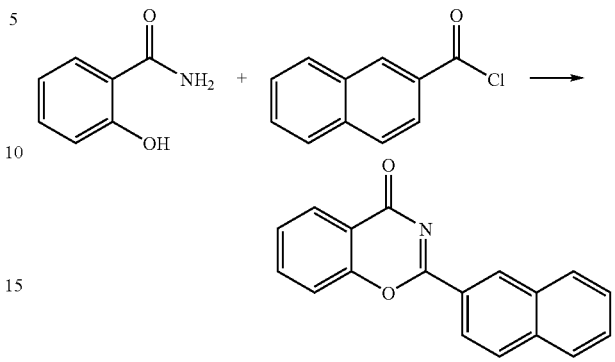

In a sulfonating flask with water separator, 6.04 g of salicylic acid amide in 30 ml of dry xylene and 0.5 g of pyridine are heated to reflux. A solution of 10.58 g of 2-naphthoyl chloride in 30 ml of xylene is added dropwise within 1.5 h. The mixture is maintained at reflux temperature until no more water is separated. The reaction mixture is concentrated by evaporation and degassed at 130° C. under a water-jet vacuum. 14 g of the benzoxazinone intermediate is obtained in the form of a colourless resin which is further processed without purification.

Example A23

2-(2-Hydroxyphenyl)-4-(β-naphthyl)-6-(4-phenylphenyl)-1,3,5-triazine

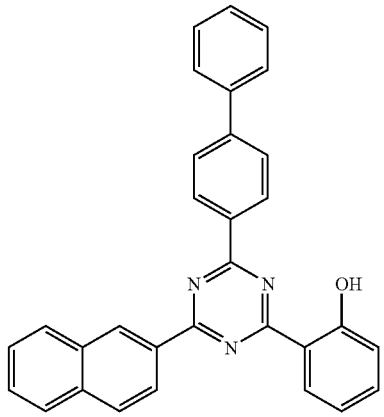

7 g of the product from Example A22 (22 mmol) are heated to 60° C. with 6 g (26 mmol) of 4$$ -phenyl-benzamidinium hydrochloride in 200 ml of methanol. Then 5 g of sodium methanolate (30% in methanol; 28 mmol) are added; stirring is then carried out at 60C for 1 hour, followed by cooling, filtration, and washing twice with 50 ml of methanol each time, to yield 4.16 g of the title product in the form of a white powder, melting range 227–239° C.

Recrystallisation from 150 ml of dimethylformamide and subsequent washing with methanol yield 3.34 g of the purified end product.

Elemental analysis:
calculated: 82.46% C; 4.69% H; 9.31% N found: 82.24% C; 4.68% H; 9.27% N
λmax (CHCl₃)=271 nm.

Example A24

2-(2-Hydroxyphenyl)-4-(β-naphthyl)-6-phenyl-1,3,5-triazine

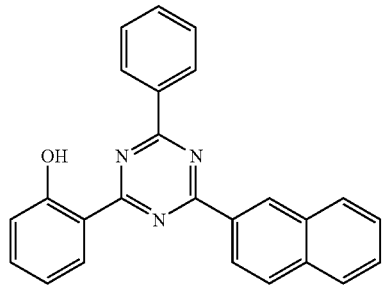

Analogously to the process in Example A23, 3.12 g of the title product are obtained using an equivalent amount of benzamidinium hydrochloride in place of 4-phenyl-benzamidinium hydrochloride.

Elemental analysis:
calculated: 78.14% C; 4.72% H; 10.94% N
found: 79.98% C; 4.56% H; 11.19% N
λmax (CHCl₃)=271 nm.

B: EXAMPLES OF USE

The following UVAs according to the invention of formula I are used:

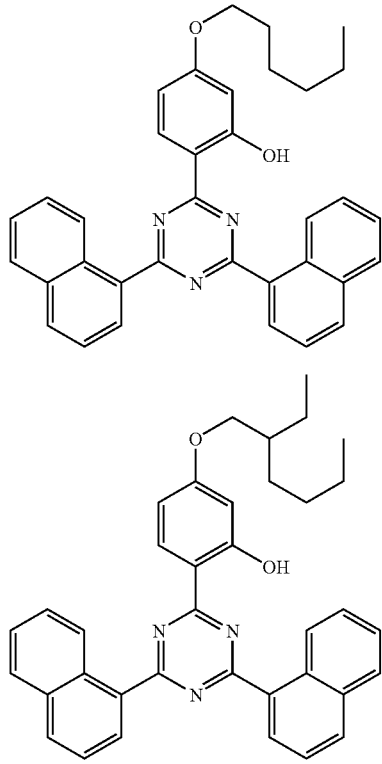

A2

A3

As explained above, the compositions according to the invention may comprise, in addition, one or more known UVAs. In the Examples, the following compounds inter alia are used:

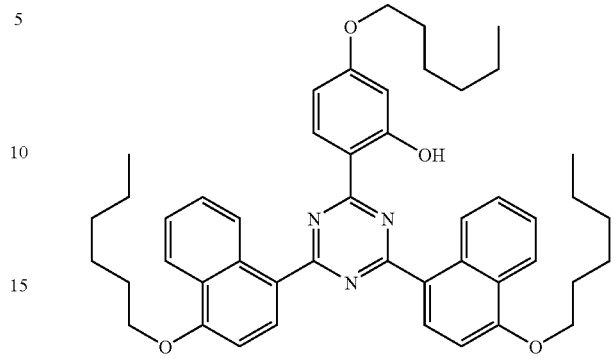

A5

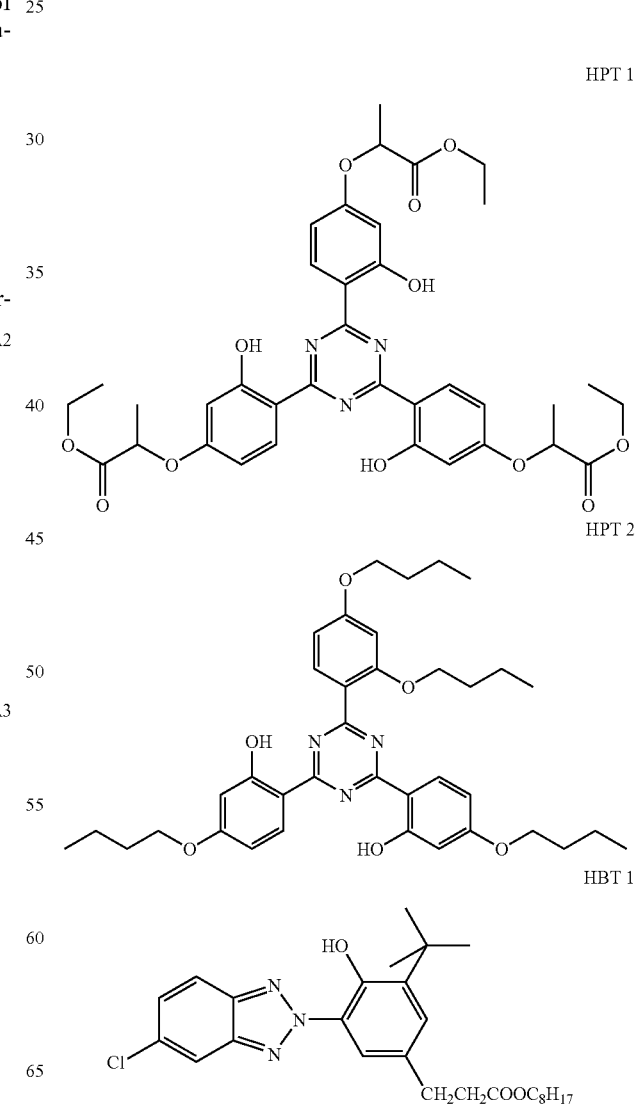

HPT 1

HPT 2

HBT 1

-continued

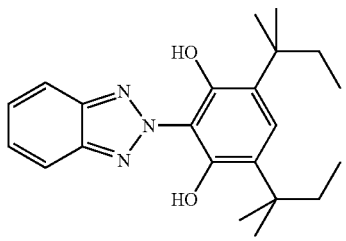

HBT 2

Example B1

A gelatin layer of the following composition (per $m^2$) is applied in the usual manner to a polyester support:

| component: | amount: |
|---|---|
| gelatin | 1200 mg |
| tricresyl phosphate | 150 mg |
| curing agent | 40 mg |
| wetting agent | 100 mg |
| compound of formula I | 300 mg |

The potassium salt of 2-hydroxy-4,6-dichloro-1,3,5-triazine is used as curing agent, and sodium 4,8-diisobutyl-naphthalene-2-sulfonate is used as wetting agent.

The gelatin layers are dried at 20° C. for 7 days. When compounds 1 to 3 according to the invention are used, clear transparent layers are obtained which are suitable for a photographic recording material, for example as a UV filter layer.

The long-wave absorption maximum ($\lambda_{max}$), and the optical density at $\lambda_{max}$ ($OD_{max}$), of the UV filter layers so produced are measured with a Lambda 15 spectrophotometer produced by Perkin-Elmer. The results are given in the following Table.

| sample | UVA according to the invention from Example: | $\lambda_{max}$ | $OD_{max}$ |
|---|---|---|---|
| 1-1 | A2 | 347.0 | 1.48 |
| 1-2 | A3 | 346.6 | 1.39 |
| 1-3 | A5 | 357.0 | 1.23 |

Example B2

The procedure is the same as that described in Example B1 but with the use of a mixture of a compound according to the invention and a second UV absorber (UVA) not according to the invention and shown in the following Table.

Clear transparent layers are obtained which are suitable for a photographic recording material, for example as a UV filter layer.

The long-wave absorption maximum ($\lambda_{max}$), and the optical density at $\lambda_{max}$ ($OD_{max}$), of the UV filter layers so produced are measured with a Lambda 15 spectrophotometer produced by Perkin-Elmer. The results are given in the following Table.

| sample | UVA mixture | mass ratio | $\lambda_{max}$ | $OD_{max}$ |
|---|---|---|---|---|
| 2-1 | A2/HBT-1 | 70/30 | 348.2 | 2.00 |
| 2-2 | A2/HBT-2 | 50/50 | 347.1 | 1.21 |
| 2-3 | A2/HPT-1 | 70/30 | 350.0 | 1.47 |
| 2-4 | A2/HPT-2 | 50/50 | 345.0 | 1.79 |
| 2-5 | A3/HBT-1 | 70/30 | 348.3 | 1.81 |
| 2-6 | A3/HBT-2 | 50/50 | 347.4 | 1.18 |
| 2-7 | A3/HPT-1 | 70/30 | 349.3 | 1.37 |
| 2-8 | A3/HPT-2 | 50/50 | 346.0 | 1.73 |
| 2-9 | A5/HBT-1 | 70/30 | 355.2 | 1.29 |
| 2-10 | A5/HBT-2 | 50/50 | 352.1 | 1.24 |
| 2-11 | A5/HPT-1 | 70/30 | 356.6 | 1.37 |
| 2-12 | A5/HPT-2 | 50/50 | 348.6 | 1.56 |

Example B3

UV filter layers are produced as described in Examples B1 and B2. The corresponding samples are exposed with 60 kJ/cm$^2$ in an Atlas exposure apparatus and the decrease in density at the long-wave absorption maximum ($\lambda_{max}$) is determined. The results are listed in the following Table.

| sample | UVA of formula I | other UVA | mass ratio | $\lambda_{max}$ | decrease in density |
|---|---|---|---|---|---|
| 3-1 | A2 | — | — | 347.0 | 5% |
| 3-2 | A3 | — | — | 346.6 | 7% |
| 3-3 | A2 | HBT-1 | 70/30 | 348.2 | 4% |
| 3-4 | A2 | HBT-2 | 50/50 | 347.1 | 8% |
| 3-5 | A2 | HPT-1 | 70/30 | 350.0 | 4% |
| 3-6 | A2 | HPT-2 | 50/50 | 345.0 | 3% |
| 3-7 | A3 | HBT-1 | 70/30 | 348.3 | 6% |
| 3-8 | A3 | HBT-2 | 50/50 | 347.4 | 8% |
| 3-9 | A3 | HPT-1 | 70/30 | 349.3 | 7% |
| 3-10 | A3 | HPT-2 | 50/50 | 346.0 | 6% |

Example B4

UV filter layers are produced as described in Examples B1 and B2. The corresponding samples are stored in a climatic test cabinet at 80° C. and 70% humidity for 14 days and the decrease in density at the long-wave absorption maximum ($\lambda_{max}$) is determined. The results are listed in the following Table.

| sample | UVA according to the invention | other UVA | mass ratio | $\lambda_{max}$ | decrease in density |
|---|---|---|---|---|---|
| 4-1 | — | HBT-2 | — | 347.6 | 30% |
| 4-2 | A2 | — | — | 347.0 | <1% |
| 4-3 | A3 | — | — | 346.6 | <1% |
| 4-4 | A5 | — | — | 358.8 | 4% |
| 4-5 | A2 | HBT-1 | 70/30 | 348.2 | 1% |
| 4-7 | A2 | HPT-1 | 70/30 | 350.0 | 1% |
| 4-8 | A2 | HPT-2 | 50/50 | 345.0 | 2% |
| 4-9 | A3 | HBT-1 | 70/30 | 348.3 | 2% |
| 4-11 | A3 | HPT-1 | 70/30 | 349.3 | <1% |
| 4-12 | A3 | HPT-2 | 50/50 | 346.0 | 1% |
| 4-13 | A5 | HBT-1 | 70/30 | 355.2 | 2% |
| 4-14 | A5 | HBT-2 | 50/50 | 352.1 | 8% |
| 4-15 | A5 | HPT-1 | 70/30 | 356.6 | <1% |
| 4-16 | A5 | HPT-2 | 50/50 | 348.6 | 1% |

Example B5

The procedure is the same as that described in Example B1 but with the compounds according to the invention being employed in such a manner that a filter of optical density 2.0 (measured at the long-wave absorption maximum $\lambda_{max}$) is obtained. Clear, transparent layers are obtained which are suitable for a photographic recording material. The required total amount of UVA is listed in the following Table. sample UVA total amount

| sample | UVA | total amount |
|---|---|---|
| 5-1 | A2 | 400 mg/m² |
| 5-2 | A3 | 420 mg/m² |

Example B6

Chromogenic emulsions having the following components are applied in the usual manner to a support material coated with polyethylene (amounts given per m² in each case):

| sample | coupler | oil | gelatin | curing agent | wetting agent | silver agent |
|---|---|---|---|---|---|---|
| 6-1 | M-1 253 mg | TCP 253 mg | 5.15 g | 300 mg | 85 mg | 260 mg |
| 6-2 | M-2 293 mg | TCP 586 mg | 5.15 g | 300 mg | 85 mg | 260 mg |
| 6-3 | M-3 417 mg | TCP 208 mg | 5.15 g | 300 mg | 85 mg | 520 mg |
| 6-4 | Y-1 835 mg | DBP 278 mg | 5.15 g | 300 mg | 340 mg | 520 mg |

TCP = tricresyl phosphate;
DBP = dibutyl phthalate

The couplers used correspond to the formulae:

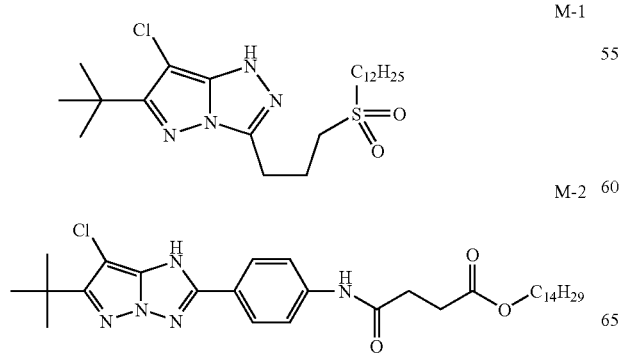

M-1

M-2

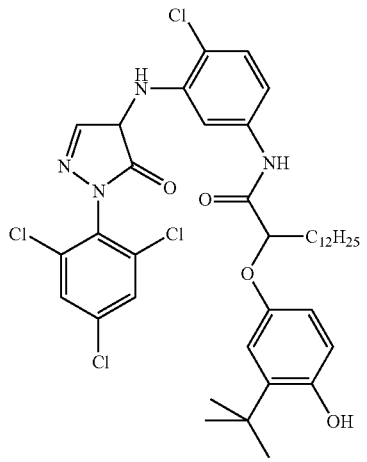

M-3

The potassium salt of 2,4-dichloro-6-hydroxytriazine is used as curing agent, and the sodium salt of diisobutylnaphthalenesulfonic acid is used as wetting agent.

The layers are dried at 20° C. for 7 days.

A step wedge having a density difference of 0.3 log E per step is exposed onto each of the layers so obtained and is then processed in the Agfa P-94 processing process for negative colour papers according to the manufacturers instructions.

The samples so produced are exposed behind UV filters produced in accordance with Example B3 and B5, in an Atlas exposure apparatus. Before and after exposure, the reflection density is measured (in the green region for magenta layers and in the blue region for yellow layers). The results for an initial density of 1.0 are entered in the following Table. Samples having filter layers not containing any UVA (-) and samples having filter layers containing only the conventional HBT-2 compounds (*) are used as comparisons.

TABLE B6

Decrease in colour density after exposure

| layer from Example | UV filter from Example | exposure at | decrease in density |
|---|---|---|---|
| 6-1 | — | 15 kJ/cm² | 46% |
| 6-1 | 5-1 | 15 kJ/cm² | 30% |
| 6-1 | 5-2 | 15 kJ/cm² | 31% |
| 6-2 | — | 22.5 kJ/cm² | 49% |
| 6-2 | 3-1* | 22.5 kJ/cm² | 30% |
| 6-2 | 3-2 | 22.5 kJ/cm² | 24% |
| 6-2 | 3-3 | 22.5 kJ/cm² | 25% |
| 6-2 | 3-4 | 22.5 kJ/cm² | 24% |
| 6-2 | 3-5 | 22.5 kJ/cm² | 23% |
| 6-2 | 3-6 | 22.5 kJ/cm² | 25% |
| 6-2 | 3-7 | 22.5 kJ/cm² | 22% |
| 6-2 | 3-8 | 22.5 kJ/cm² | 25% |
| 6-2 | 3-9 | 22.5 kJ/cm² | 22% |
| 6-2 | 3-10 | 22.5 kJ/cm² | 27% |
| 6-2 | 5-1 | 22.5 kJ/cm² | 22% |
| 6-2 | 5-2 | 22.5 kJ/cm² | 22% |
| 6-3 | — | 22.5 kJ/cm² | 53% |
| 6-3 | 3-1* | 22.5 kJ/cm² | 34% |
| 6-3 | 3-2 | 22.5 kJ/cm² | 29% |
| 6-3 | 3-3 | 22.5 kJ/cm² | 29% |
| 6-3 | 3-4 | 22.5 kJ/cm² | 23% |
| 6-3 | 3-5 | 22.5 kJ/cm² | 28% |

TABLE B6-continued

Decrease in colour density after exposure

| layer from Example | UV filter from Example | exposure at | decrease in density |
|---|---|---|---|
| 6-3 | 3-6 | 22.5 kJ/cm$^2$ | 28% |
| 6-3 | 3-7 | 22.5 kJ/cm$^2$ | 26% |
| 6-3 | 3-8 | 22.5 kJ/cm$^2$ | 25% |
| 6-3 | 3-9 | 22.5 kJ/cm$^2$ | 28% |
| 6-3 | 3-10 | 22.5 kJ/cm$^2$ | 30% |
| 6-3 | 5-1 | 22.5 kJ/cm$^2$ | 24% |
| 6-3 | 5-2 | 22.5 kJ/cm$^2$ | 25% |
| 6-4 | — | 15 kJ/cm$^2$ | 43% |
| 6-4 | 3-1* | 15 kJ/cm$^2$ | 23% |
| 6-4 | 3-2 | 15 kJ/cm$^2$ | 21% |
| 6-4 | 3-3 | 15 kJ/cm$^2$ | 21% |
| 6-4 | 3-4 | 15 kJ/cm$^2$ | 17% |
| 6-4 | 3-5 | 15 kJ/cm$^2$ | 19% |
| 6-4 | 5-1 | 15 kJ/cm$^2$ | 19% |
| 6-4 | 5-2 | 15 kJ/cm$^2$ | 18% |

Example B7

A photographic material having the following layer structure is produced:

```
top layer
red-sensitive layer
second gelatin intermediate layer
green-sensitive layer
first gelatin intermediate layer
blue-sensitive layer
polyethylene support
```

The gelatin layers consist of the following components (per m$^2$ of support material):

Blue-Sensitive Layer
α-(3-benzyl-4-ethoxyhydantoin-1-yl)-α-pivaloyl-2-chloro-5-[α-(2,4-di-tert-amylphenoxy)butanamido]acetanilide (400 mg)
α-(1-butyl-phenylurazol-4-yl)-α-pivaloyl-5-(3-dodecanesulfonyl-2-methylpropanamido)-2-methoxyacetamide (400 mg)
dibutyl phthalate (130 mg)
dinonyl phthalate (130 mg)
gelatin (1200 mg)
1,5-dioxa-3-ethyl-3-[β-(3,5-di-tert-butyl-4-hydroxyphenyl)-propionyloxymethyl]-8,10-diphenyl-9-thia-[5,5]spiroundecane (150 mg)
bis(1-acryloyl-2,2,6,6-tetramethyl-4-piperidyl)-2,2-bis(3,5-di-tert-butyl-4-hydroxybenzyl)-malonate (150 mg)
3,5-di-tert-butyl-4-hydroxy-(2,4-di-tert-amylphenyl)-benzoate (150 mg)
poly(N-tert-butylacrylamide) (50 mg)
blue-sensitive silver chlorobromide emulsion (240 mg)

First Gelatin Intermediate Layer
gelatin (1000 mg)
2,5-di-tert-octylhydroquinone (100 mg)
5-[2,5-dihydroxy-4-(4-hexyloxycarbonyl-1,1-dimethylbutyl)-phenyl]-5-methylhexanoic acid hexyl ester (100 mg)
dibutyl phthalate (200 mg)
diisodecyl phthalate (200 mg)

Green-Sensitive Layer
7-chloro-2-{2-[2-(2,4-di-tert-amylphenoxy)octanamido]-1-methylethyl}-6-methyl-1H-pyrazolo[1,5-b][1,2,4]triazole (100 mg)
6-tert-butyl-7-chloro-3-(3-dodecanesulfonylpropyl)-1H-pyrazolo[5,1-o][1,2,4]triazole (100 mg)
dibutyl phthalate (100 mg)
dicresyl phosphate (100 mg)
trioctyl phosphate (100 mg)
gelatin (1400 mg)
3,3,3',3'-tetramethyl-5,5',6,6'-tetrapropoxy-1,1'-spirobiindane (100 mg)
4-(iso-tridecyloxyphenyl)thiomorpholine-1,1-dioxide (100 mg)
4,4'-butylidene-bis(3-methyl-6-tert-butylphenol) (50 mg)
2,2'-isobutylidene-bis(4,6-dimethylphenol) (10 mg)
3,5-dichloro-4-(hexadecyloxycarbonyloxy)ethyl benzoate (20 mg)
3,5-bis[3-(2,4-di-tert-amylphenoxy)propylcarbamoyl]sodium benzenesulfinate (20 mg)
green-sensitive silver chlorobromide emulsion (150 mg)

Second Gelatin Intermediate Layer
gelatin (1000 mg)
5-chloro-2-(3,5-di-tert-butyl-2-hydroxyphenyl)benzo-1,2,3-triazole (200 mg)
2-(3-dodecyl-2-hydroxy-5-methylphenyl)benzo-1,2,3-triazole (200 mg)
trinonyl phosphate (300 mg)
2,5-di-tert-octylhydroquinone (50 mg)
5-[2,5-dihydroxy-4-(4-hexyloxycarbonyl-1,1-dimethylbutyl)-phenyl]-5-methylhexanoic acid hexyl ester (50 mg)

Red-Sensitive Layer
2-[α-(2,4-di-tert-amylphenoxy)butanamido]-4,6-di-chloro-5-ethylphenol (150 mg)
2,4-dichloro-3-ethyl-6-hexadecanamidophenol (150 mg)
4-chloro-2-(1,2,3,4,5-pentafluorobenzamido)-5-[2-(2,4-di-tert-amylphenoxy)-3-methylbutanamido]phenol (100 mg)
dioctyl phthalate (100 mg)
dicyclohexyl phthalate (100 mg)
gelatin (1200 mg)
5-chloro-2-(3,5-di-tert-butyl-2-hydroxyphenyl)benzo-1,2,3-triazole (100 mg)
2-(3-dodecyl-2-hydroxy-5-methylphenyl)benzo-1,2,3-triazole (100 mg)
3,5-di-tert-butyl-4-hydroxy-(2,4-di-tert-amylphenyl)-benzoate (50 mg)
poly(N-tert-butylacrylamide) (300 mg)
N,N-diethyl-2,4-di-tert-amylphenoxyacetamide (100 mg)
2,5-di-tert-octylhydroquinone (50 mg)
red-sensitive silver chlorobromide emulsion (200 mg)
The top layer is produced with and without UV absorber;

With UV Absorber:
2,5-di-tert-octylhydroquinone (20 mg)
5-[2,5-dihydroxy-4-(4-hexyloxycarbonyl-1,1-dimethylbutyl)-phenyl]-5-methylhexanoic acid hexyl ester (20 mg)
gelatin (400 mg)
trinonyl phosphate (120 mg)
UV absorber according to the invention from Example A3 (300 mg)

Without UV Absorber:
gelatin (800 mg)
2,4-Dichloro-6-hydroxytriazine potassium salt solution is used as curing agent, and the sodium salt of diisobutyinaphthalenesulfonic acid is used as wetting agent.

Three step wedges having a density difference of 0.3 log E per step are exposed onto each of the samples (with blue, green or red light, respectively). The procedure according to the RA-4 (Kodak) processing process for colour papers is then carried out.

After exposure and processing, the reflection densities are measured in red for the cyan step, in green for the magenta step and in blue for the yellow step at a density of from 0.9 to 1.1 of the wedges. The wedges are then exposed with a total of 15 kJ/cm² in an Atlas exposure apparatus and the reflection densities are re-measured.

In the case of the magenta wedge, the reflection density before and after exposure is also measured in blue for yellowing.

The presence of the compound according to the invention reduces the density loss of the cyan, magenta and yellow image-producing colours and also the yellowing of the magenta layer.

Example B8

Stabilisation of a 2-Layer Metallic Finish

The UV absorbers according to the invention are tested in an application concentration of 1.5 % (based on binder solids) in a 2-component polyurethane clear surface-coating. Testing is carried out with and without the addition of the sterically hindered amine Tinuvin® 292 (HALS; Ciba Specialty Chemicals; main component bis(1,2,2,6,6-pentamethylpiperidyl) sebacate), application concentration 1% based on binder solids.

| Surface-coating formulation: | |
|---|---|
| a) polyol component | |
| Macrynal™ SM 510n (60%)a) | 75.0 g |
| butyl glycol acetate | 15.0 g |
| Solvesso™ 100b) | 6.1 g |
| methyl isobutyl ketone | 3.6 g |
| zinc octoate (8% metal) | 0.1 g |
| BYK™ 300c) | 0.2 g |
| total | 100.0 g |
| b) isocyanate component | |
| Desmodur™ N 75d) | 40.0 g | a)OH-functional poly(meth)acrylate (formerly Vianova Resins GmbH, Germany).
b)mixture of aromatic hydrocarbons of boiling range 161–178° C. (produced by: Esso).
c)flow improver based on dimethylpolysiloxane (Byk Chemie, Wesel, Germany).
d)isocyanate curing agent (75% by weight in methoxypropyl acetate/xylene 1:1; Bayer AG).

The UV absorbers according to the invention are stirred into the polyol component. A clear surface-coating formulation not containing any light stabiliser is used as a reference. Immediately before application, the isocyanate component is added.

The finished clear surface-coating is applied, after dilution to spraying viscosity, to prefabricated aluminium sheets (Uniprime Epoxy, silver-metallic base coating) and then dried at 80° C./45 min. A dry layer thickness of 40 μm is obtained.

The samples are then subjected to accelerated weathering (UVCON® weathering apparatus of Atlas Corporation, UVB-313-lamps, cycle 8 hours' exposure at 70° C. and 4 hours' condensation at 50° C.). In the course of the weathering test, the gloss (20° gloss, DIN

What is claimed is:
1. A compound of formula I

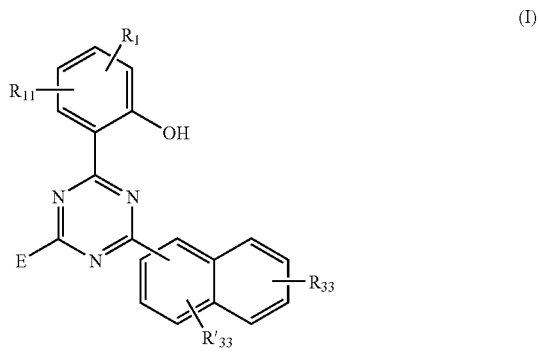

wherein
E corresponds to the formula

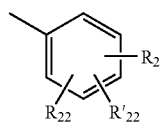

or to the formula

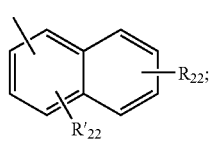

$R_1$ is hydrogen or $OR_3$;
$R_2$ is H, $C_1$–$C_{18}$alkyl; $C_2$–$C_6$alkenyl; phenyl; phenyl substituted by $C_1$–$C_8$alkyl or by $C_1$–$C_8$alkoxy; $C_7$–$C_{11}$phenylalkyl; $C_5$–$C_{12}$cycloalkyl; $COOR_4$; CN; $NH_2$, $NHR_7$, —N($R_7$)($R_8$), NH—CO—$R_5$; halogen; $C_1$–$C_{18}$haloalkyl; —S—$R_3$ or —O—$R_3$;
$R_3$ is H, $C_1$–$C_{18}$alkyl; $C_5$–$C_{12}$cycloalkyl; $C_3$–$C_{18}$alkenyl; phenyl; $C_1$–$C_{18}$alkyl that is substituted by phenyl, vinylphenyl, OH, $C_1$–$C_{18}$alkoxy, $C_5$–$C_{12}$cycloalkoxy, $C_3$–$C_{18}$alkenyloxy, halogen, —COOH, —COOR_4, —O—CO—$R_5$, —O—CO—O—$R_6$, —CO—$NH_2$, —CO—NHR_7, —CO—N($R_7$)($R_8$), CN, $NH_2$, $NHR_7$, —N($R_7$)($R_8$), —NH—CO—$R_5$, phenoxy, $C_1$–$C_{18}$alkyl-substituted phenoxy, phenyl-$C_1$–$C_4$alkoxy, $C_6$–$C_{15}$bicycloalkoxy, $C_6$–$C_{15}$bicycloalkyl-alkoxy, $C_6$–$C_{15}$bicycloalkenyl-alkoxy and/or by $C_6$–$C_{15}$tricycloalkoxy; $C_5$–$C_{12}$cycloalkyl that is substituted by OH, $C_1$–$C_4$alkyl, $C_2$–$C_6$alkenyl or by —O—CO—$R_5$; —CO—$R_9$ or —$SO_2$—$R_{10}$; or $R_3$ is $C_3$–$C_{50}$alkyl that is interrupted by one or more oxygen atoms and/or is substituted by OH, phenoxy or by $C_7$–$C_{18}$alkylphenoxy;
or $R_3$ has one of the definitions —A; —$CH_2$—CH(XA)—$CH_2$—O—$R_{12}$; —$CR_{13}R'_{13}$—($CH_2$)$_m$—X—A; —$CH_2$—CH(OA)—$R_{14}$; —$CH_2$—CH(OH)—$CH_2$—XA;

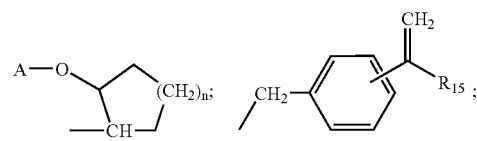

—CR$_{15}$R'$_{15}$—C(=CH$_2$)—R"$_{15}$; —CR$_{13}$R'$_{13}$—(CH$_2$)$_m$—CO—X—A;

—CR$_{13}$R'$_{13}$—(CH$_2$)$_m$—CO—O—CR$_{15}$R'$_{15}$—C(=CH$_2$)—R"15 or —CO—O—CR$_{15}$R'$_{15}$—C(=CH$_2$)—R"$_{15}$, wherein A is —CO—CR$_{16}$=CH—R$_{17}$;

R$_4$ is C$_1$–C$_{18}$alkyl; C$_3$–C$_{18}$alkenyl; phenyl; C$_7$–C$_{11}$phenylalkyl; C$_5$–C$_{12}$cycloalkyl; or C$_3$–C$_{50}$alkyl that is interrupted by one or more of —O—, —NH—, —NR$_7$— and —S— and may be substituted by OH, phenoxy or by C$_7$–C$_{18}$alkylphenoxy; or is C$_2$–C$_{12}$ hydroxyalkyl;

R$_5$ is H; C$_1$–C$_{18}$alkyl; C$_1$–C$_{18}$alkyl substituted by COOH or by COOR$_4$; C$_2$–C$_{18}$alkenyl; C$_2$–C$_{18}$alkenyl substituted by COOH or by COOR$_4$; C$_5$–C$_{12}$cycloalkyl; phenyl; C$_7$–C$_{11}$phenylalkyl; C$_6$–C$_{15}$bicycloalkyl; C$_6$–C$_{15}$bicycloalkenyl; or C$_6$–C$_{15}$tricycloalkyl;

R$_6$ is H; C$_1$–C$_{18}$alkyl; C$_3$–C$_{18}$alkenyl; phenyl; C$_7$–C$_{11}$phenylalkyl; or C$_5$–C$_{12}$cycloalkyl;

R$_7$ and R$_8$, independently of each other, are C$_1$–C$_{12}$alkyl; C$_3$–C$_{12}$alkoxyalkyl; C$_4$–C$_{16}$dialkylaminoalkyl; or C$_5$–C$_{12}$cycloalkyl; or together form C$_3$–C$_9$-alkylene, -oxaalkylene or -azaalkylene;

R$_9$ is C$_1$–C$_{18}$alkyl; C$_2$–C$_{18}$alkenyl; phenyl; C$_5$–C$_{12}$cycloalkyl; C$_7$–C$_{11}$phenylalkyl; C$_6$–C$_{15}$bicycloalkyl, C$_6$–C$_{15}$bicycloalkyl-alkyl, C$_6$–C$_{15}$bicycloalkenyl, or C$_6$–C$_{15}$tricycloalkyl;

R$_{10}$ is C$_1$–C$_{12}$alkyl; phenyl; naphthyl or C$_7$–C$_{14}$alkylphenyl;

the radicals R$_{11}$, R$_{22}$ and R$_{33}$, independently of one another, are H; C$_1$–C$_{18}$alkyl; C$_3$–C$_6$alkenyl; C$_5$–C$_{12}$cycloalkyl; phenyl; naphthyl; biphenylyl; C$_7$–C$_{11}$phenylalkyl; C$_7$–C$_{14}$alkylphenyl; halogen; C$_1$–C$_{18}$ haloalkyl; or C$_1$–C$_{18}$alkoxy;

R$_{12}$ is C$_1$–C$_{18}$alkyl; C$_3$–C$_{18}$alkenyl; phenyl; phenyl substituted by from one to three of the radicals C$_1$–C$_8$alkyl, C$_1$–C$_8$alkoxy, C$_3$–C$_8$alkenyloxy, halogen and trifluoromethyl; C$_7$–C$_{11}$phenylalkyl; C$_5$–C$_{12}$cycloalkyl; C$_6$–C$_{15}$tricycloalkyl; C$_6$–C$_{15}$bicycloalkyl; C$_6$–C$_{15}$bicycloalkyl-alkyl; C$_6$–C$_{15}$bicycloalkenylalkyl; —CO—R$_5$; or C$_3$–C$_{50}$alkyl that is interrupted by one or more of —O—, —NH—, —NR$_7$— and —S— and may be substituted by OH, phenoxy or by C$_7$–C$_{18}$alkylphenoxy;

R$_{13}$ and R'$_{13}$, independently of each other, are H; C$_1$–C$_{18}$alkyl; or phenyl;

R$_{14}$ is C$_1$–C$_{18}$alkyl; C$_3$–C$_{12}$alkoxyalkyl; phenyl; or phenyl-C$_1$–C$_4$alkyl;

R$_{15}$, R'$_{15}$ and R"$_{15}$, independently of one another, are H or CH$_3$;

R$_{16}$ is H; —CH$_2$—COO—R; C$_1$–C$_4$alkyl; or CN;

R$_{17}$ is H; —COOR$_4$; C$_1$–C$_{17}$alkyl; or phenyl;

R'$_{22}$ and R'$_{33}$, independently of each other, have one of the definitions of R$_{11}$ or OR$_3$; or are NH$_2$, NHR$_7$, NH—CO—R$_5$; —S—R$_3$ or —N(R$_7$)(R$_8$);

X is —NH—; —NR$_7$—; —O—; —NH—(CH$_2$)$_p$—NH—; or —O—(CH$_2$)$_q$—NH—;

m is the number 0–19;
n is the number 1–8;
p is the number 0–4; and
q is the number 2–4.

2. A compound of formula I according to claim 1, wherein
R$_1$ is hydrogen or OR$_3$;

R$_2$ is H, C$_1$–C$_{18}$alkyl; C$_2$–C$_6$alkenyl; phenyl; phenyl substituted by C$_1$–C$_8$alkyl or by C$_1$–C$_8$alkoxy; NH—CO—R$_5$; halogen; C$_1$–C$_{18}$ haloalkyl; or C$_1$–C$_{18}$alkoxy;

R$_3$ is H, C$_1$–C$_{18}$alkyl; C$_5$–C$_{12}$cycloalkyl; C$_3$–C$_{18}$alkenyl; phenyl; C$_1$–C$_{18}$alkyl that is substituted by phenyl, vinylphenyl, OH, C$_1$–C$_{18}$alkoxy, C$_5$–C$_{12}$cycloalkoxy, C$_3$–C$_{18}$alkenyloxy, halogen, —COOH, —COOR$_4$, —O—CO—R$_5$, —O—CO—O—R$_6$, —CO—NH$_2$, —CO—NHR$_7$, —CO—N(R$_7$)(R$_8$), CN, NH$_2$, NHR$_7$, —N(R$_7$)(R$_8$), —NH—CO—R$_5$, phenoxy, C$_1$–C$_{18}$alkyl-substituted phenoxy and/or by phenyl-C$_1$–C$_4$alkoxy; C$_5$–C$_{12}$cycloalkyl that is substituted by OH, C$_1$–C$_4$alkyl, C$_2$–C$_6$alkenyl or by —O—CO—R$_5$; or R$_3$ is —SO$_2$—R$_{10}$; or R$_3$ is C$_3$–C$_{50}$alkyl that is interrupted by one or more oxygen atoms and/or is substituted by OH, phenoxy or by C$_7$–C$_{18}$alkylphenoxy; or R$_3$ has one of the definitions —CO—CH=CH$_2$ and —CO—C(CH$_3$)=CH$_2$;

R$_4$ is C$_1$–C$_{18}$alkyl; C$_3$–C$_{18}$alkenyl; phenyl; C$_7$–C$_{11}$phenylalkyl; C$_5$–C$_{12}$cycloalkyl; or C$_3$–C$_{50}$alkyl that is interrupted by one or more of —O—, —NH—, —NR$_7$— and —S— and may be substituted by OH, phenoxy or by C$_7$–C$_{18}$alkylphenoxy; or is C$_2$–C$_{12}$ hydroxyalkyl;

R$_5$ is H; C$_1$–C$_{18}$alkyl; C$_2$–C$_{18}$alkenyl; C$_5$–C$_{12}$cycloalkyl; phenyl; or C$_7$–C$_{11}$phenylalkyl;

R$_6$ is H; C$_1$–C$_{18}$alkyl; C$_3$–C$_{18}$alkenyl; phenyl; C$_7$–C$_{11}$phenylalkyl; or C$_5$–C$_{12}$cycloalkyl;

R$_7$ and R$_8$, independently of each other, are C$_1$–C$_{12}$alkyl; C$_3$–C$_{12}$alkoxyalkyl; C$_4$–C$_{16}$dialkylaminoalkyl; or cyclohexyl; or together form C$_3$–C$_9$-alkylene or -oxaalkylene;

R$_{10}$ is C$_1$–C$_{12}$alkyl; phenyl; naphthyl or C$_7$–C$_{14}$alkylphenyl;

the radicals R$_{11}$, R$_{22}$ and R$_{33}$, independently of one another, are H, C$_7$–C$_{11}$phenylalkyl or C$_1$–C$_8$alkyl; and R'$_{22}$ and R'$_{33}$, independently of each other, are H; C$_1$–C$_8$alkyl; C$_3$–C$_6$alkenyl; C$_7$–C$_{11}$phenylalkyl; C$_5$–C$_{12}$cycloalkyl; phenyl; naphthyl; biphenylyl; C$_7$–C$_{11}$phenylalkyl; C$_7$–C$_{14}$alkylphenyl; NHR$_7$; —N(R$_7$)(R$_8$); halogen or C$_1$–C$_{18}$ haloalkyl; or have one of the definitions of OR$_3$.

3. A compound according to claim 1 corresponding to formula IIa or IIb

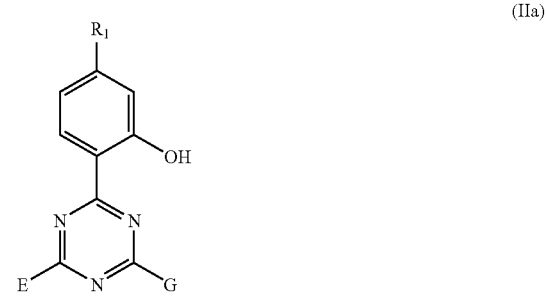

-continued

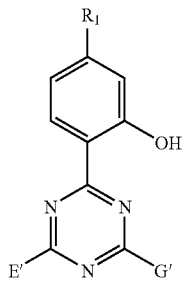
(IIb)

wherein
E corresponds to the formula

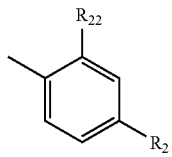

or G;
E' corresponds to the formula

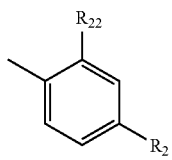

or G';
G corresponds to the formula

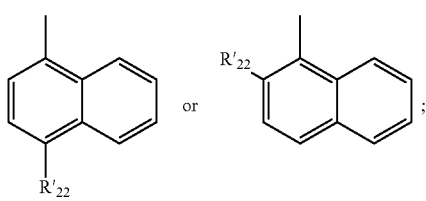

and G' corresponds to the formula

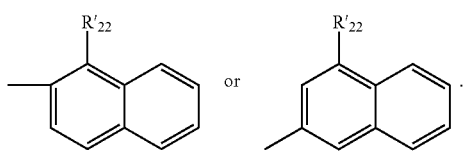

4. A compound of formula I according to claim 1, wherein
$R_1$ is hydrogen or $OR_3$;
$R_2$ is H, $C_1$–$C_8$alkyl; phenyl; phenyl substituted by methyl or by methoxy; NH—CO—$R_5$; trifluoromethyl; or $C_1$–$C_{18}$alkoxy;
$R_3$ is H, $C_1$–$C_{18}$alkyl; cyclohexyl; $C_3$–$C_{18}$alkenyl; $C_1$–$C_{18}$alkyl that is substituted by phenyl, OH, $C_1$–$C_{18}$alkoxy, cyclohexyloxy, halogen, —COOH, —COO$R_4$, —O—CO—$R_5$, —CO—NH$R_7$, —CO—N($R_7$)($R_8$), CN, NH$R_7$, —N($R_7$)($R_8$), —NH—CO—$R_5$ and/or by phenyl-$C_1$–$C_4$alkoxy; or cyclohexyl that is substituted by OH, $C_1$–$C_4$alkyl, $C_2$–$C_6$alkenyl or by —O—CO—$R_5$;
$R_4$ is $C_1$–$C_{18}$alkyl; $C_7$–$C_{11}$phenylalkyl; $C_5$–$C_{12}$cycloalkyl; or $C_2$–$C_{12}$ hydroxyalkyl;
$R_5$ is H; $C_1$–$C_{18}$alkyl; $C_2$–$C_8$alkenyl; cyclohexyl; phenyl; or $C_7$–$C_{11}$phenylalkyl;
$R_7$ and $R_8$, independently of each other, are $C_3$–$C_{12}$alkyl or cyclohexyl; or together form $C_3$–$C_9$oxaalkylene;
the radicals $R_{11}$, $R_{22}$ and $R_{33}$, independently of one another, are H, $C_7$–$C_{11}$phenylalkyl or $C_1$–$C_8$alkyl; and
$R'_{22}$ and $R'_{33}$, independently of each other, are H; $C_1$–$C_8$alkyl; $C_3$–$C_6$alkenyl; $C_7$–$C_{11}$phenylalkyl; $C_5$–$C_{12}$cycloalkyl; trifluoromethyl; phenyl; naphthyl; biphenylyl; $C_7$–$C_{11}$phenylalkyl; $C_7$–$C_{14}$alkylphenyl; or NH$R_7$ or —N($R_7$)($R_8$); or have one of the definitions of $OR_3$.

5. A compound of formula IIa or IIb according to claim 3, wherein
E in formula IIa corresponds to the formula

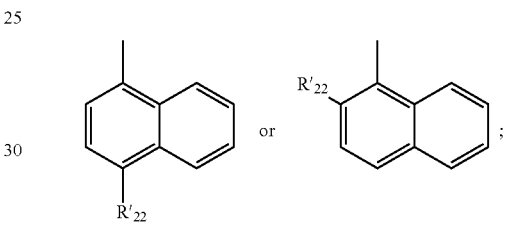

E' in formula IIb corresponds to the formula

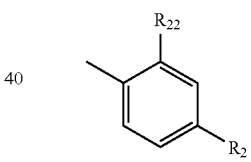

or G';
G corresponds to the formula

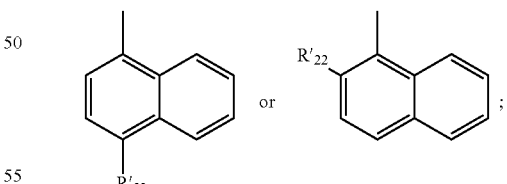

and G' corresponds to the formula

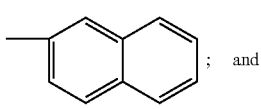 ; and $R_1$ is hydrogen or $OR_3$;
$R_2$ is H, $C_1$–$C_8$alkyl; methoxy or phenyl;

$R_3$ is H, $C_1$–$C_{18}$alkyl; $C_1$–$C_{12}$alkyl that is substituted by OH, $C_1$–$C_{18}$alkoxy, COOR$_4$ or by —O—CO—R$_5$;

$R_4$ is $C_1$–$C_{18}$alkyl;

$R_5$ is H; $C_1$–$C_{18}$alkyl; or $C_7$–$C_{11}$phenylalkyl; and $R_{22}$ is H or methyl; and $R'_{22}$ is H or $C_1$–$C_4$alkyl or has one of the definitions of OR$_3$.

6. A composition comprising A) an organic material that is sensitive to damage by light, oxygen or heat and B) as stabiliser at least one compound of formula I according to claim 1.

7. A composition according to claim 6 comprising components A) and B), wherein component A) is a synthetic organic polymer, a binder for surface-coatings, a recording material or animal or human hair.

8. A composition according to claim 6 comprising, in addition to components A) and B), as further component one or more compounds selected from the group consisting of pigments, dyes, plasticisers, antioxidants, flow improvers, further UV absorbers, metal passivators, metal oxides, organophosphorus compounds, hydroxylamines, sterically hindered amines and flame-proofing agents.

9. A composition according to claim 6 comprising from 0.01 to 10% by weight of component B) based on the weight of the composition.

10. A composition according to claim 6, wherein component A) is a binder for surface-coatings or is a colour photographic material comprising, on a support, at least one photo-sensitive silver halide emulsion layer and optionally an intermediate layer and/or a protection layer, at least one of the said layers comprising component B).

11. A composition according to claim 7 where component A) is a recording material comprising component B) in an amount of from 0.001 to 10 g per m$^2$.

12. A method of stabilizing organic material against damage by light, oxygen or heat, wherein a compound of formula I according to claim 1 is mixed with or applied to that material.

13. A cosmetic preparation comprising one or more compounds of formula I according to claim 1 and at least one hair- and skin-cosmetically tolerable carrier or excipient.

* * * * *